(12) United States Patent
Caille et al.

(10) Patent No.: US 9,757,367 B2
(45) Date of Patent: Sep. 12, 2017

(54) CALCIUM PROPANE-2-SULFINATE DIHYDRATE

(71) Applicant: AMGEN INC., Thousand Oaks, CA (US)

(72) Inventors: Sebastien Caille, Moorpark, CA (US); Filisaty Vounatsos, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 15/175,821

(22) Filed: Jun. 7, 2016

(65) Prior Publication Data

US 2016/0289178 A1 Oct. 6, 2016

Related U.S. Application Data

(62) Division of application No. 14/301,087, filed on Jun. 10, 2014, now Pat. No. 9,376,386.

(60) Provisional application No. 61/833,196, filed on Jun. 10, 2013.

(51) Int. Cl.
| | | |
|---|---|---|
| *C07C 313/02* | (2006.01) |
| *A61K 31/451* | (2006.01) |
| *C07D 211/94* | (2006.01) |
| *C07D 491/048* | (2006.01) |
| *C07C 309/25* | (2006.01) |
| *C07C 309/04* | (2006.01) |
| *C07D 498/04* | (2006.01) |
| *C07D 211/76* | (2006.01) |
| *C07C 309/35* | (2006.01) |

(52) U.S. Cl.
CPC .......... *A61K 31/451* (2013.01); *C07C 309/04* (2013.01); *C07C 309/25* (2013.01); *C07C 309/35* (2013.01); *C07C 313/02* (2013.01); *C07D 211/76* (2013.01); *C07D 211/94* (2013.01); *C07D 491/048* (2013.01); *C07D 498/04* (2013.01); *C07B 2200/13* (2013.01)

(58) Field of Classification Search
None
See application file for complete search history.

(56) References Cited

U.S. PATENT DOCUMENTS

| 3,308,121 A | 3/1967 | Gannon et al. |
| 3,518,236 A * | 6/1970 | Hunter ............... C08K 5/41 525/329.3 |
| 5,334,720 A | 8/1994 | Schmiesing et al. |
| 6,620,815 B1 | 9/2003 | Lagu et al. |
| 6,860,940 B2 | 3/2005 | Segelke et al. |
| 7,015,041 B2 | 3/2006 | Santarsiero et al. |
| 7,052,545 B2 | 5/2006 | Quake et al. |
| 7,195,670 B2 | 3/2007 | Hansen et al. |
| 7,214,540 B2 | 5/2007 | DeLucas et al. |
| 7,229,500 B2 | 6/2007 | Haushalter et al. |
| 7,425,638 B2 | 9/2008 | Haley et al. |
| 7,776,875 B2 | 8/2010 | Chen et al. |
| 8,569,341 B2 | 10/2013 | Gribble, Jr. et al. |
| 8,952,036 B2 | 2/2015 | Rew |
| 9,296,736 B2 | 3/2016 | Bartberger et al. |
| 9,376,386 B2 | 6/2016 | Bio et al. |
| 9,376,425 B2 | 6/2016 | Bartberger et al. |
| 9,593,129 B2 | 3/2017 | Bartberger et al. |
| 9,623,018 B2 | 4/2017 | Bio et al. |
| 2004/0186134 A1 | 9/2004 | O'Connor et al. |
| 2007/0129416 A1 | 6/2007 | Ding et al. |
| 2008/0280769 A1 | 11/2008 | Doemling |
| 2009/0143364 A1 | 6/2009 | Fotouhi et al. |
| 2009/0163512 A1 | 6/2009 | Chen et al. |
| 2011/0319378 A1 | 12/2011 | Gribble. Jr. et al. |
| 2014/0235629 A1 | 8/2014 | Bartberger et al. |
| 2014/0315895 A1 | 10/2014 | Bartberger et al. |
| 2014/0364455 A1 | 12/2014 | Bio et al. |
| 2016/0002185 A1 | 1/2016 | Bartberger et al. |
| 2016/0039774 A1 | 2/2016 | Gonzalez Buenrostro et al. |
| 2016/0137667 A1 | 5/2016 | Bartberger et al. |
| 2016/0264526 A1 | 9/2016 | Bio et al. |
| 2016/0287570 A1 | 10/2016 | Bio et al. |
| 2016/0289190 A1 | 10/2016 | Bio et al. |
| 2016/0289243 A1 | 10/2016 | Bio et al. |
| 2017/0144971 A1 | 5/2017 | Bartberger et al. |

FOREIGN PATENT DOCUMENTS

| CN | 102153557 A | 8/2011 | |
| DE | 3246148 A1 | 6/1984 | |
| JP | EP 0408357 A2 * | 1/1991 | ............... C08F 2/50 |
| TW | 200801000 A | 1/2008 | |
| TW | 200808781 A | 2/2008 | |
| WO | WO95/23135 A1 | 8/1995 | |
| WO | WO96/06095 A1 | 2/1996 | |
| WO | WO97/30045 A1 | 8/1997 | |
| WO | WO99/06397 A2 | 2/1999 | |

(Continued)

OTHER PUBLICATIONS

Braverman "Product class 3: alkanesulfinic acids and acyclic derivatives." Science of Synthesis, 2007, 39, 187-243.*
Allen Jr. "Aliphatic Sulfinic Acids. I. Analysis and Identification" Journal of Organic Chemistry, 1942, 7, 23-30.*
Fenton Journal of the Chemical Society, 1929, 2338-2341.*
West, Anthony R., "Solid State Chemistry and its Applications", Wiley, New York, 1988, pp. 358 & 365.*
U.S. Appl. No. 15/163,186, filed May 24, 2016, Amgen Inc.
U.S. Appl. No. 15/175,798, filed Jun. 7, 2016, Amgen Inc.
U.S. Appl. No. 15/175,805, filed Jun. 7, 2016, Amgen Inc.
U.S. Appl. No. 15/175,824, filed Jun. 7, 2016, Amgen Inc.
"Guidance for Industry ANDAs: Pharmaceutical Solid Polymorphism Chemistry Manufacturing, and Controls Information," U.S. Department of Health and Human Services, Food and Drug Administration, Center for Drug Evaluation and Research (CDER), Jul. 2007, pp. 1-13.

(Continued)

*Primary Examiner* — David K O'Dell
(74) *Attorney, Agent, or Firm* — Markus Bergauer

(57) ABSTRACT

The present invention provides processes for making 2-((3R, 5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid as well as intermediates and processes for making the intermediates. Also provided are crystalline forms of the compound and the intermediates.

2 Claims, 13 Drawing Sheets

(56) References Cited

FOREIGN PATENT DOCUMENTS

| WO | WO99/31507 A1 | 6/1999 |
|---|---|---|
| WO | WO02/017912 A1 | 3/2002 |
| WO | WO02/089738 A2 | 11/2002 |
| WO | WO02/094787 A1 | 11/2002 |
| WO | WO03/051359 A1 | 6/2003 |
| WO | WO2004/031149 A1 | 4/2004 |
| WO | WO2005/110996 A1 | 11/2005 |
| WO | WO2005/123691 A1 | 12/2005 |
| WO | WO2006/097261 A1 | 9/2006 |
| WO | WO2006/107859 A2 | 10/2006 |
| WO | WO2006/107860 A2 | 10/2006 |
| WO | WO2007/063013 A1 | 6/2007 |
| WO | WO2007/104664 A1 | 9/2007 |
| WO | WO2008/005268 A1 | 1/2008 |
| WO | WO2008/010953 A2 | 1/2008 |
| WO | WO2008/021338 A2 | 2/2008 |
| WO | WO2008/021339 A2 | 2/2008 |
| WO | WO2008/076754 A2 | 6/2008 |
| WO | WO2008/110793 A1 | 9/2008 |
| WO | WO2008/125487 A1 | 10/2008 |
| WO | WO2008/141975 A1 | 11/2008 |
| WO | WO2009/004430 A1 | 1/2009 |
| WO | WO2009/007750 A1 | 1/2009 |
| WO | WO2009/047161 A1 | 4/2009 |
| WO | WO2009/082038 A2 | 7/2009 |
| WO | WO2009/114950 A1 | 9/2009 |
| WO | WO2009/156735 A2 | 12/2009 |
| WO | WO2010/028862 A1 | 3/2010 |
| WO | WO2010/031713 A1 | 3/2010 |
| WO | WO2010/121995 A1 | 10/2010 |
| WO | WO2011/023677 A1 | 3/2011 |
| WO | WO2011/067185 A1 | 6/2011 |
| WO | WO2011/076786 A1 | 6/2011 |
| WO | WO2011/153509 A1 | 12/2011 |
| WO | WO2013/049250 A1 | 4/2013 |
| WO | WO2014/130470 A1 | 8/2014 |
| WO | WO2014/134201 A1 | 9/2014 |
| WO | WO2014/151863 A1 | 9/2014 |
| WO | WO2014/200937 A1 | 12/2014 |

OTHER PUBLICATIONS

Allen, J. G. et al., "Discovery and Optimization of Chromenotriazolopyrimidines as Potent Inhibitors of the Mouse Double Minute 2-Tumor Protein 53 Protein-Protein Interaction," Journal of Medicinal Chemistry 52(22), 7044-7053 (2009).

Anthony, N. J. et al., "Pseudo-Allylic A1,3 Strain as a Conformational Control Element: Stereoselective Syntheses of ψ[CH20] Pseudodipeptides," Tetrahedron Letters 36(22), 3821-3824 (1995).

Garcia Ruano, J. L. et al., "Synthesis of 2-phenyl-, 3-phenyl-, cis-2,3-diphenyl-, and trans-2,3-diphenyl-1,4-thiazanes and derivatives (N-methyl, N-alkoxycarbonyl, S-oxides, and S,S-dioxides)," Journal of Organic Chemistry 57(15), 4215-4224 (1992).

Gattermann, L. "The Practical Methods of Organic Chemistry," 1896, MacMillan: New York, pp. 1-14.

Gonzalez, A. Z. et al., "Novel Inhibitors of the MDM2-p53 Interaction Featuring Hydrogen Bond Acceptors as Carboxylic Acid Isosteres," Journal of Medicinal Chemistry 57(7), 2963-2988 (2014).

He, Q. et al., "Novel morpholin-3-one derivatives induced apoptosis and elevated the level of P53 and Fas in A549 lung cancer cells," Bioorganic & Medicinal Chemistry 15(11), 3889-3895 (2007).

International Search Report, PCT/US2011/039184, dated Sep. 9, 2011, pp. 1-3.

International Search Report, PCT/US2012/057389, dated Jan. 18, 2013, pp. 1-4.

International Search Report, PCT/US2014/016971, dated May 15, 2014, pp. 1-5.

International Search Report, PCT/US2014/018759, dated Jun. 12, 2014, pp. 1-5.

International Search Report, PCT/US2014/026584, dated Jun. 26, 2014, pp. 1-5.

International Search Report, PCT/US2014/041594, dated Aug. 18, 2014, pp. 1-7.

Lawrence, H. R. et al., "Identification of a disruptor of the MDM2-p53 protein—protein interaction facilitated by high-throughput in silico docking," Bioorganic & Medicinal Chemistry Letters 19, 3756-3759 (2009).

Michelsen, K. et al., "Ordering of the N-Terminus of Human MDM2 by Small Molecule Inhibitors," Journal American Chemical Society 134(41), 17059-17067 (2012).

Morissette, S. L. et. al. "High-throughput crystallization: polymorphs, salts, co-crystals and solvates of pharmaceutical solids," Advanced Drug Delivery Reviews 56, 275-300 (2004).

Nakayama, H. et al., "Hydrates of Organic Compounds. X. The Formation of Clathrate Hydrates of Tetrabutylammonium Alkanesulfonates," Bulletin of the Chemical Society of Japan, 833-837 (1986).

Notice of Allowance dated Jul. 22, 2016 for U.S. Appl. No. 15/008,342, filed Jan. 27, 2016, pp. 1-9.

Office Action dated Jul. 1, 2015 for U.S. Appl. No. 14/301,087, filed Jun. 10, 2014, pp. 1-11.

Office Action dated Mar. 24, 2015 for U.S. Appl. No. 14/301,087, filed Jun. 10, 2014, pp. 1-9.

Patani, G. A. et al., "Bioisosterism: A Rational Approach in Drug Design," Chemical Reviews 96(8), 3147-3176 (1996).

Rew, Y. et al., "Structure-Based Design of Novel Inhibitors of the MDM2-p53 Interaction," Journal of Medicinal Chemistry 55(11), 4936-4954 (2012).

Rothweiler, U. et al., "Isoquinolin-1-one Inhibitors of the MDM2-p53 Interaction," Chem. Med. Chem. 3(7), 1118-1128 (2008).

Stefanovsky, J. N. et al., "Ueber die Verhaeltnisse bei Ringschlussreaktionen epimerer 2-Amino-1,2-diphenyl-aethanole," Chem. Ber. 102, 717-727 (1969), cited on p. 19 of in Office Action dated Dec. 24, 2014 for U.S. Appl. No. 14/347,628, pp. 1-21 (attached).

Sun, D. et al., "Discovery of AMG 232, a Potent, Selective, and Orally Bioavailable MDM2-p53 Inhibitor in Clinical Development," Journal of Medicinal Chemistry 57(4), 1454-1472 (2014).

Written Opinion of the International Searching Authority, PCT/US2011/039184, dated Sep. 9, 2011, pp. 1-5.

Written Opinion of the International Searching Authority, PCT/US2012/057389, dated Jan. 18, 2013, pp. 1-6.

Written Opinion of the International Searching Authority, PCT/US2014/016971, dated May 15, 2014, pp. 1-3.

Written Opinion of the International Searching Authority, PCT/US2014/018759, dated Jun. 12, 2014, pp. 1-7.

Written Opinion of the International Searching Authority, PCT/US2014/026584, dated Jun. 26, 2014, pp. 1-6.

Written Opinion of the International Searching Authority, PCT/US2014/041594, dated Aug. 18, 2014, pp. 1-12.

Zeitler, J. A. et al. "Characterization of Temperature-Induced Phase Transitions in Five Polymorphic Forms of Sulfathiazole by Terahertz Pulsed Spectroscopy and Differential Scanning Calorimetry," Journal of Pharmaceutical Sciences 95(11), 2486-2498 (2006).

Caille, S., "Amgen Chemical Process Development: A Process to Manufacture AMG 232," The 2016 Amgen—UCLA Lectureship, Slide Deck presented on Mar. 3, 2016, UCLA Department of Chemistry and Biochemistry, CA, USA, pp. 1-32 (2016).

Damia, G. et al., "Contemporary pre-clinical development of anti-cancer agents—What are the optimal preclinical models?," European Journal of Cancer 45, 2768-2781 (2009).

Johnson, J. I. et al., "Relationships between drug activity in NCI preclinical in vitro and in vivo models and early clinical trials," British Journal of Cancer 84, 1424-1431 (2001).

Ledford, H., "US cancer institute overhauls cell lines," Nature 530, 391 (2016).

Ocana, A. et al., "Preclinical development of molecular-targeted agents for cancer," Nat. Rev. Clin. Oncol. 8, 200-209 (2011).

Office Action dated Mar. 15, 2017 for U.S. Appl. No. 15/175,798, filed Jun. 7, 2016, pp. 1-10.

(56) References Cited

OTHER PUBLICATIONS

Office Action dated Mar. 21, 2017 for U.S. Appl. No. 15/175,824, filed Jun. 7, 2016, pp. 1-6.
Office Action dated Mar. 22, 2017 for U.S. Appl. No. 15/175,798, filed Jun. 7, 2016, pp. 1-10.
Office Action dated Mar. 6, 2017 for U.S. Appl. No. 15/163,186, filed May 24, 2016, pp. 1-10.
Patel, S. et al., "Small-molecule inhibitors of the p53-HDM2 interaction for the treatment of cancer," Expert Opin. Investig. Drugs 17, 1865-1882 (2008).
Rees, W. S., "Alkaline Earth Metals: Inorganic Chemistry," Encyclopedia of Inorganic Chemistry, John Wiley & Sons, Ltd, pp. 1-22 (2006).
Sharma, S. V. et al., "Cell line-based platforms to evaluate the therapeutic efficacy of candidate anticancer agents," Nature Reviews 10, 241-253 (2010).

\* cited by examiner

Compound A Amorphous

Compound A Propanol Solvate

DSC of Compound A Crystalline Anhydrous

DSC of Crystalline (3S, 5S, 6R, 8S)-8-allyl-6-(3-chlorophenyl)-5-(4-chlorophenyl)-3-isopropyl-8-methyl-2, 3,5,6,7, 8-hexahydrooxazolo[3,2-a]pyridin-4-ium naphthalene-1-sulfonate, hemi-toluene solvate DSC of Compound A Ethanolate DSC of Compound A DABCO salt

CALCIUM PROPANE-2-SULFINATE DIHYDRATE

CROSS-REFERENCE TO RELATED APPLICATIONS

This application is a divisional application of U.S. patent application Ser. No. 14/301,087, filed Jun. 10, 2014, which claims the benefit of U.S. Provisional Patent Application No. 61/833,196, filed Jun. 10, 2013. U.S. patent application Ser. No. 14/301,087, filed Jun. 10, 2014, is incorporated herein by reference in its entirety.

FIELD OF THE INVENTION

The present invention provides processes for making 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid ("Compound A" herein) as well as intermediates and processes for making the intermediates. Also provided are crystalline forms of the compound and the intermediates.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors (p53 wildtype). In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p53^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to a compound capable of inhibiting the interaction between p53 and MDM2 and activating p53 downstream effector genes. As such, the compound of the present invention would be useful in the treatment of cancers, bacterial infections, viral infections, ulcers and inflammation. In particular, the compound of the present invention is useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

The compound, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid, having the chemical structure below

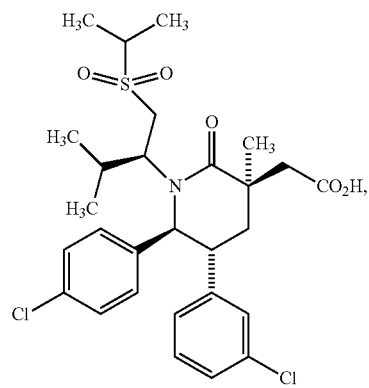 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

is disclosed in published PCT Application No. WO 2011/153,509 (Example No. 362) This compound, a MDM2 inhibitor, is being investigated in human clinical trials for the treatment of various cancers. The present invention provides processes for making the compound as well as intermediates and processes for making the intermediates. Also provided are crystalline forms of the compound and intermediates.

SUMMARY OF THE INVENTION

In embodiment 1, the present invention provides crystalline

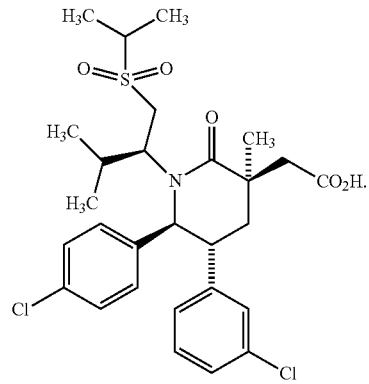 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

In embodiment 2, the present invention provides crystalline anhydrous

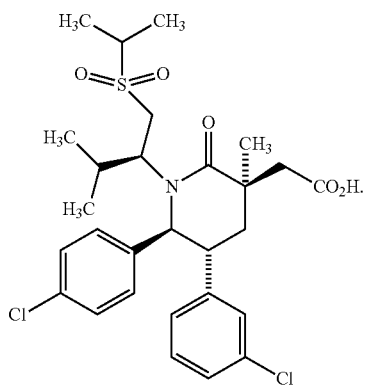 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

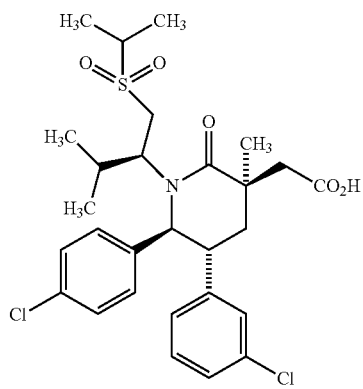 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

In embodiment 3, the present invention provides crystalline anhydrous

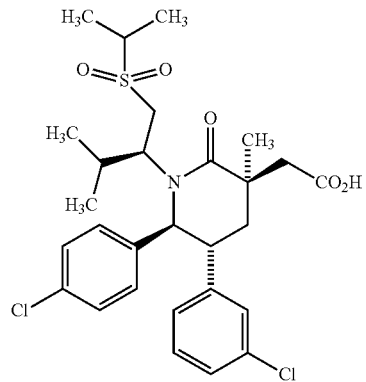 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

characterized by a powder X-ray diffraction pattern comprising peaks at diffraction angle 2 theta degrees at approximately 11.6, 12.4, 18.6, 19.0, 21.6 and 23.6.

In embodiment 4, the present invention provides crystalline anhydrous

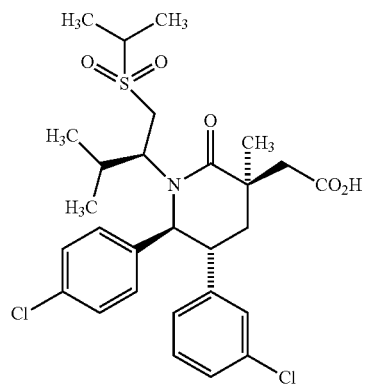 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

in accordance with embodiment 3 having the X-ray diffraction pattern substantially shown in FIG. 1.

In embodiment 5, the present invention provides pharmaceutical compositions comprising: crystalline

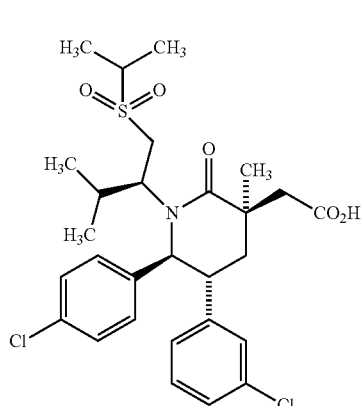

in accordance with any one of embodiments 1 to 4; and a pharmaceutically acceptable excipient.

In embodiment 6, the present invention provides methods of treating bladder cancer, breast cancer, colon cancer, rectal cancer, kidney cancer, liver cancer, small cell lung cancer, non-small-cell lung cancer, esophagus cancer, gall-bladder cancer, ovarian cancer, pancreatic cancer, stomach cancer, cervix cancer, thyroid cancer, prostate cancer, squamous cell carcinoma, melanoma, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute myelogenous leukemia, chronic myelogenous leukemia, endometrial cancer, head and neck cancer, glioblastoma, osteosarcoma, or rhabdomyosarcoma, the methods comprising administering to a patient in need thereof, a therapeutically acceptable amount of a pharmaceutical composition comprising crystalline in accordance with any one of embodiments 1 to 4.

In embodiment 7, the present invention provides the compound

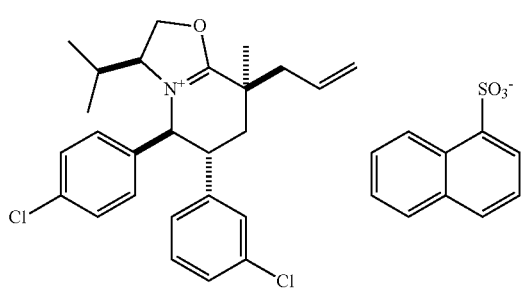

In embodiment 8, the present invention provides the compound

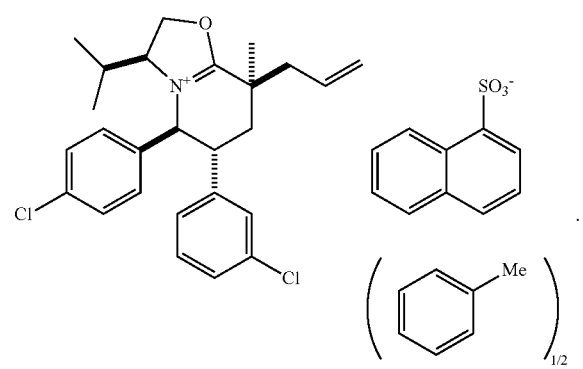

In embodiment 9, the present invention provides crystalline

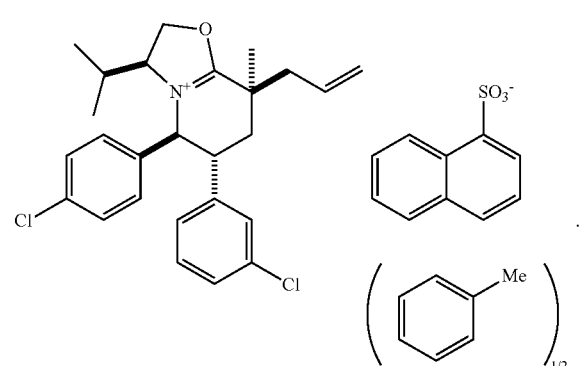

In embodiment 10, the present invention provides crystalline

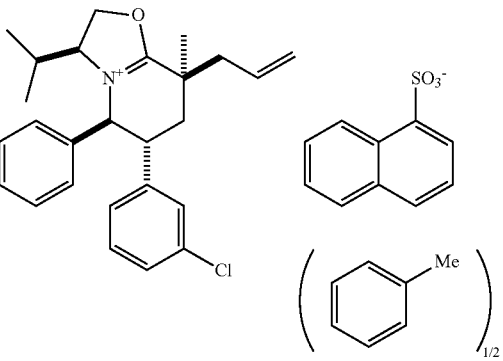

characterized by a powder X-ray diffraction pattern comprising peaks at diffraction angle 2 theta degrees at approximately 8.7, 18.5, 22.6 and 26.6.

In embodiment 11, the present invention provides crystalline

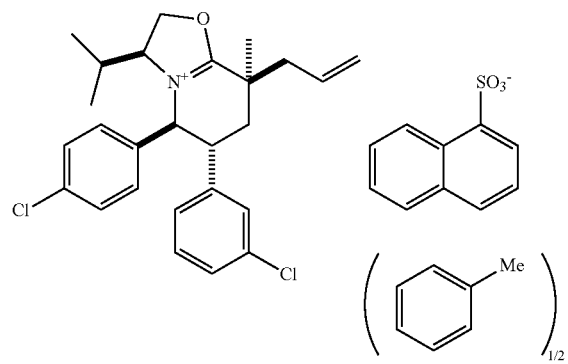

in accordance with embodiment 10 having the X-ray diffraction pattern substantially shown in FIG. 3.

In embodiment 12, the present invention provides the compound

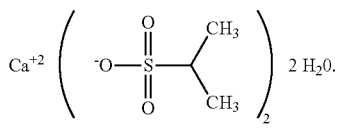

In embodiment 13, the present invention provides a process for making

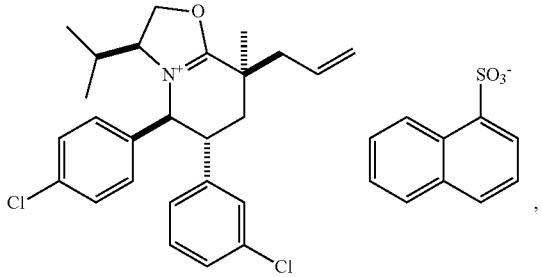

the process comprising:

reacting

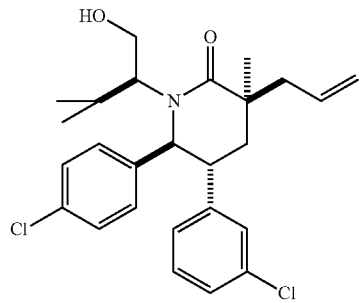

under dehydrating conditions with

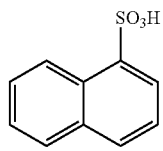

to form

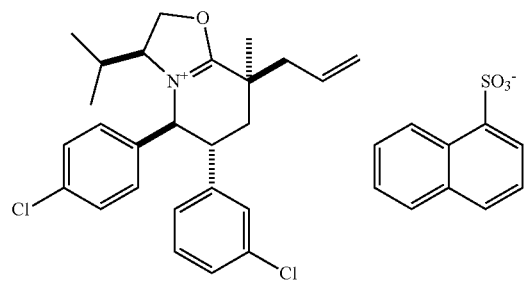

In embodiment 14, the present invention provides the process of embodiment 13 wherein the dehydrating conditions are azeotropic distillation with toluene.

In embodiment 15, the present invention provides a process of making

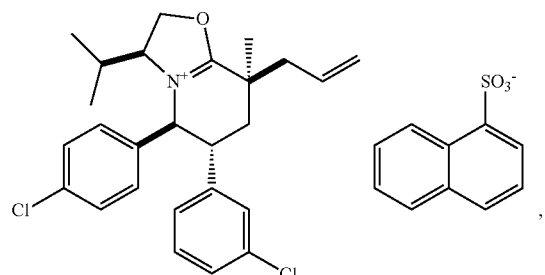

the process comprising:

reacting

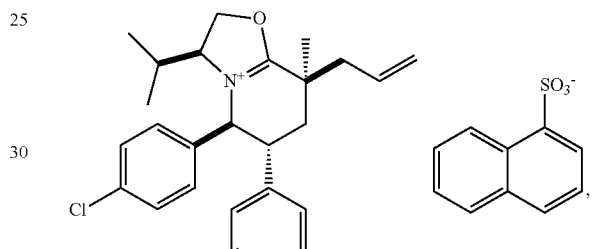

to form

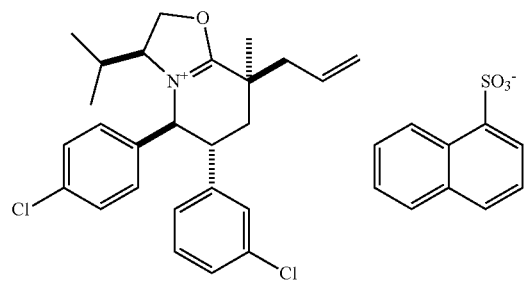

wherein X is $CF_3SO_3^-$ or

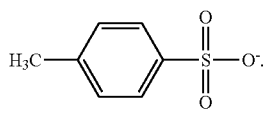

In embodiment 16, the present invention provides a process of making

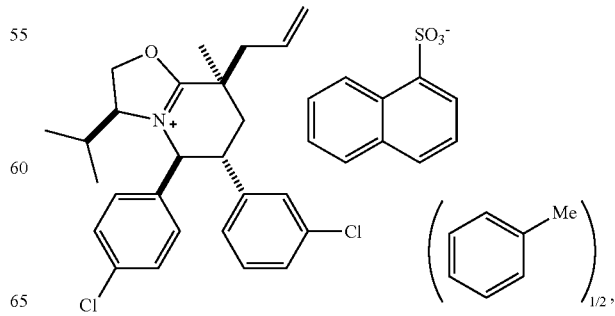

the process comprising:
reacting
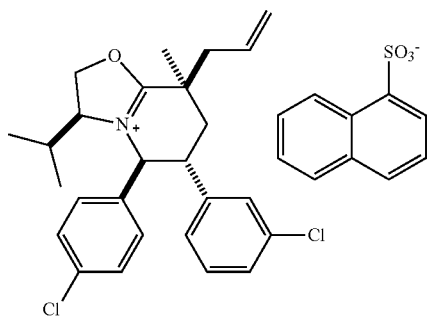
with toluene to form
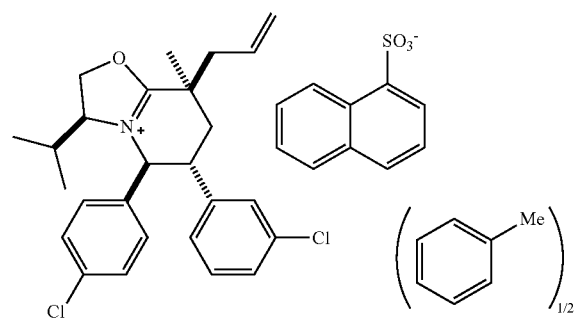
In embodiment 17, the present invention provides a process of making
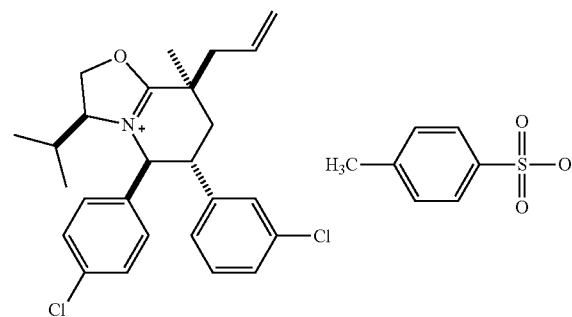
the process comprising:
reacting
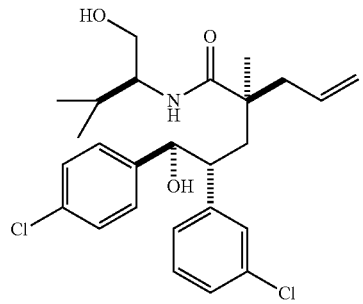
with lutidine and
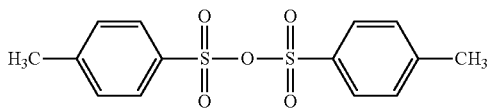
to form
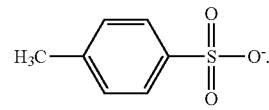
In embodiment 18, the present invention provides a process of making
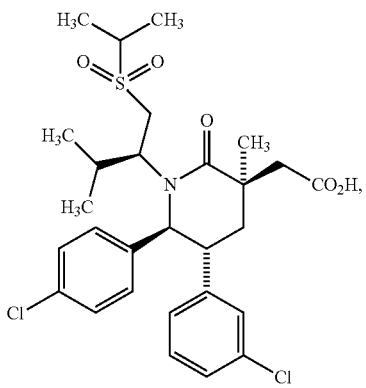 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

the process comprising reacting

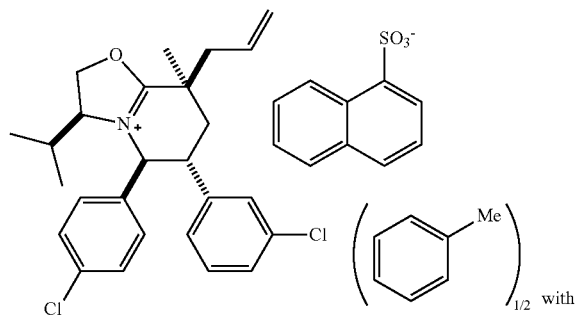

to form

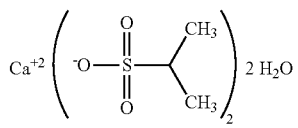

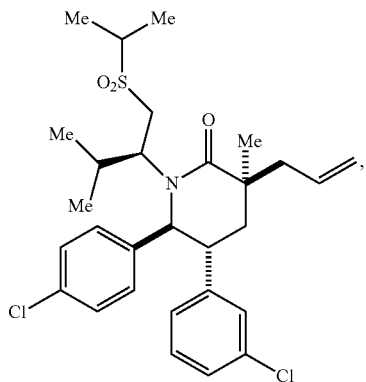

which is oxidized to

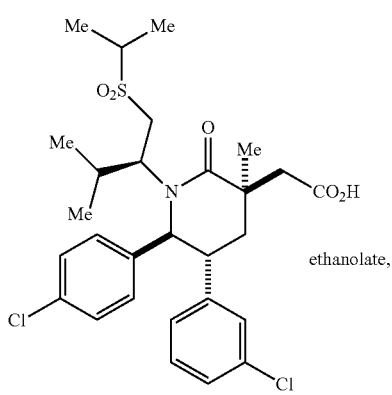

which is further converted to

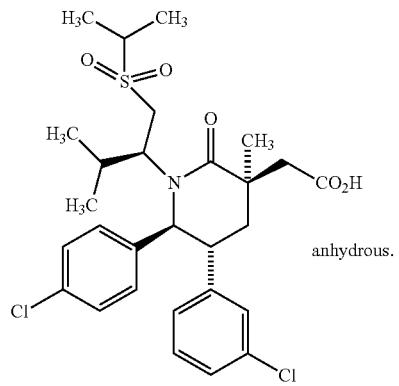 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

anhydrous.

In embodiment 19, the present invention provides a process of embodiment 18 wherein the oxidation is accomplished using ozone.

In embodiment 20, the present invention provides a process of embodiment 18 wherein the oxidation is accomplished using ozone followed by Pinnick oxidation.

In embodiment 21, the present invention provides a process of embodiment 18 wherein the conversion of

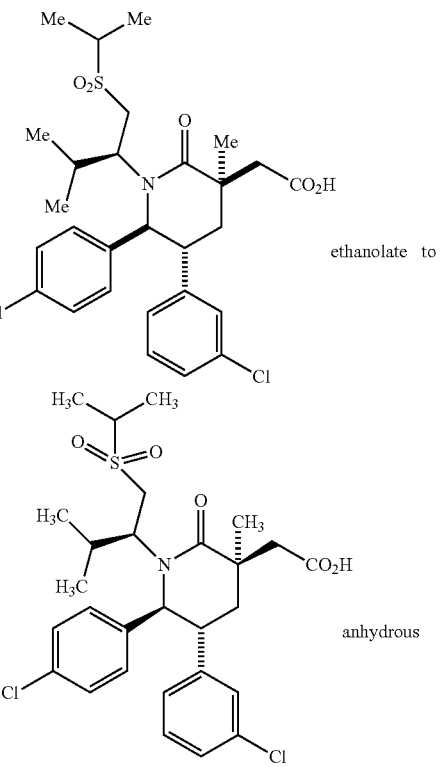

ethanolate to anhydrous is accomplished using methanol and water.

In embodiment 22, the present invention provides a process of embodiment 18 wherein the oxidation is accomplished using ozone followed by Pinnick oxidation, and the conversion of

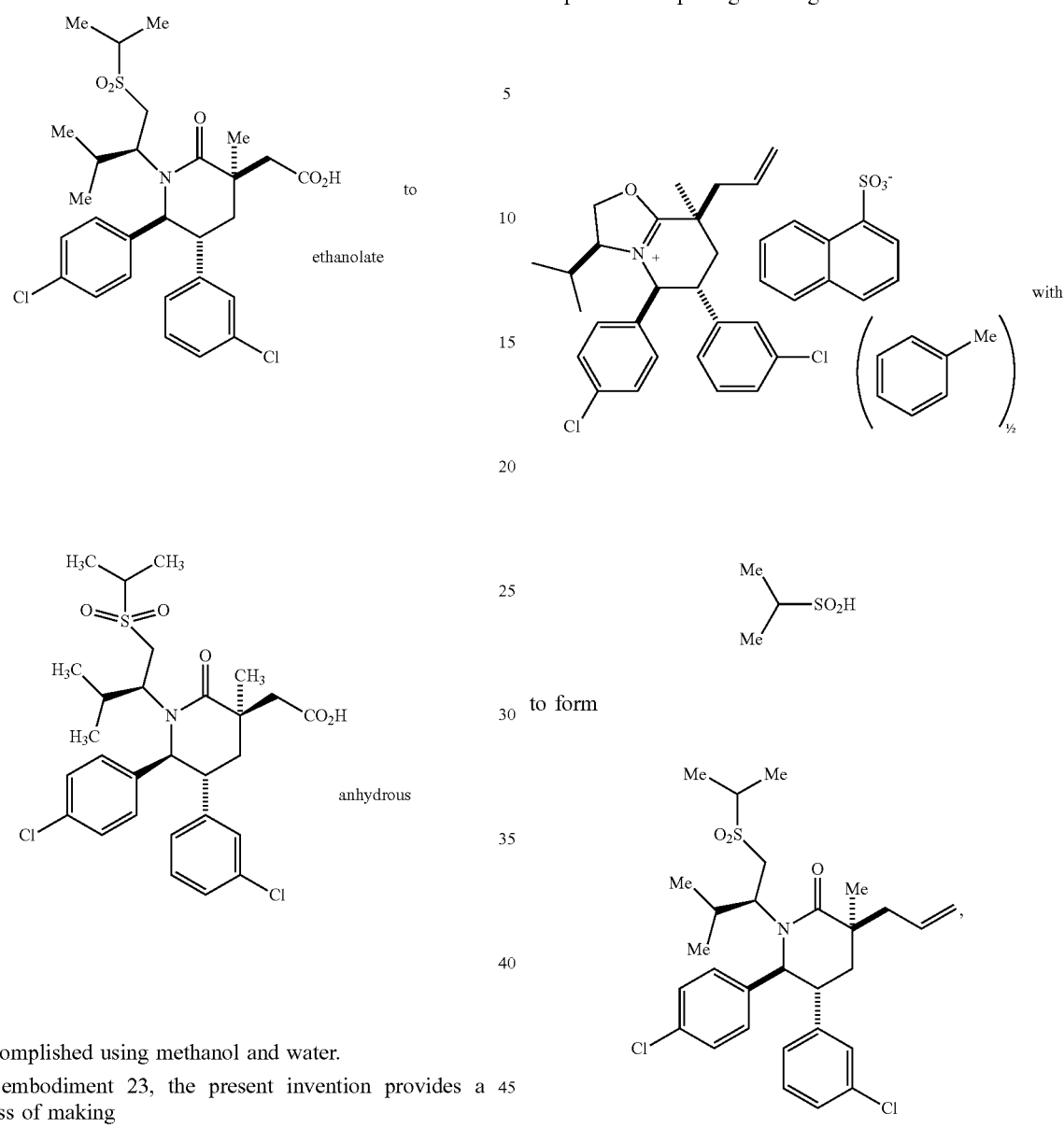
is accomplished using methanol and water.
In embodiment 23, the present invention provides a process of making
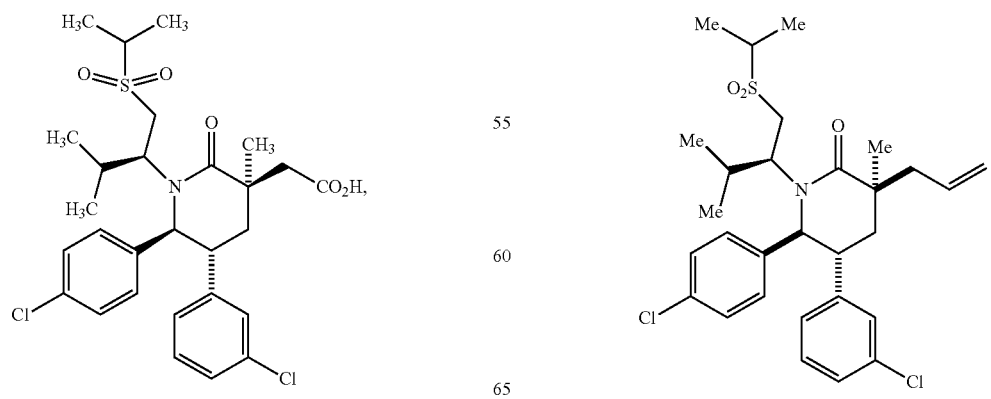

to form

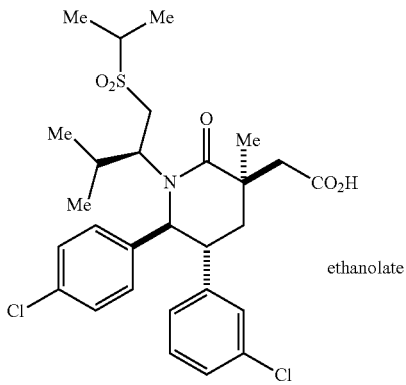

ethanolate which is further converted to

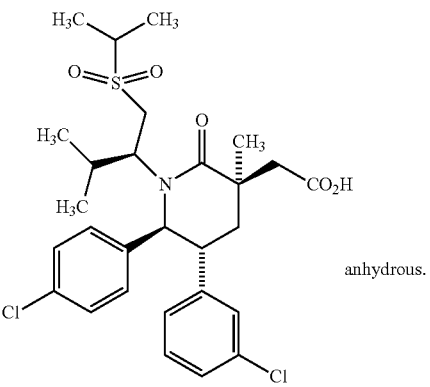 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

anhydrous.

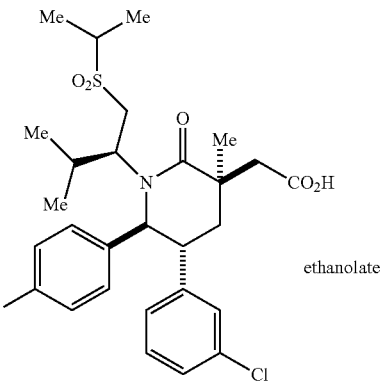

ethanolate

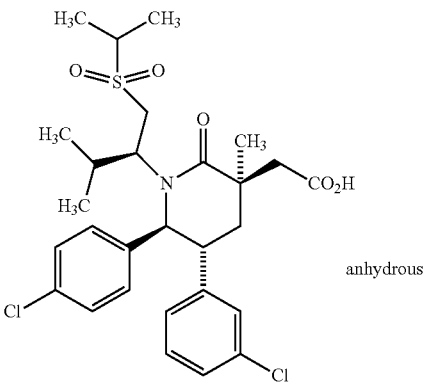

anhydrous

In embodiment 24, the present invention provides a process of embodiment 23 wherein the

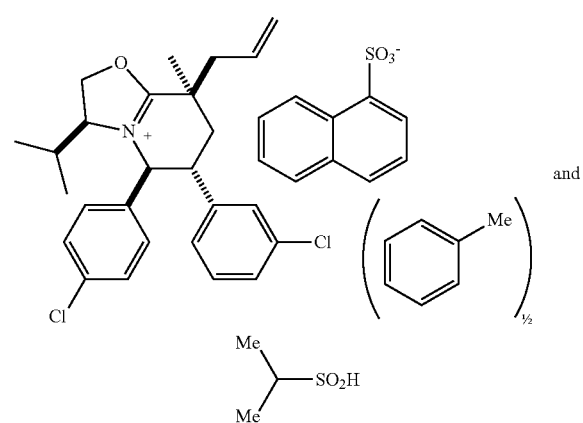

are reacted in the presence of a base.

In embodiment 25, the present invention provides a process of embodiment 24 wherein the base is sodium tert-butoxide.

In embodiment 26, the present invention provides a process of embodiment 23 wherein the oxidation is accomplished using RuCl$_3$ and NaIO$_4$.

In embodiment 27, the present invention provides a process of embodiment 23 wherein the conversion of is accomplished using methanol and water.

In embodiment 28, the present invention provides a process of embodiment 23 wherein the

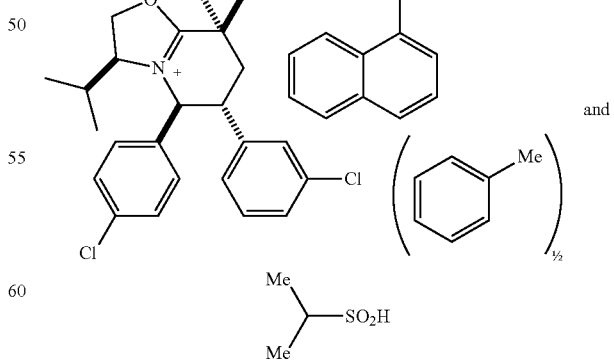

are reacted in the presence of a base;
the oxidation is accomplished using RuCl$_3$ and NaIO$_4$; and
the conversion of

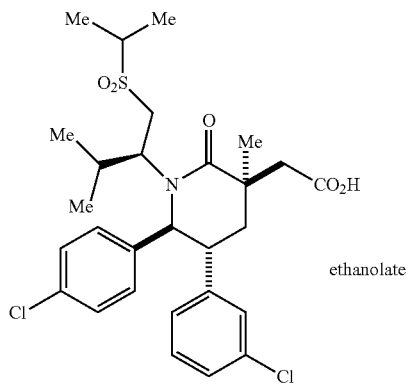

to ethanolate

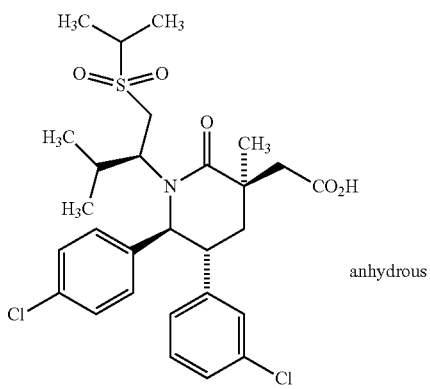

anhydrous is accomplished using methanol and water.

In embodiment 29, the present invention provides the compound

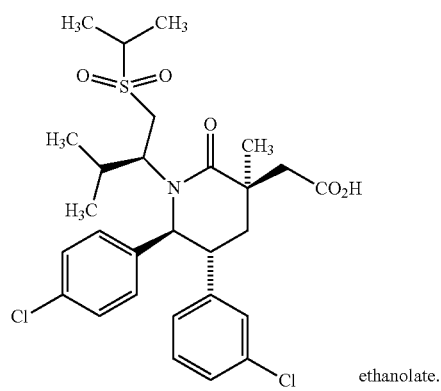 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

ethanolate.

In embodiment 30, the present invention provides crystalline

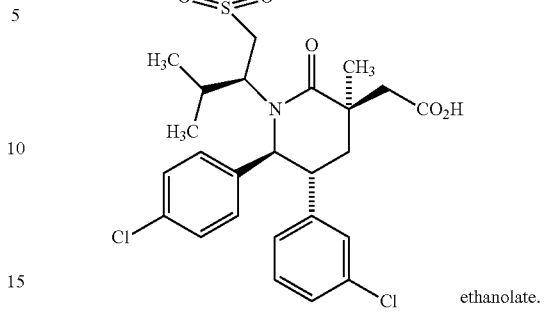

ethanolate.

In embodiment 31, the present invention provides crystalline

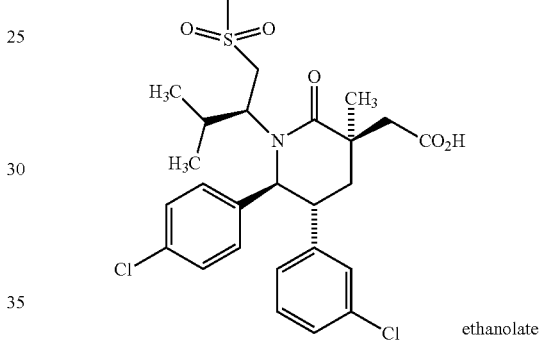

ethanolate characterized by a powder X-ray diffraction pattern comprising peaks at diffraction angle 2 theta degrees at approximately 10.5, 18.2, 20.3, 21, 21.9 and 24.2.

In embodiment 32, the present invention provides crystalline

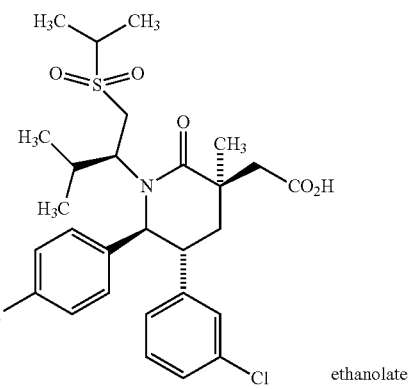

ethanolate in accordance with embodiment 31 having the X-ray diffraction pattern substantially shown in FIG. 6.

In embodiment 33, the present invention provides the compound

In embodiment 34, the present invention provides crystalline

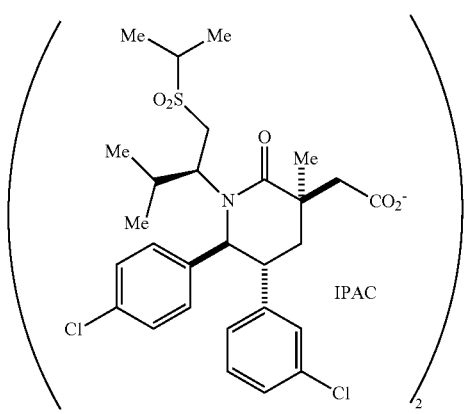

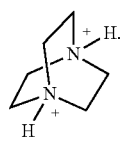

In embodiment 35, the present invention provides crystalline

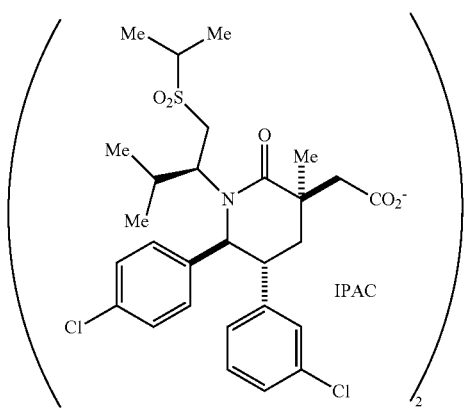

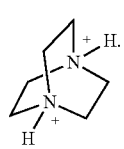

characterized by a powder X-ray diffraction pattern comprising peaks at diffraction angle 2 theta degrees at approximately 11.5, 14.3, 15.8, 17.7, 19.5 and 20.7.

In embodiment 36, the present invention provides crystalline

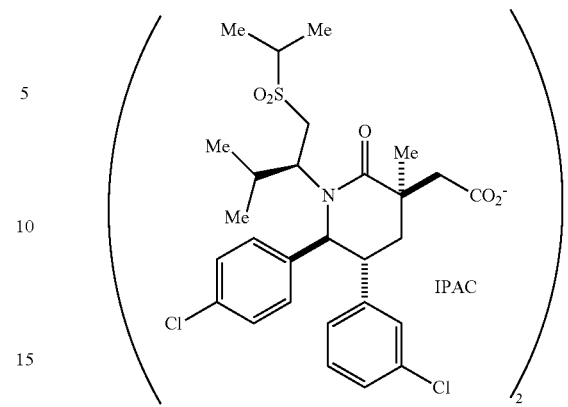

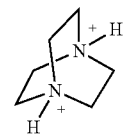

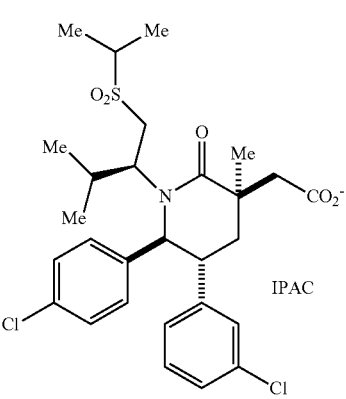

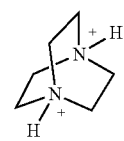

in accordance with embodiment 35 having the X-ray diffraction pattern substantially shown in FIG. 12.

In embodiment 37, the present invention provides a process of making

21

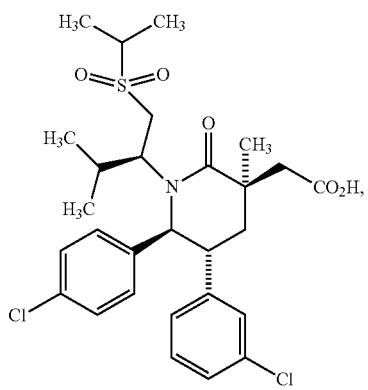 [SMILES: CC(C)[C@@H](CS(=O)(=O)C(C)C)N1C(=O)[C@@](C)(CC(=O)O)C[C@H](c2cccc(Cl)c2)[C@H]1c1ccc(Cl)cc1]

the process comprising reacting

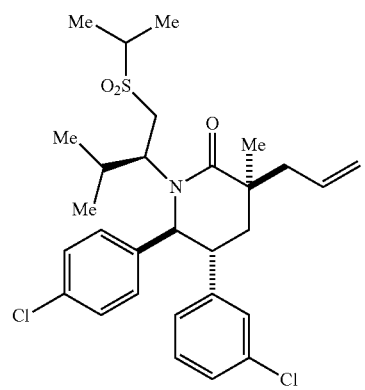

with an oxidizing agent and DABCO to form

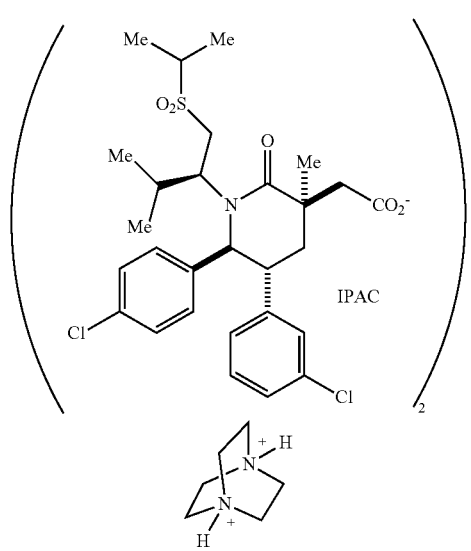

22 and reacting

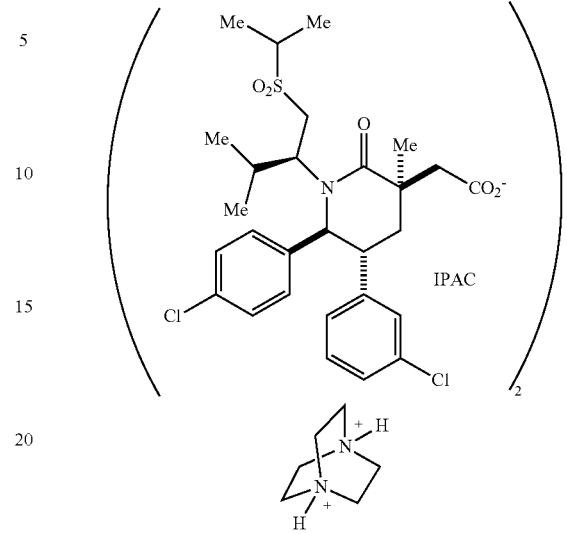

with an acid to form

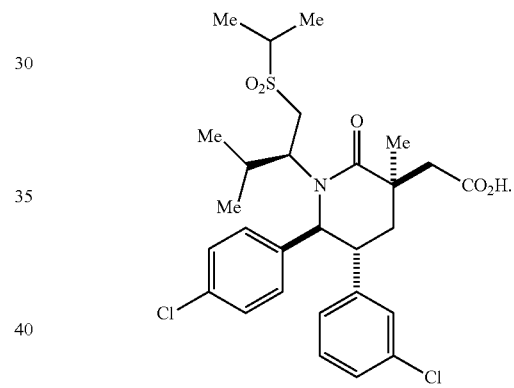

In embodiment 38, the present invention provides the process of embodiment 37 wherein the oxidizing agent is ozone and the acid is hydrochloric acid.

DETAILED DESCRIPTION OF THE INVENTION

Figure 1:
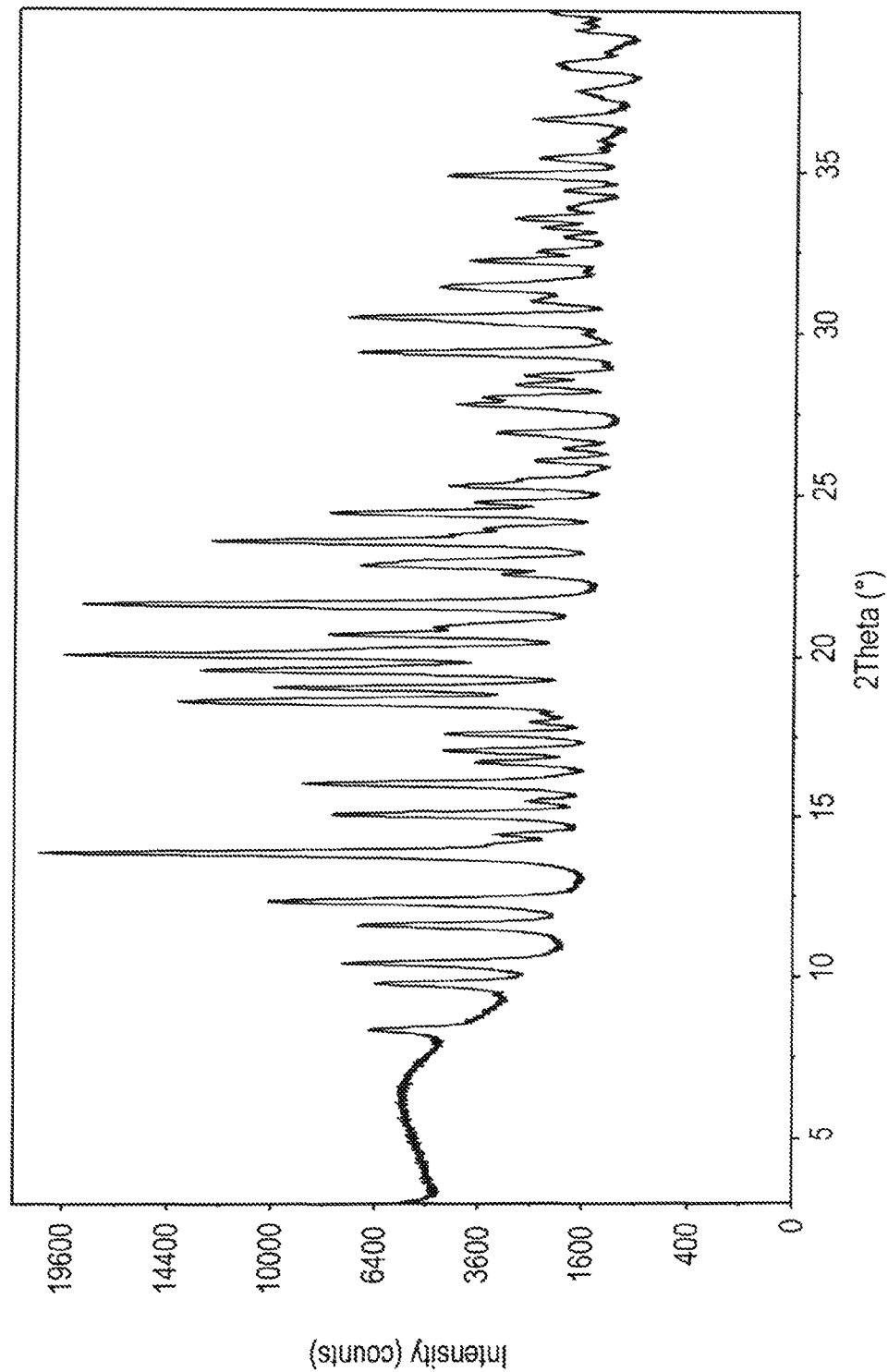
FIG. 1. XRPD Pattern of Compound A Crystalline Anhydrous

The present invention provides processes for making 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid ("Compound A" herein) as well as intermediates and processes for making the intermediates. Also provided are crystalline forms of the compound and the intermediates.

The term "comprising" is meant to be open ended, including the indicated component but not excluding other elements.

The term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of the present invention, or a salt of the compound, or a formulation containing the compound, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compound of the present invention can be administered to a patient in a therapeutically effective amount. The compound can be administered alone or as part of a pharmaceutically acceptable composition or formulation. In addition, the compound or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

The compound of the present invention, or the pharmaceutically acceptable salts thereof, may also be administered in combination with one or more additional pharmaceutically active compounds/agents. It is noted that the additional pharmaceutically active compounds/agents may be a traditional small organic chemical molecules or can be macromolecules such as a proteins, antibodies, peptibodies, DNA, RNA or fragments of such macromolecules.

When a patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compound of the present invention can be used to treat cancer. The methods of treating a cancer comprise administering to a patient in need thereof a therapeutically effective amount of the compound, or a pharmaceutically acceptable salt thereof.

The compound of the present invention can be used to treat tumors. The methods of treating a tumor comprise administering to a patient in need thereof a therapeutically effective amount of the compound, or a pharmaceutically acceptable salt thereof.

The invention also concerns the use of the compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with the compound of the present invention include endometrial cancer, head and neck cancer, glioblastoma, malignant ascites, and hematopoietic cancers.

Particular cancers that can be treated by the compound of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53 wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "p53$^{WT}$" means a protein encoded by genomic DNA sequence no. NC_000017 version 9 (7512445 . . . 7531642)(GenBank); a protein encoded by cDNA sequence no. NM_000546 (GenBank); or a protein having the GenBank sequence no. NP_000537.3. The term "CDNK2A mutant" means a CDNK2A protein that is not wildtype. The term "CDKN2A wildtype" means a protein encoded by genomic DNA sequence no. 9:21957751-21984490 (Ensembl ID); a protein encoded by cDNA sequence no. NM_000077 (GenBank) or NM_058195 9GenBank) or; or a protein having the GenBank sequence no. NP_000068 or NP_478102.

In another aspect, the present invention relates to the use of the compound of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compounds inhibit one or more isoform more than other isoforms. Selectivity is a concept well known to those in the art and can be measured with well known activity in in vitro or cell-based assays. Preferred selectivity includes greater than 2-fold, preferably 10-fold, or more preferably 100-fold greater selectivity for one or more isoform over the other isoforms. In one aspect, the PI3K inhibitors that can be used in combination with compounds of the present invention is a PI3K a selective inhibitor. In another aspect the compound is a PI3K δ selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Compounds that inhibit both PI3K and mTOR (dual inhibitors) are known. In still another aspect, the present invention provides the use of dual PI3K and mTOR inhibitors for use in combination with the compound of the present invention.

mTOR is a protein in the PI3K pathway. It is another aspect of the present invention to use an mTOR inhibitor in combination with the compound of the present invention. mTOR inhibitors that can be used in combination with the compound of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with the compound of the present invention. PKB inhibitors that can be used in combination with the compound of the present invention include those disclosed in the following documents: U.S. Pat. No. 7,354,944; U.S. Pat. No. 7,700,636; U.S. Pat. No. 7,919,514; U.S. Pat. No. 7,514,566; U.S. patent application publication no. US 2009/0270445 A1; U.S. Pat. No. 7,919,504; U.S. Pat. No. 7,897,619; or PCT published application no. WO 2010/083246 A1.

The combinations of the present invention may also be used in conjunction with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents. In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compound of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of the compound of the present invention include ointments, powders, sprays and inhalants. The active compound or compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compound of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compound of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compound of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compound of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compound of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. To illustrate, because the compound of the invention contains a carboxylic acid functional group, a prodrug can comprise an ester formed by the replacement of the hydrogen atom of the carboxylic acid group with a group such as ($C_1$-$C_8$ alkyl, ($C_2$—$Cl_2$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_{2-3}$)alkyl.

The compound of the present invention may contain asymmetric or chiral centers, and therefore, exist in different stereoisomeric forms. It is contemplated that all stereoisomeric forms of the compound as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compound of the present invention may exist in unsolvated as well as solvated forms with pharmaceutically acceptable solvents such as water (hydrate), ethanol, and the like. The present invention contemplates and encompasses both the solvated and unsolvated forms as set forth herein.

It is also possible that the compound of the present invention may exist in different tautomeric forms. All tautomers of the compound of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{18}$O, $^{31}$P, $^{32}$P, $^{35}$S, $^{18}$F, and $^{36}$Cl. In one aspect, the present invention relates to compounds wherein one or more hydrogen atom is replaced with deuterium ($^2$H) atoms.

The compound of the present invention that contains the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

The compound of the present invention may exist in various solid states including crystalline states and as an amorphous state. The different crystalline states, also called polymorphs, and the amorphous states of the present compounds are contemplated as part of this invention as set forth herein.

In synthesizing the compound of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The specific experimental examples presented in this application illustrate specific embodiments of the present invention. These examples are meant to be representative and are not intended to limit the scope of the claims in any manner.

$^1$H-NMR spectra were typically acquired on a Bruker Avance III 500 spectrometer system (Bruker, Billerica, Mass.) operating at a $^1$H frequency of 500.13 MHz, equipped with a Bruker 5 mm PABBI probe with a z-axis gradient; or on a Bruker Avance II or Avance III 400 spectrometer operating at a $^1$H frequency of 400.23 MHz, equipped with a Bruker 5 mm PABBO probe with a z-axis gradient. Samples were typically dissolved in 500 μL of either DMSO-$d_6$ or $CD_3OD$ for NMR analysis. $^1$H chemical shifts are referenced to the residual solvent signals from DMSO-$d_6$ at δ 2.50 and $CD_3OD$ at δ 3.30.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz. Electron Ionization (EI) mass spectra were typically recorded on an Agilent Technologies 6140 Quadrupole LC/MS mass spectrometer (Agilent Technologies, Englewood, Colo.). Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

X-Ray powder diffraction data (XRPD) were obtained using a PANalytical X'Pert PRO diffractometer (PANalytical, Almelo, The Netherlands) fitted with a real time multiple strip (RTMS) detector. The radiation used was CuKα(1.54 Å) and the voltage and current were set at 45 kV and 40 mA, respectively. Data were collected at room temperature from 5 to 45 degrees 2-theta with a step size of 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα(1.54 Å) and the voltage and current were set at 45 kV and 40 mA, respectively. Data were collected at room temperature from 5 to 40, degrees 2-theta with a step size of either 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα(1.54 Å) and the voltage and current were set at 45 kV and 40 mA, respectively. Data were collected at room temperature from 5 to 40, degrees 2-theta with a step size of either 0.0167 degrees. Samples were prepared on a low background sample holder and placed on the sample stage which was rotated with a 2 second revolution time.

Alternatively, XRPD data were obtained using a PANalytical X'Pert Pro diffractometer (PANalytical, Almelo, The Netherlands) fitted with a RTMS detector. The radiation used was CuKα(1.54 Å) and the voltage and current were set at 45 kV and 40 mA, respectively. Data were collected at room temperature from 3 to 40, degrees 2-theta with a step size of 0.008 degrees. Samples were prepared on a low background sample holder and placed on the sample stage with a 2 second revolution time.

Alternatively, XRPD data were obtained using a Bruker D8 Discover X-ray diffraction system (Bruker, Billerica, Mass.) fitted with a motorized xyz sample stage and a GADDS area detector. The radiation used was CuKα(1.54 Å) and the voltage and current were set at 45 kV and 40 mA, respectively. The solid samples on a flat glass plate were mapped and for each sample an area of 1 mm$^2$ was scanned in an oscillating mode for 3 minutes from 5 to 48 degrees 2-theta.

Differential Scanning calorimetry (DSC) data was collected using standard DSC mode (DSC Q200, TA Instruments, New Castle, Del.). A heating rate of 10° C./min was employed over a temperature range from 40° C. to 300° C. Analysis was run under nitrogen and samples were loaded in standard, hermetically-sealed aluminum pans. Indium was used as a calibration standard.

Alternatively, DSC data were collected using temperature-modulated DSC mode (DSC Q200, TA Instruments, New Castle, Del.). After sample equilibration at 20° C. for five minutes, the heating rate of 3° C./min was employed with a modulation of +/−0.75° C./min over a temperature range from 20° C. to 200° C. Analysis was run under nitrogen and samples were loaded in standard, uncrimped aluminum pans. Indium was used as a calibration standard.

The following abbreviations may be used herein.

~ about
+ve or pos. ion positive ion
Δ heat
Ac acetyl
ACN acetonitrile
$Ac_2O$ acetic anhydride
aq aqueous
AcOH acetic acid
Bn benzyl
Boc tert-butyloxycarbonyl
BSA bovine serum albumin
Bu butyl
Bz benzoyl
Calcd or Calc'd calculated
$Ca(OH)_2$ calcium hydroxide
$CH_3OK$ potassium methoxide
$CH_3ONa$ sodium methoxide
Conc. concentrated d day(s)
DABCO 1,4-diazabicyclo[2.2.2]octane
DCE dichloroethane
DCM dichloromethane
DEA diethylamine
Dess-Martin periodinane; 1,1,1-triacetoxy-1,1-dihydro-1,2-benziodoxol-3-(1H)-one
Dess-Martin reagent
DIEA or DIPEA diisopropylethylamine
DMAP 4-dimethylaminopyridine
DME 1,2-dimethoxyethane
DMF N,N-dimethylformamide
DMSO dimethyl sulfoxide
DPPA diphenylphosphoryl azide
dr or DR diastereomeric ratio
DSC differential scanning calorimetry
DTT dithiothreitol
DVB divinylbenzene
EDC N-ethyl-N'-(3-dimethylaminopropyl)carbodiimide
ee or e.e. enantiomeric excess
eq equivalent
ESI or ES electrospray ionization
Et ethyl
Et$_2$O diethyl ether
Et$_3$N triethylamine
EtOAc ethyl acetate
EtOH ethyl alcohol
g gram(s)
h hour(s)
HATU O-(7-azabenzotriazol-1-yl)-N,N,N',N'-tetramethyl-uronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HPLC high pressure liquid chromatography
IPAc or IPAC isopropyl acetate
IPA or iPrOH isopropyl alcohol
iPr isopropyl
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol L$^{-1}$)
mCPBA m-chloroperoxybenzoic acid
mDSC modulated differential scanning calorimetry
Me methyl
MeCN acetonitrile
MeI iodomethane
MEK methyl ethyl ketone
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB paramethoxybenzyl
Ph phenyl
Pr propyl
ppm parts per million
PTFE polytetrafluoroethylene
p-tol para-toluoyl
rac racemic
RP-HPLC or RPHPLC reversed phase high pressure liquid chromatography
RT or rt or r.t. room temperature
sat. or sat'd or satd saturated
SFC supercritical fluid chromatography
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA trifluoroacetic acid
TGA thermogravimetric analysis
THF tetrahydrofuran
TIPS triisopropylsilyl
TLC thin layer chromatography
TMS trimethylsilyl or trimethylsilane
TPAP tetrapropylammonium perruthenate
t$_R$ retention time
TRIS 2-amino-2-hydroxymethyl-propane-1,3-diol
TfOH trifluoroacetic acid
TfO$^-$ trifluoroacetate
Tf$_2$O trifluoroacetic acid anhydride
TsOH or PTSA p-toluenesulfonic acid
TsO$^-$ p-toluenesulfonate
Ts$_2$O p-toluenesulfonic acid anhydride
tBuOH tert-butyl alcohol
XRD X-ray diffraction
XRPD or PXRD X-ray powder diffraction
v/v volume per volume
Procedures to Make Certain Intermediates and Starting Materials
Method for Making

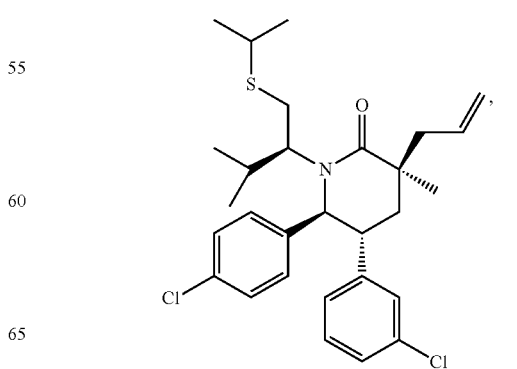

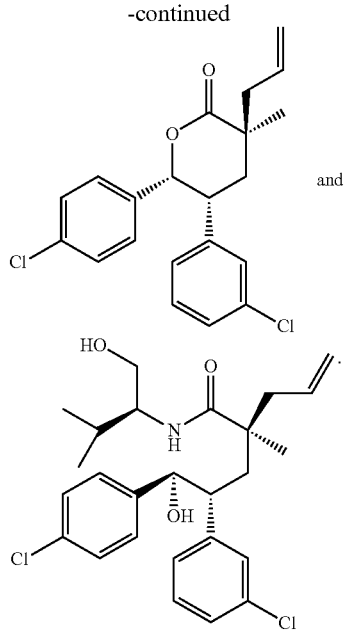

Step A.
2-(3-Chlorophenyl)-1-(4-chlorophenyl)ethanone

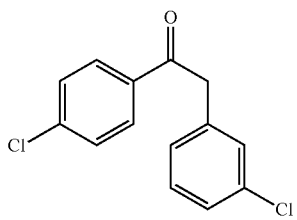 [SMILES: O=C(Cc1cccc(Cl)c1)c1ccc(Cl)cc1]

Sodium bis(trimethylsilyl)amide (1 M in tetrahydrofuran, 117 mL) was slowly added to a −78° C. solution of 2-(3-chlorophenyl) acetic acid (10 g, 58.6 mmol) in tetrahydrofuran (58 mL) over 1 hour. After stirring at −78° C. for 40 minutes, a solution of methyl 4-chlorobenzoate (10 g, 58.6 mmol) in tetrahydrofuran (35 mL) was added over a period of 10 minutes. The reaction was stirred at −78° C. for 3 hours then allowed to warm to 25° C. After two hours at 25° C., the reaction was quenched with saturated aqueous ammonium chloride solution, and most of the tetrahydrofuran was removed under reduced pressure. The residue was extracted with ethyl acetate (2×100 mL). The combined organic layers were washed with saturated sodium chloride solution, dried over sodium sulfate, filtered and the filtrate was concentrated. The product was recrystallized from ether/pentane to provide the title compound as a white solid.

Alternative Procedure

To a mixture of chlorobenzene (170 L, 1684 mol), 3-chlorophenylacetic acid (50 Kg, 293 mol), and dimethylformamide (0.7 L, 9 mol) at 0° C. was added thionyl chloride (39.1 Kg, 329 mol) over the course of 30 min. The mixture was warmed to 15° C. and agitated for 6 h. The mixture was cooled to 0° C. and aluminum chloride (43 Kg, 322 mol) was added over the course of 1.5 h. The mixture was warmed to 20° C. and agitated for 15 h. Water (200 L) and ethanol (200 L) were added to the mixture and the biphasic mixture was agitated for 2 h. The phases were separated and the organic phase was washed twice with aqueous ethylenediaminetetraacetic acid tetrasodium salt (3 wt %, 200 L), and once with water (200 L). Heptane (1600 L) was added to the organic phases over the course of 15 minutes. The suspension was agitated for 30 minutes, cooled to −5° C., and filtered. The filtered material was dried at 40° C. for 20 h. 2-(3-Chlorophenyl)-1-(4-chlorophenyl)ethanone was isolated in 83.6% yield (67.4 Kg).

$^{1}$H NMR (500 MHz, DMSO-d$_6$, δ ppm): 8.05 (m, 2H), 7.62 (m, 2H), 7.33 (m, 3H), 7.21 (br d, J=7.3 Hz, 1H), 4.45 (s, 2H). MS (ESI)=265.1 [M+H]$^{+}$.

Step B: Methyl 4-(3-chlorophenyl)-5-(4-chlorophenyl)-2-methyl-5-oxopentanoate

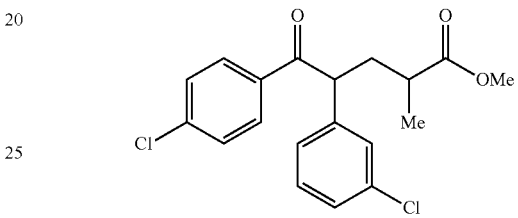

Methyl methacrylate (12.65 mL, 119 mmol) was added to a solution of 2-(3-chlorophenyl)-1-(4-chlorophenyl)ethanone (30 g, 113 mmol) in tetrahydrofuran (283 mL). Potassium tert-butoxide (1.27 g, 11.3 mmol) was then added and the reaction was stirred at room temperature for 2 days. The solvent was removed under a vacuum and replaced with 300 mL of ethyl acetate. The organic phase was washed with brine (50 mL), water (3×50 mL), and brine (50 mL). The organic phase was dried over magnesium sulfate, filtered and concentrated under a vacuum to afford methyl 4-(3-chlorophenyl)-5-(4-chlorophenyl)-2-methyl-5-oxopentanoate as an approximately 1:1 mixture of diastereomers.

$^{1}$H NMR (400 MHz, CDCl$_3$, δ ppm): 7.87 (m, 2H), 7.38 (m, 2H), 7.27-7.14 (series of m, 4H), 4.61 (m, 1H), 3.69 (s, 1.5H), 3.60 (s, 1.5H), 2.45 (m, 1H), 2.34 (m, 1H), 2.10 (ddd, J=13.9, 9.4, 5.5 Hz, 0.5H), 1.96 (ddd, J=13.7, 9.0, 4.3 Hz, 0.5H), 1.22 (d, J=7.0 Hz, 1.5H), 1.16 (d, J=7.0, 1.5H). MS (ESI)=387.0 [M+23]$^{+}$.

Step C: (3S,5R,6R)-5-(3-Chlorophenyl)-6-(4-chlorophenyl)-3-methyltetrahydro-2H-pyran-2-one and (3R,5R,6R)-5-(3-chlorophenyl)-6-(4-chlorophenyl)-3-methyltetrahydro-2H-pyran-2-one

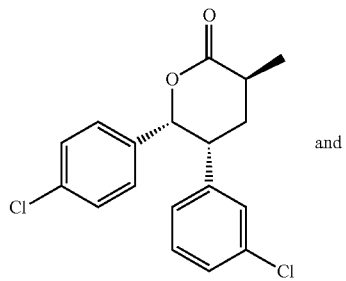

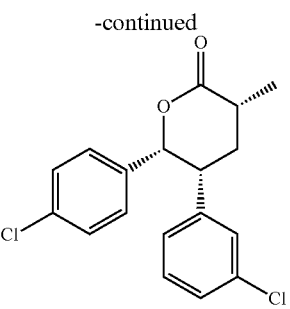

Methyl 4-(3-chlorophenyl)-5-(4-chlorophenyl)-2-methyl-5-oxopentanoate (40 g, 104.0 mmol) was dissolved in 200 mL of anhydrous toluene and concentrated under a vacuum. The residue was placed under high vacuum for 2 hours before use. The compound was split into 2×20 g batches and processed as follows: methyl 4-(3-chlorophenyl)-5-(4-chlorophenyl)-2-methyl-5-oxopentanoate (20 g, 52.0 mmol) in anhydrous 2-propanol (104 mL) was treated with potassium tert-butoxide (2.33 g, 20.8 mmol) in a 250 mL glass hydrogenation vessel. RuCl$_2$(S-xylbinap)(S-DAIPEN) (0.191 g, 0.156 mmol, Strem Chemicals, Inc., Newburyport, Mass.) in 3.8 mL of toluene was added. After 1.5 hours, the vessel was pressurized to 50 psi (344.7 kPa) and purged with hydrogen five times and allowed to stir at room temperature. The reaction was recharged with additional hydrogen as needed. After 3 days, the reactions were combined and partitioned between 50% saturated ammonium chloride solution and ethyl acetate. The aqueous layer was extracted with ethyl acetate. The combined organic phases were washed with brine, dried over magnesium sulfate, filtered, and concentrated.

The crude product (predominantly, (4R,5R)-isopropyl 4-(3-chlorophenyl)-5-(4-chlorophenyl)-5-hydroxy-2-methylpentanoate) was dissolved in tetrahydrofuran (450 mL) and methanol (150 mL). Lithium hydroxide (1.4 M, 149 mL, 208 mmol) was added, and the solution was stirred at room temperature for 24 hours. The mixture was concentrated under a vacuum and the residue was redissolved in ethyl acetate. Aqueous 1N hydrochloric acid was added with stirring until the aqueous layer had a pH of about 1. The layers were separated and the organic phase was washed with brine, dried over magnesium sulfate, filtered and concentrated. The material was dissolved in 200 mL of anhydrous toluene and treated with pyridinium p-toluenesulfonate (PPTS, 0.784 g, 3.12 mmol). The reaction was heated to reflux under Dean-Stark conditions until the seco-acid was consumed (about 2 hours). The reaction was cooled to room temperature and washed with saturated sodium bicarbonate (50 mL) and brine (50 mL). The solution was dried over sodium sulfate, filtered and concentrated. The crude material was purified by flash chromatography on silica gel (120 g column; eluting with 100% dichloromethane). The title compounds were obtained as a white solid with an approximate 94:6 enantiomeric ratio and a 7:3 mixture of methyl diastereomers.

$^1$H NMR (400 MHz, CDCl$_3$, δ ppm): 7.22-6.98 (series of m, 5H), 6.91 (dt, J=7.4, 1.2 Hz, 0.3H), 6.81 (m, 2H), 6.73 (dt, J=7.6, 1.4 Hz, 0.7H), 5.76 (d, J=4.1 Hz, 0.3H), 5.69 (d, J=4.7 Hz, 0.7H), 3.67 (dt, J=6.6, 4.3 Hz, 0.3H), 3.55 (td, J=7.8, 4.7 Hz, 0.7H), 2.96 (d of quintets, J=13.5, 6.7 Hz, 0.7H), 2.81 (m, 0.3H), 2.56 (dt, J=14.3, 8.0 Hz, 0.7H), 2.32 (dt, J=13.69, 7.0 Hz, 0.3H), 2.06 (ddd, J=13.7, 8.4, 4.1, 0.3H), 1.85 (ddd, J=14.1, 12.5, 7.4, 0.7H), 1.42 (d, J=7.0 Hz, 0.9H), 1.41 (d, J=6.7 Hz, 2.1H). MS (ESI)=357.0 [M+23]$^+$. [α]$_D$ (22° C., c=1.0, CH$_2$Cl$_2$)=−31.9°; m.p. 98-99° C.

Step D. (3S,5R,6R)-3-Allyl-5-(3-chlorophenyl)-6-(4-chlorophenyl)-3-methyltetrahydro-2H-pyran-2-one

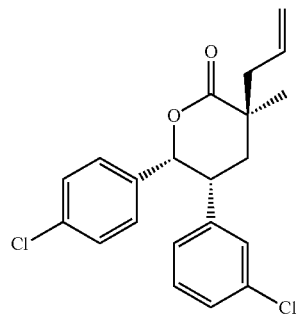 [SMILES: C=CC[C@@]1(C)C[C@H](c2cccc(Cl)c2)[C@H](c2ccc(Cl)cc2)OC1=O]

A solution of (3S,5R,6R)-5-(3-chlorophenyl)-6-(4-chlorophenyl)-3-methyltetrahydro-2H-pyran-2-one and (3R,5S,6S)-5-(3-chlorophenyl)-6-(4-chlorophenyl)-3-methyltetrahydro-2H-pyran-2-one (4.5 g, 13.4 mmol) and allyl bromide (3.48 mL, 40.3 mmol) in tetrahydrofuran (22 mL) at −35° C. (acetonitrile/dry ice bath) was treated with a solution of lithium bis(trimethylsilyl)amide in tetrahydrofuran (1.0 M, 17.45 mL, 17.45 mmol). The reaction was allowed to warm to −5° C. over 1 hour and then was quenched with 50% saturated ammonium chloride. The reaction was diluted with 100 mL of ethyl acetate and the layers were separated. The organic phase was washed with brine, dried over magnesium sulfate, filtered and concentrated under a vacuum to afford the title compound as a white solid upon standing under a vacuum. Chiral SFC (92% CO$_2$, 8% methanol (20 mM ammonia), 5 mL/min, Phenomenex Lux-2 column (Phenomenex, Torrance, Calif.), 100 bar (10,000 kPa), 40° C., 5 minute method) was used to determine that the compound had an enantiomeric ratio of 96:4. (Major enantiomer: title compound, retention time=2.45 minutes, 96%; minor enantiomer (structure not shown, retention time=2.12 min, 4%). The title compound was recrystallized by adding to heptane (4.7 g slurried in 40 mL) at reflux and 1.5 mL of toluene was added dropwise to solubilize. The solution was cooled to 0° C. The white solid was filtered and rinsed with 20 mL of cold heptanes to afford a white powder. Chiral SFC (92% CO$_2$, 8% methanol, Phenomenex Lux-2 column, same method as above) indicated an enantiomeric ratio of 99.2:0.8. (major enantiomer, 2.45 min, 99.2%; minor enantiomer: 2.12 min, 0.8%)

$^1$H NMR (400 MHz, CDCl$_3$, δ ppm): 7.24 (ddd, J=8.0, 2.0, 1.2 Hz, 1H), 7.20-7.15 (series of m, 3H), 6.91 (t, J=2.0 Hz, 1H), 6.78 (br d, J=7.6 Hz, 1H), 6.60 (m, 2H), 5.84 (ddt, J=17.6, 10.2, 7.4 Hz, 1H), 5.70 (d, J=5.3 Hz, 1H), 5.21-5.13 (series of m, 2H), 3.82 (dt, J=11.7, 4.5 Hz, 1H), 2.62 (ABX J$_{AB}$=13.7 Hz, J$_{AX}$=7.6 Hz, 1H), 2.53 (ABX, J$_{AB}$=13.9 Hz, J$_{BX}$=7.2 Hz, 1H). 1.99 (dd, J=14.1, 11.9 Hz, 1H), 1.92 (ddd, J=13.9, 3.9, 1.2 Hz, 1H). $^{13}$C NMR (CDCl$_3$, 100 MHz, δ ppm): 175.9, 140.2, 134.5, 134.3, 134.0, 132.2, 129.8, 128.6, 128.0, 127.9, 127.8, 126.4, 119.9, 83.9, 44.5, 42.4, 40.7, 31.8, 26.1. MS (ESI)=375.2 [M+H]$^+$. IR=1730 cm$^{-1}$. [α]$_D$ (24° C., c=1.0, CH$_2$Cl$_2$)=−191°. m.p. 111-114° C.

Alternative route to make (3S,5R,6R)-3-allyl-5-(3-chlorophenyl)-6-(4-chlorophenyl)-3-methyltetrahydro-2H-pyran-2-one Step 1: Isopropyl 4-(3-chlorophenyl)-5-(4-chlorophenyl)-2-methyl-5-oxopentanoate

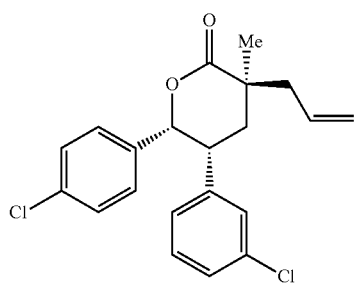 [SMILES: C=CC[C@@]1(C)C[C@H](c2cccc(Cl)c2)[C@H](c2ccc(Cl)cc2)OC1=O]

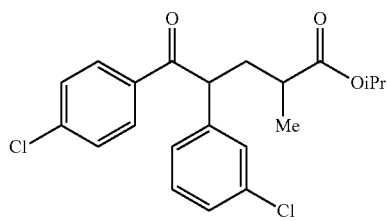

A solution of 2-(3-chlorophenyl)-1-(4-chlorophenyl)ethanone (Step A) (67.4 Kg, 255 mol) in THF (325 L) was dried azeotropically to achieve a water content by Karl Fisher of 0.05 wt %. Methyl methacrylate (25.8 Kg, 257 mol) was added to the solution and the mixture was heated to 45° C. A solution of potassium tert-butoxide (20 wt % in THF, 14.3 Kg, 25 mol) was added over the course of 30 minutes and the mixture was agitated for 6 h. The mixture was cooled to 10° C. and an aqueous solution of citric acid monohydrate (20 wt %, 35 L) was added in less than 5 minutes. Isopropyl acetate (400 L) and an aqueous sodium chloride solution (20 wt %, 300 L) were added. The mixture was agitated for 15 minutes and the phases were separated. The organic phase was distilled under reduced pressure to generate a distillate volume of 560 L while simultaneously adding isopropanol (350 L) and producing a solution of methyl 4-(3-chlorophenyl)-5-(4-chlorophenyl)-2-methyl-5-oxopentanoate in isopropanol (54 wt %, 140 kg total solution mass). The solution had a water content of 0.01 wt % by Karl Fisher. Additional isopropanol (420 L) and sulfuric acid (53 Kg, 535 mol) were added to the solution. The mixture was warmed to reflux and agitated for 12 h, during which time 200 L of solvent were distilled and 200 L of fresh isopropanol were added to the mixture. The mixture was cooled to 20° C. and water (180 L) was added over the course of 30 minutes. Isopropyl acetate (270 L) was added and the mixture was agitated for 30 minutes. The phases were separated and the aqueous phase was extracted using isopropyl acetate (100 L). The combined organic phases were washed with water (200 L) four times. The organic phase was distilled under reduced pressure to generate a distillate volume of 500 L while simultaneously adding isopropanol (50 L) and producing a solution of isopropyl 4-(3-chlorophenyl)-5-(4-chlorophenyl)-2-methyl-5-oxopentanoate in isopropanol (60 wt %, 134 kg total solution mass). The solution had a water content of 0.02 wt % by Karl Fisher. The title material was obtained in 81% overall yield as a roughly 1:1 mixture if diastereoisomers.

$^1$H NMR (400 MHz, CDCl$_3$, δ ppm): 7.70-7.80 (m, 2H), 7.22-7.28 (m, 2H), 7.00-7.18 (series of m, 4H), 4.78-4.96 (m, 1H), 4.42-4.50 (m, 1H), 2.02-2.30 (m, 2H), 1.80-1.95 (m, 1H), 0.99-1.19 (m, 15H).

Step 2. (3S,5R,6R)-3-Allyl-5-(3-chlorophenyl)-6-(4-chlorophenyl)-3-methyltetrahydro-2H-pyran-2-one

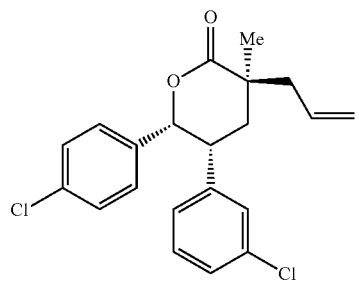 [SMILES: C=CC[C@@]1(C)C[C@H](c2cccc(Cl)c2)[C@H](c2ccc(Cl)cc2)OC1=O]

To a degassed solution of isopropyl 4-(3-chlorophenyl)-5-(4-chlorophenyl)-2-methyl-5-oxopentanoate in isopropanol (60 wt %, 252 kg total solution mass, 151 Kg of isopropyl ester starting material, 385 mol) was added degassed isopropanol (900 L) and potassium tert-butoxide (13 Kg, 116 mol). A separately prepared degassed solution of (S)-RUCY®-XylBINAP (also known as RuCl[(S)-diapena][(S)-xylbinap] (230 g, 0.2 mol, catalyst, Takasago International Corporation, Rockleigh, N.J.) in isopropanol (25 L). The mixture was purged four times with hydrogen at 5 bars (500 kPa) and agitated at 20° C. for 5.5 h. The hydrogen pressurization was discontinued and the mixture was degassed with nitrogen. Tetrahydrofuran (460 L) was added to the mixture. A solution of lithium hydroxide (24 Kg, 576 mol) in water (305 L) was added to the reaction mixture over the course of 40 minutes and the resultant mixture was agitated at 20° C. for 24 h. A solution of concentrated hydrochloric acid (79.3 Kg, 11.4 M, 740 mol) in water (690 L) was added to the mixture over the course of 2 h. Toluene (580 L) was added, the mixture was agitated for 30 minutes, and the phases were separated. The aqueous was extracted using toluene (700 L). The combined organic layers were washed with an aqueous solution of sodium chloride (25 wt %, 700 Kg). The organic phase was distilled at atmospheric pressure and 100° C. to generate a distillate volume of 2700 L while simultaneously adding toluene (800 L). Less than 0.05 wt % isopropanol or water (by Karl Fisher) were left in the mixture after this solvent exchange. Carbonyl diimidazole (59 Kg, 365 mol) was added to the toluene solution over the course of 2 h and the mixture was agitated at 20° C. for two additional hours. The mixture was cooled to 10° C. and a solution of orthophosphoric acid (72 Kg, 545 mol) in water (400 L) was added over the course of 1 h, while maintaining the temperature of the mixture below 20° C. The mixture was agitated for 30 minutes, the phases were separated and the organic layer was washed with an aqueous solution of sodium chloride (25 wt %, 484 Kg). Toluene (400 L) was distilled at atmospheric pressure and 110° C. After cooling of the solution to 20° C., tetrahydrofuran (500 L) was added and the water content by Karl Fisher was measured to be 0.03 wt %. The product solution was cooled to −10° C. and a solution allyl bromide (66.8 Kg, 552 mol) in tetrahydrofuran (50 L) was added. A lithium hexamethyldisilazide solution in toluene (255 Kg, 26 wt %, 492 mol) was added over the course of 6 h and the mixture was stirred at −10° C. for 1 h. The mixture was warmed to 0° C. and an aqueous solution of orthophosphoric acid (40 wt %, 400 mol) was added over the course of 3 h. The mixture was warmed to 20° C. Water (200 L) and dichloromethane (400 L) were added. The mixture was agitated for 15 minutes and the phases were separated. The solution was distilled at atmospheric pressure and 100° C. to generate a distillate volume of 1350 L and the residual toluene in the mixture was measured to be 9.8 wt %. The mixture was cooled to 70° C. Diisopropyl ether (85 L), water (26 L), and isopropanol (65 L) were added. The mixture was cooled to 35° C., agitated for 9 h, cooled to 30° C., and filtered. The filtered material was washed three times with heptane (80 L). The solids were dried at 55° C. for 48 hours to provide 90.1 Kg of (3S,5R,6R)-3-allyl-5-(3-chlorophenyl)-6-(4-chlorophenyl)-3-methyltetrahydro-2H-pyran-2-one in 63% overall yield. Chiral HPLC indicated an enantiomeric ratio of 99.95:0.05.

Step E. (S)-2-((2R,3R)-2-(3-Chlorophenyl)-3-(4-chlorophenyl)-3-hydroxypropyl)-N-((S)-1-hydroxy-3-methylbutan-2-yl)-2-methylpent-4-enamide

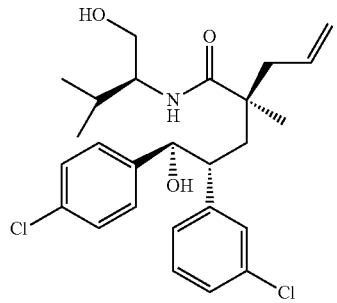 [SMILES: C=CC[C@@](C)(C[C@H](c1cccc(Cl)c1)[C@@H](O)c1ccc(Cl)cc1)C(=O)N[C@H](CO)C(C)C]

(3S,5R,6R)-3-Allyl-5-(3-chlorophenyl)-6-(4-chlorophenyl)-3-methyltetrahydro-2H-pyran-2-one (113 g, 300.0 mmol) was combined with (S)-2-amino-3-methylbutan-1-ol (93 g, 900.0 mmol) and the suspension was heated at 100° C. for 5 hours. The reaction mixture was cooled to room temperature, diluted with ethyl acetate (1000 mL) and washed with 1N hydrochloric acid (2×), water, and brine. The organic layer was dried over magnesium sulfate and concentrated under a vacuum to give the title compound as a white solid which was used in next step without further purification.

Step F. (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate

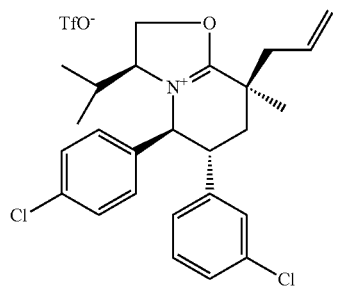 [SMILES: "TfO-" ; C=CC[C@@]1(C)C[C@H](c2cccc(Cl)c2)[C@@H](c2ccc(Cl)cc2)[N+]2=C1OC[C@@H]2C(C)C]

Trifluoromethanesulfonic anhydride (57 mL, 339 mmol) was added dropwise over 60 minutes via addition funnel to a solution of (S)-2-((2R,3R)-2-(3-chlorophenyl)-3-(4-chlorophenyl)-3-hydroxypropyl)-N—((S)-1-hydroxy-3-methylbutan-2-yl)-2-methylpent-4-enamide (73.7 g, 154 mmol) and 2,6-dimethylpyridine (78 mL, 678 mmol) in dichloromethane (700 mL) at −50° C. The reaction mixture was stirred at −50° C. for one additional hour and concentrated under a vacuum to provide the title compound as a reddish solid which was used in next step without further purification.

Step G. (3S,5R,6S)-3-Allyl-5-(3-chlorophenyl)-6-(4-chlorophenyl)-1-((S)-1-(isopropylthio)-3-methylbutan-2-yl)-3-methylpiperidin-2-one

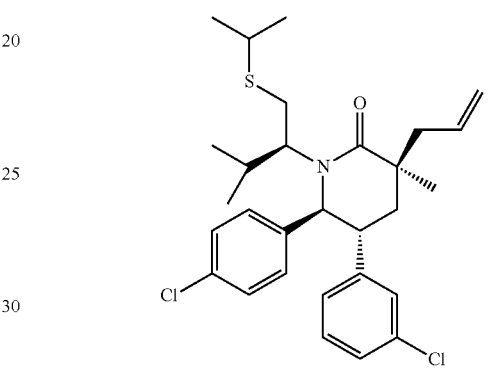

(3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (736 mg, 1.242 mmol) was weighed into an oven dried 50 mL pear-bottom flask and dissolved in 20 mL dry toluene. The toluene was removed under a vacuum to remove trace water in the solid. The process was repeated twice, and the resulting residue was dried under a strong vacuum.

A solution of sodium isopropyl sulfide was prepared by adding potassium 2-methylpropan-2-olate (3.0 mL, 3.00 mmol, 1 M solution in tetrahydrofuran) to a solution of propane-2-thiol (331 mg, 4.35 mmol) in 8 mL dimethylformamide that had been prepared under nitrogen and cooled to 0° C. The sulfide solution was allowed to stir at room temperature for five minutes and was cooled to 0° C. The dry (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (736 mg, 1.242 mmol) was dissolved in dimethylformamide (8 mL total) and transferred (3 transfers total) via syringe to the sulfide solution over the course of 5 minutes. After 5 minutes, the ice bath was removed and the pale orange solution was allowed to warm to room temperature.

After stirring overnight, the mixture was partitioned between ethyl acetate and saturated ammonium chloride solution. The aqueous phase was saturated in sodium chloride and back-extracted three times. The combined organics were washed twice with saturated sodium bicarbonate, twice with brine, dried over sodium sulfate, filtered, and concentrated under a vacuum to provide a residue that was purified by silica gel column chromatography (80 g column, gradient elution of 0% to 50% ethyl acetate in hexanes).

Method for making

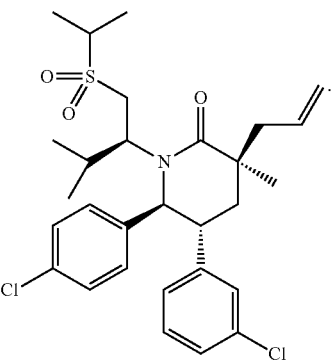 [SMILES: C=CC[C@@]1(C)C[C@H](c2cccc(Cl)c2)[C@@H](c2ccc(Cl)cc2)N([C@H](CS(=O)(=O)C(C)C)C(C)C)C1=O]

Step A. (3S,5R,6S)-3-Allyl-5-(3-chlorophenyl)-6-(4-chlorophenyl)-1-((S)-1-hydroxy-3-methylbutan-2-yl)-3-methylpiperidin-2-one

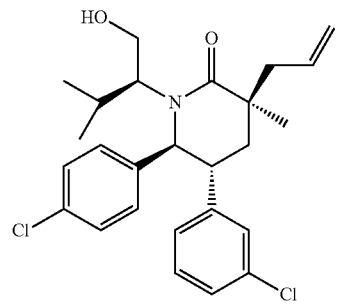 [SMILES: C=CC[C@@]1(C)C[C@H](c2cccc(Cl)c2)[C@@H](c2ccc(Cl)cc2)N([C@H](CO)C(C)C)C1=O]

Lithium hydroxide hydrate (64.6 g, 1540 mmol) was added portionwise, over a 5 minute period, to a solution of (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium trifluoromethanesulfonate (Step F above) dissolved in tetrahydrofuran (500 ml) and water (300 ml). The reaction mixture was stirred at room temperature for 1 hour and concentrated under a vacuum. The residue was dissolved in ethyl acetate (ca. 1.3 L) and the layers were separated. The organic layer was washed with 1N hydrochloric acid (ice cooled, with enough hydrochloric acid to protonate and remove any remaining 2,6-dimethylpyridine (300 mL×2)), water and brine. The solvent was removed under a vacuum to give a residue which was purified by silica gel column chromatography (1500 g column, gradient elution of 0% to 50% ethyl acetate in hexanes. The product was also crystallized from cyclohexane.

Step B. (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium 4-methylbenzenesulfonate

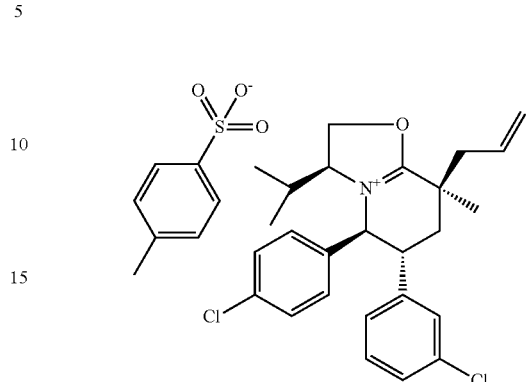

(3S,5R,6S)-3-Allyl-5-(3-chlorophenyl)-6-(4-chlorophenyl)-1-((S)-1-hydroxy-3-methylbutan-2-yl)-3-methylpiperidin-2-one (49.77 g, 98 mmol) was transferred to a 1000 mL flask containing 4-methylbenzenesulfonic acid hydrate (19.27 g, 101 mmol) and a stirring bar. The reactants were suspended in toluene (230 mL). The flask was equipped with a Dean Stark trap and reflux condenser, and the stirred mixture was heated at reflux in a preheated bath. After 1 hour, the solvent was carefully removed under a vacuum and the resulting residue was further dried under high vacuum. The title compound was taken to the next step without purification.

Step C. (3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one

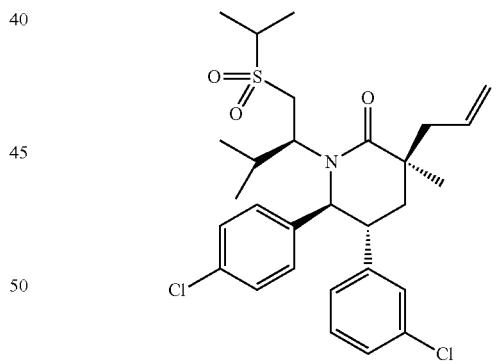

(3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium 4-methylbenzenesulfonate, dry, powdered potassium carbonate (26.9 g, 195 mmol) and propane-2-thiol (14 ml, 150 mmol) were added along with 200 mL freshly sparged dimethylformamide. The mixture was heated under argon at 50° C. After about 21 hours, a solution of meta-chloroperbenzoic acid (68.2 g, 77% pure by weight, in 100 mL dimethylformamide) was transferred to a dropping funnel and rapidly added to the stirred reaction mixture while the flask was immersed in an ice bath. After 5 minutes, the resulting yellow solution was allowed to warm to room temperature. After 10 minutes, additional meta-chloroperbenzoic acid (12 g, 77% wt %) was added as a solid and the mixture was stirred at room temperature. Upon completion, the mixture was poured into ethyl acetate and washed with 1 M sodium hydroxide (500 mL) that had been poured into ice. The aqueous phase was back-extracted three times and washed with additional 1 M NaOH (500 mL, also poured into ice). The aqueous layer was washed once with ethyl acetate and the organics were combined. Sodium thiosulfate (1 M in water, 250 mL) was added to the organics in a large Erlenmeyer flask, and the mixture was stirred for twenty minutes. The organic phase was washed again with sodium thiosulfate (1 M in water, 250 mL) and the mixture was allowed to stand over the weekend. The organics were concentrated to ca. 500 mL, then sequentially washed with 10% aqueous citric acid, 1 M sodium hydroxide, and brine. The organics were dried over sodium sulfate, filtered, and concentrated to give the crude product. The residue was purified by flash column chromatography (1.5 kg silica gel column, gradient elution of 0% to 50% ethyl acetate in hexanes) to give the title compound as a white solid.

Synthesis of Compound A (Synthesis A)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

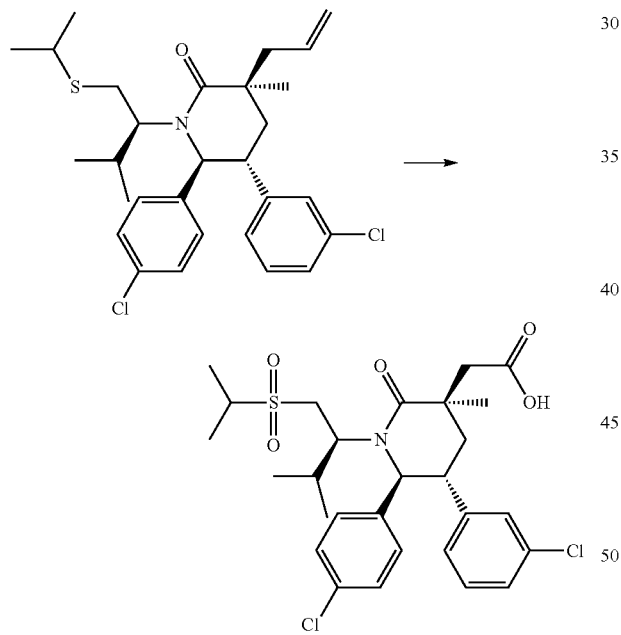

Ruthenium(III) chloride trihydrate (22 mg, 0.084 mmol) and sodium periodate (1.12 g, 5.24 mmol) were added to a mixture of (3S,5R,6S)-3-allyl-5-(3-chlorophenyl)-6-(4-chlorophenyl)-1-((S)-1-(isopropylthio)-3-methylbutan-2-yl)-3-methylpiperidin-2-one (390 mg, 0.752 mmol) in acetonitrile (4.0 mL), carbon tetrachloride (4.0 mL), and water (6.0 mL). The resulting dark brown mixture was vigorously stirred at ambient temperature overnight. The mixture was filtered through a pad of diatomaceous earth, washing with ethyl acetate. The filtrate was partitioned between 2 M HCl and ethyl acetate. The aqueous phase was back-extracted twice with ethyl acetate, and the combined organics were washed with brine, dried over sodium sulfate, filtered, and concentrated under a vacuum to a residue that was purified by flash chromatography (40 g silica gel column, gradient elution of 0% to 15% isopropanol in hexanes). Fractions containing the desired product were combined, stripped of solvent, redissolved in minimal ACN/water, frozen, and lyophilized to give a white powder.

Subsequently, a mixture of (3S,5R,6S)-3-allyl-5-(3-chlorophenyl)-6-(4-chlorophenyl)-1-((S)-1-(isopropylthio)-3-methylbutan-2-yl)-3-methylpiperidin-2-one (388 mg, 0.748 mmol), ruthenium(III) chloride trihydrate (19.56 mg, 0.075 mmol), and sodium periodate (1.15 g, 5.38 mmol) in acetonitrile (4 mL), carbon tetrachloride (4.00 mL), and water (4.00 mL) was vigorously stirred at ambient temperature. After four hours, the mixture was filtered through a pad of diatomaceous earth, and the filtrate was partitioned between ethyl acetate and 2 M HCl. The aqueous phase was back-extracted twice with ethyl acetate, and the combined organics were washed with brine, dried over sodium sulfate, filtered, and concentrated under a vacuum to a residue. The residue was purified by flash chromatography (40 g silica gel column, gradient elution of 0% to 15% isopropanol in hexanes). Fractions containing the product were concentrated and combined with the solid obtained in the prior experiment. The combined material was dissolved in minimal acetonitrile/water, frozen, and lyophilized overnight to give a white solid.

Figure 2:
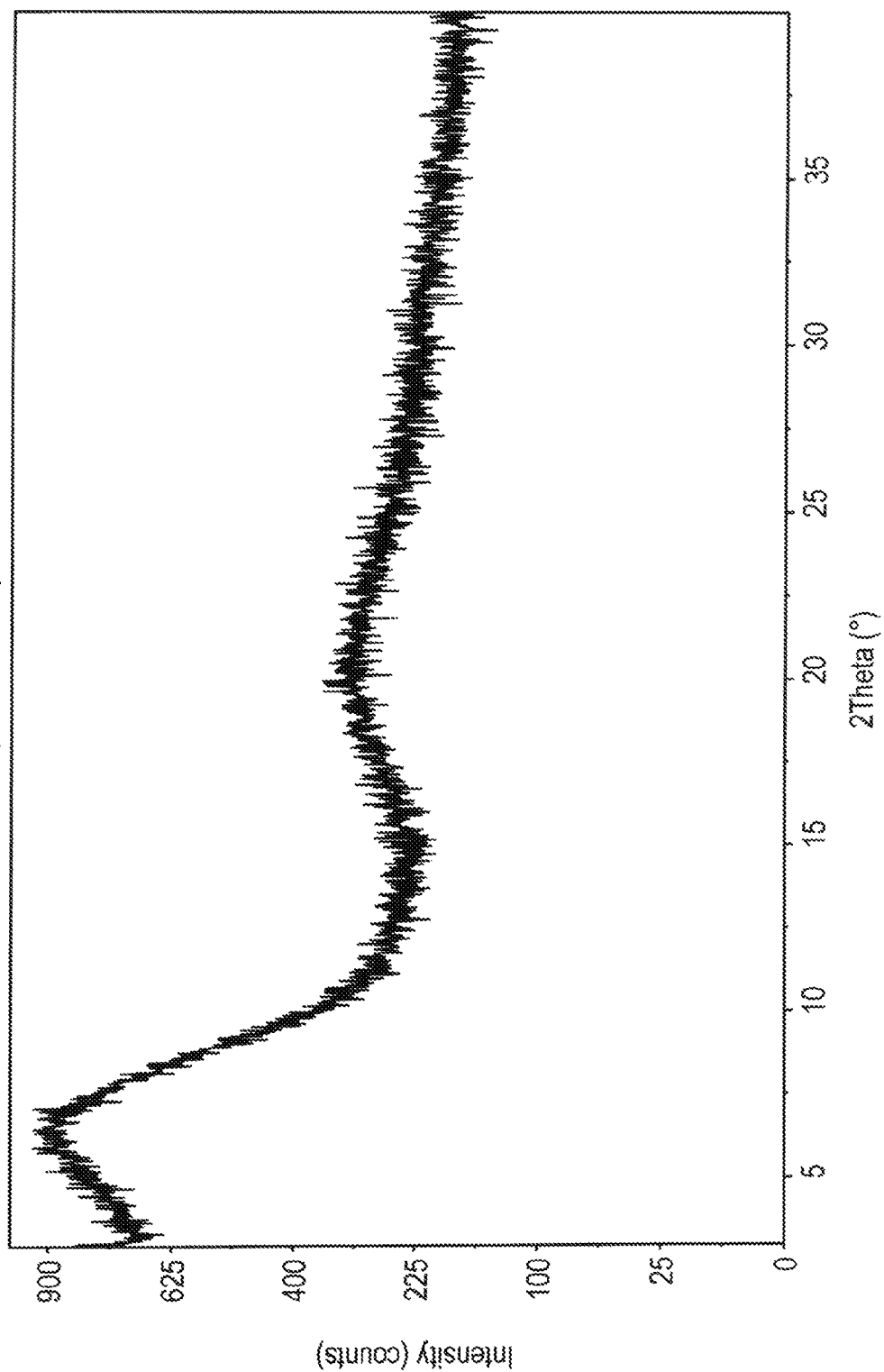
FIG. 2. XRPD Pattern of Compound A Amorphous
Figure 3:
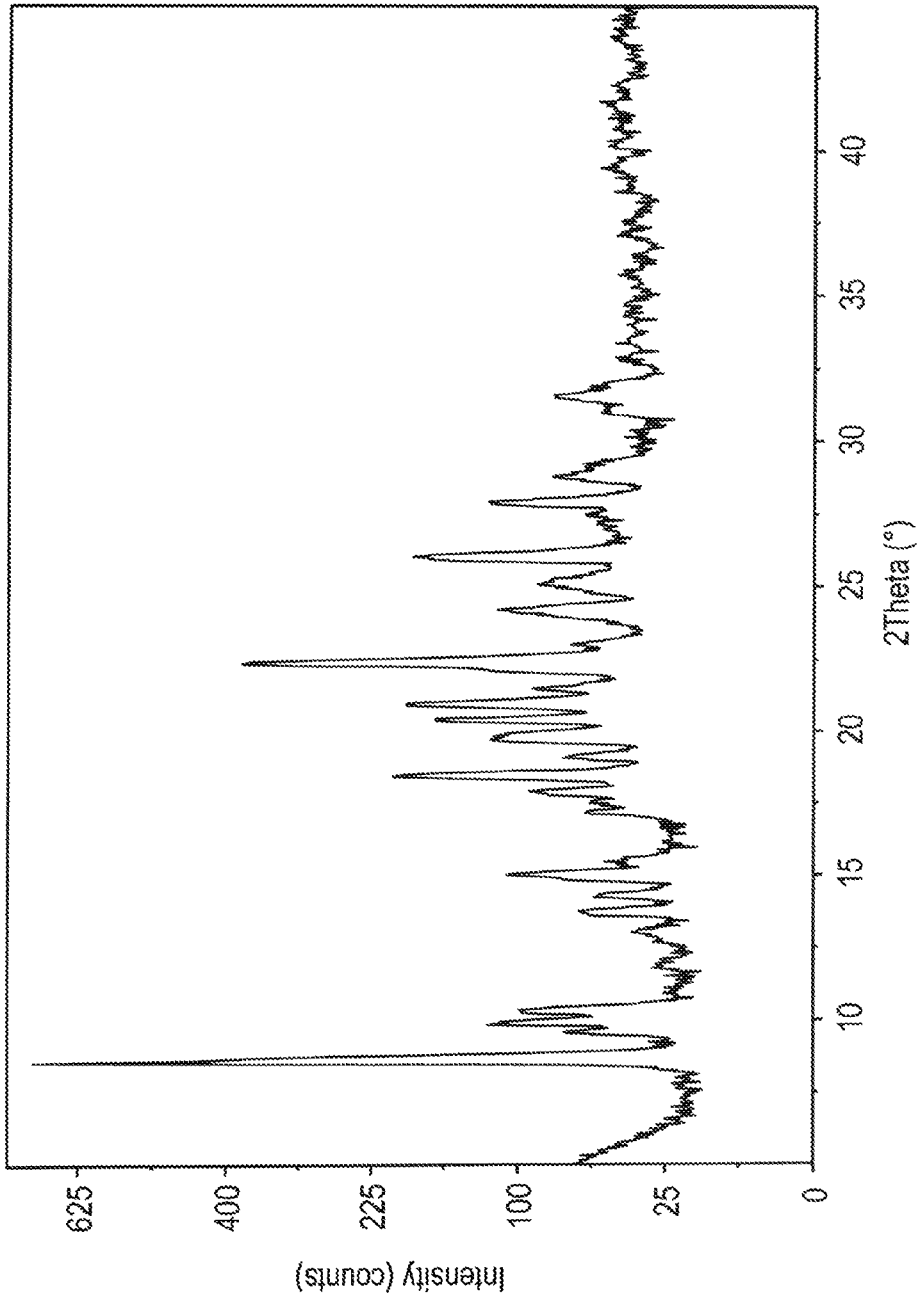
FIG. 3. XRPD Pattern of Crystalline (3S,5S,6R,8S)-8-allyl-6-(3-chlorophenyl)-5-(4-chlorophenyl)-3-isopropyl-8-methyl-2,3,5,6,7,8-hexahydrooxazolo [3,2-a]pyridin-4-ium naphthalene-1-sulfonate, hemi-toluene solvate FIG. 4. XRPD Pattern of Compound A Crystalline Form 1

The resulting XRPD pattern was consistent with the amorphous form (FIG. 2).

Synthesis of Compound A (Synthesis B)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

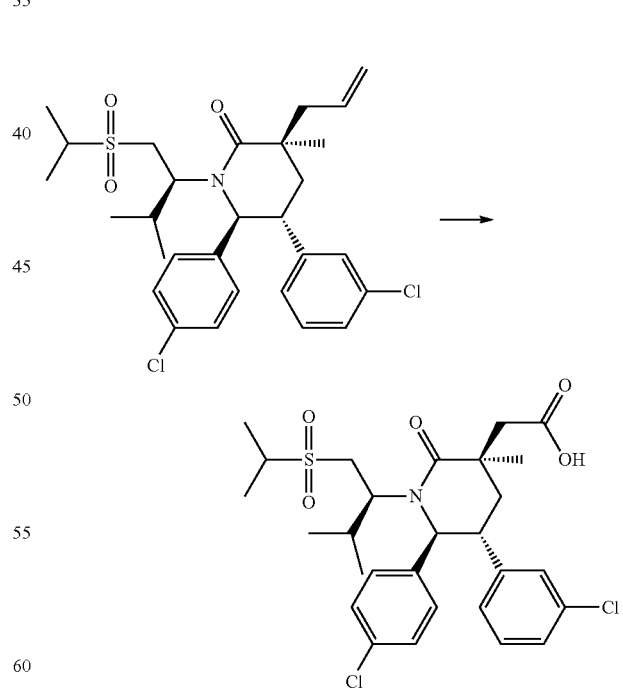

Sodium periodate (2.85 g, 13.32 mmol) and ruthenium (III) chloride trihydrate (0.049 g, 0.189 mmol) were added to a mixture of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (1.73 g, 3.14 mmol) in acetonitrile (18 mL), carbon tetrachloride (18 mL), and water (27 mL). The mixture was stirred vigorously at room temperature for 25 hours. The mixture was diluted with 2M HCl and filtered through a pad of diatomaceous earth and rinsed with ethyl acetate. The organic layer was separated, washed with brine, dried over sodium sulfate, filtered, and concentrated under a vacuum. The material was purified twice by flash chromatography (120 g silica gel, gradient elution of 0% to 20% isopropanol in hexanes; 120 g column, gradient elution of 0% to 15% gradient isopropanol in hexanes). It was purified once more by flash chromatography (220 g silica gel; gradient elution 0% to 20% isopropanol in hexanes, 45 minutes) using a method in which the purest fractions were concentrated and set aside and mixed fractions were pooled and resubjected to the chromatography.

Subsequently, a mixture of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (4.1 g, 7.45 mmol), ruthenium(III) chloride trihydrate (0.120 g, 0.459 mmol), and sodium periodate (6.73 g, 31.5 mmol) in acetonitrile (40 mL), carbon tetrachloride (40 mL), and water (60 mL) was vigorously stirred at ambient temperature for 23 hours. The reaction was diluted by addition of 2 M aqueous HCl and filtered through a diatomaceous earth pad, washing with copious ethyl acetate. Most of the organics were removed under a vacuum. The crude product was extracted into ethyl acetate, washed with brine, dried over sodium sulfate, filtered, and concentrated to a residue that was purified twice by flash chromatography (330 g silica gel column, gradient elution of 0% to 20% isopropanol in hexanes; 330 g silica gel column, gradient elution of 0% to 20% isopropanol in hexanes) to give an off-white foam. The material was purified by flash chromatography three additional times (220 g silica gel column; gradient elution 0% to 20% isopropanol in hexanes, 45 minutes) using a method in which the purest fractions were concentrated and set aside and mixed fractions were pooled and resubjected to the chromatography.

Mixed fractions from both experiments were combined and purified by flash chromatography twice more (220 g silica gel column; gradient elution 0% to 20% isopropanol in hexanes, 45 minutes), and again the pure fractions were set aside. All of the pure fractions were combined, concentrated under a vacuum, dissolved in minimal acetonitrile/water and lyophilized.

The XRPD pattern was consistent with the amorphous form (FIG. 2).

Synthesis of Compound A (Synthesis C)

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

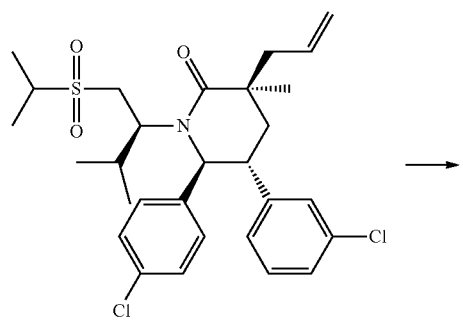

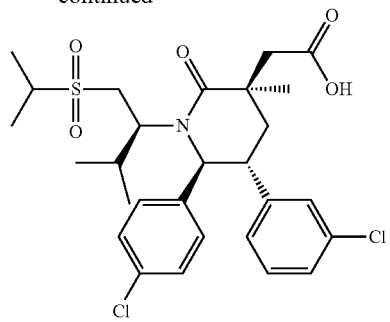

-continued (3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (5.05 g, 9.17 mmol) was weighed into a 500 mL round bottom flask containing a large stir bar and 2.04 g sodium periodate (2.04 g). The mixture was diluted with carbon tetrachloride (52 mL), acetonitrile, (52 mL) and water (78 mL). The flask was immersed in a room temperature water bath and the internal temperature was monitored with a digital thermocouple.

Ruthenium chloride hydrate (approximately 50 mg) was added in a single portion. The internal temperature rose to 22° C., then ice was added to the bath to cool the mixture. Additional ruthenium chloride hydrate (25 mg) was added 3 minutes later. After stirring for a total of thirty minutes, Three portions of sodium periodate (2.08 g, 2.07 g and 2.08 g) were slowly added on 15 minute intervals. The temperature was kept below 19° C., and ice was quickly added to the bath if the internal temperature began to rise. The mixture was stirred at ambient temperature overnight. The mixture was filtered through a pad of diatomaceous earth and the filter cake was washed copiously with ethyl acetate. The filtrate was concentrated under a vacuum and partitioned between 2 M HCl (100 mL) and ethyl acetate (200 mL).

Two rounds of flash column chromatography (330 g silica gel, then 220 g silica gel, gradient elution of 0% to 20% isopropanol in hexanes) provided the title compound. A portion of this material was lyophilized from acetonitrile and water. The less pure fractions were repurified by two additional rounds of flash column chromatography (220 g then 330 g silica gel columns, gradient elution of 0% to 20% isopropanol in hexanes). The most pure fractions from both runs were combined, concentrated under a vacuum and lyophilized from acetonitrile and water to give the title compound.

The XRPD pattern was consistent with the amorphous form (FIG. 2).

The three syntheses above resulted in amorphous compound A. No crystalline form was obtained. Attempts to crystallize amorphous compound A made in the above procedure (Synthesis C) are summarized in Table 1A below.

TABLE 1A

| Mass of Compound A (mg) | Volume solvent (mL) | Solvent composition | Condition | Observation |
|---|---|---|---|---|
| 7.5 | 1.0 | Water/ethanol (90/10 v/v)) | Slurry at room temperature | Amorphous by XRPD after 2 months |
| 8.0 | 1.0 | Water/dimethyl formamide (90/10 (v/v)) | Slurry at room temperature | Amorphous by XRPD after 2 months |

TABLE 1A-continued

| Mass of Compound A (mg) | Volume solvent (mL) | Solvent composition | Condition | Observation |
|---|---|---|---|---|
| 8.7 | 1.0 | Heptane/toluene (98/2 (v/v)) | Slurry at room temperature | Amorphous by XRPD after 2 months |
| 8.7 | 1.0 | Heptane/methyl-t-butylether (98/2 (v/v)) | Slurry at room temperature | Amorphous by XRPD after 2 months |
| 9.5 | 1.0 | Cyclohexane/toluene (98/2 (v/v)) | Slurry at room temperature | Amorphous by XRPD after 27 days |
| 10.5 | 1.0 | Cyclohexane/methyl-t-butylether (98/2 (v/v)) | Slurry at room temperature | Amorphous by XRPD after 27 days | stirring at 25° C. for 8 hours. The evaporation plate (200 μL/well filtrate) was left open at ambient for 24 hours. The sealed precipitation plate (150 μL/well filtrate injected into pre-filled 150 μL anti-solvent; either water or heptane (Table 1)) was cooled linearly from 25° C. to 5° C. in 8 hours and held at 5° C. for 8 hours. The sealed cooling plate (300 μL/well filtrate) was started at 25° C., cooled to 5° C. in 8 hours, and held at 5° C. for additional 8 hours. At the end of crystallization, the precipitation and cooling plates were centrifuged at 5° C. for 10 min at 1500 rpm, and the supernatant in each well of both plates was aspirated and discarded. Prior to dissembling each of 4 plates to collect the crystal samples on its 96-well glass substrates, wick paper was used to dip into each well to ensure the dryness.

TABLE 1

Solvent Dispense Table For HT Form Screen. All Solvent Mixtures Are (V/V).

| | 7 | 8 | 9 | 10 | 11 | 12 |
|---|---|---|---|---|---|---|
| Anti-solvent | Water | Water | Water | Water | Heptane | Heptane |
| | DCE/Heptane (5/95) | DCE/heptane (10/90) | Toluene/heptane (5/95) | MTBE/heptane (5/95) | THF/heptane (20/80) | THF/heptane (40/60) |
| | THF/Heptane (5/95) | THF/heptane (10/90 | Toluene/heptane (10/90) | MTBE (10/90) | DMF/heptane (20/80) | DMF/heptane (40/60) |
| | IPAc/Heptane (5/95) | IPAc/heptane (10/90) | Acetic acid | MEK/heptane (5/95) | Acetone/heptane (20/80) | Acetone/heptane (40/60) |
| | IPA/Heptane (5/95) | IPA/heptane (10/90)e | Heptane | MEK/heptane (10/90) | Acetonitrile/heptane (20/80) | Acetonitrile/heptane (40/60) |
| | DCE/cyclohexane (5/95) | DCE/cyclohexane (10/90) | Toluene/cyclohexane (5/95) | MTBE/cyclohexane (5/95) | Ethanol/cyclohexane (20/80) | Ethanol/cyclohexane (40/60) |
| | THF/cyclohexane (5/95) | THF/cyclohexane (10/90) | Toluene/cyclohexane 10/90) | MTBE/cyclohexane (10/90) | IPA/cyclohexane (20/80) | IPA/cyclohexane (40/60) |
| | IPAc/cyclohexane (5/95) | IPAc/cyclohexane (10/90) | Acetic acid | MEK/cyclohexane (5/95) | NMP/cyclohexane (20/80) | NMP/cyclohexane (40/60) |
| | IPA/cyclohexane (5/95) | IPA/cyclohexane (10/90) | cyclohexane | MEK/cyclohexane (10/90) | water | 0.01M NaOH in water |

Figure 5:
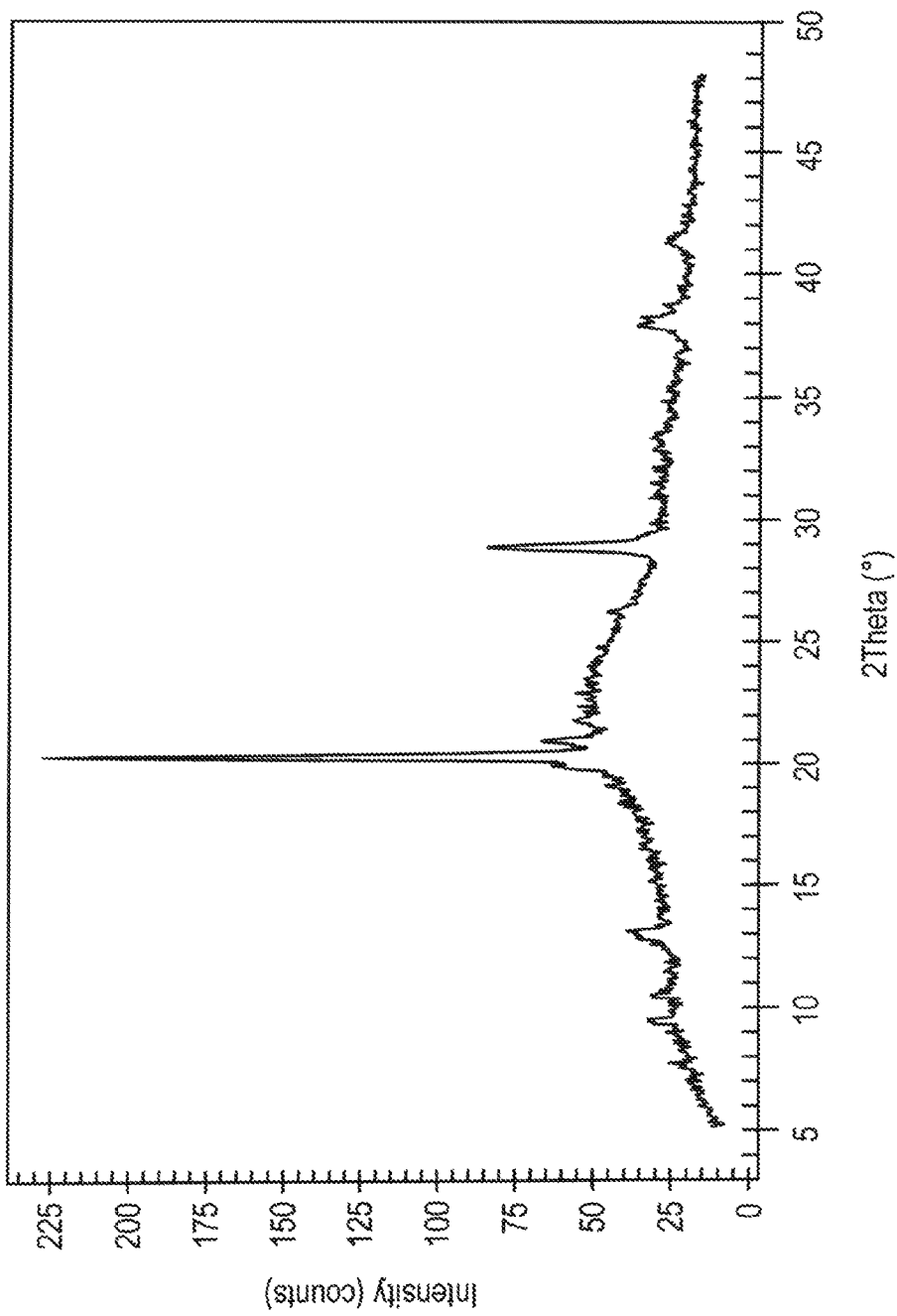
FIG. 5. XRPD Pattern of Compound A Crystalline Form 2

The amorphous compound made in the procedure above (Synthesis C) was used in a high-throughput (HT) polymorph screen. The starting material was observed to be amorphous by XRPD. In the form screening experiment, of 192 conditions tested, only 1 crystalline sample was observed representing one form shown in FIG. 5 (compound A crystalline Form 2). The form identified by the HTS screen is not consistent with compound A crystalline anhydrous.

The compound loading amount was about 8 mg/well. Amorphous compound A (Synthesis C) was dispensed into each well on a 96-well glass vial rack. The solid samples in the vials were then transferred to a 96-well crystallization source plate.

Per library design, crystallization solvents were dispensed into the source plate (960 μL/vial) (Table 1 and Table 2). After solvent addition, the source plate was sonicated for 30 minutes, then heated at 55° C. with stirring for 30 minutes and kept at 25° C. without stirring for 30 minutes. Maintaining at 25° C., the solvents in the source plate were aspirated and filtered into a filtration plate. The filtrate was subsequently aspirated and dispensed into three crystallization plates (evaporation, precipitation, cooling). After completion of 96-well filtration, the source plate was kept Birefringence images were collected for each well of the four 96-well plates using cross-polarized light optical microscopy. XRPD patterns were collected on a Bruker D8 Discover X-ray diffraction system fitted with a motorized xyz sample stage and a general area detector diffraction system (GADDS) area detector. The screen samples on a flat glass plate were mapped and a sample area of 1 mm$^2$ was scanned in oscillating mode for 3 minutes from 5° to 48° 2θ using CuKα radiation (40 kv, 40 mA) through a graphite monochromator and a collimator of 0.5 mm pinhole. In addition to the screen plates the starting material, was also analyzed using this instrument and method.

In addition, HT crystallization experiments using bases as additives were conducted. Stoichiometric amounts of CH$_3$OK, CH$_3$ONa, Tris and ammonium hydroxide were added as MeOH solutions, Ca(OH)$_2$, lysine, diethanolamine, and diethylamine were added as aqueous solutions and the solvent evaporated under a stream of blown nitrogen prior to solvent dispensing.

Per library design, crystallization solvents were dispensed into the source plate (960 μL/well). After solvent addition, the source plate was sonicated for 30 minutes, then heated at 55° C. with stirring for 30 minutes and kept at 25° C.

without stirring for 30 minutes. Maintaining at 25° C., the solvents in the source plate were aspirated and filtered into a filtration plate. The filtrate was subsequently aspirated and dispensed into three crystallization plates (evaporation, precipitation, cooling). After completion of 96-well filtration, the source plate was kept stirring at 25° C. for 8 hours. The evaporation plate (200 µL/well filtrate) was left open at ambient for 24 hours. The sealed precipitation plate (150 µL/well filtrate injected into pre-filled 150 µL anti-solvent) was cooled linearly from 25° C. to 5° C. in 8 hours and held at 5° C. for 8 hours. The sealed cooling plate (300 µL/well filtrate) was started at 25° C., cubic cooled to 5° C. in 8 hours, and held at 5° C. for additional 8 hours. At the end of crystallization, the precipitation and cooling plates were centrifuged at 5° C. for 10 min at 1500 rpm, and the supernatant in each well of both plates was aspirated and discarded. Prior to dissembling each of 4 plates to collect the crystal samples on its 96-well glass substrates, wick paper was used to dip into each well to ensure the dryness.

Figure 4:
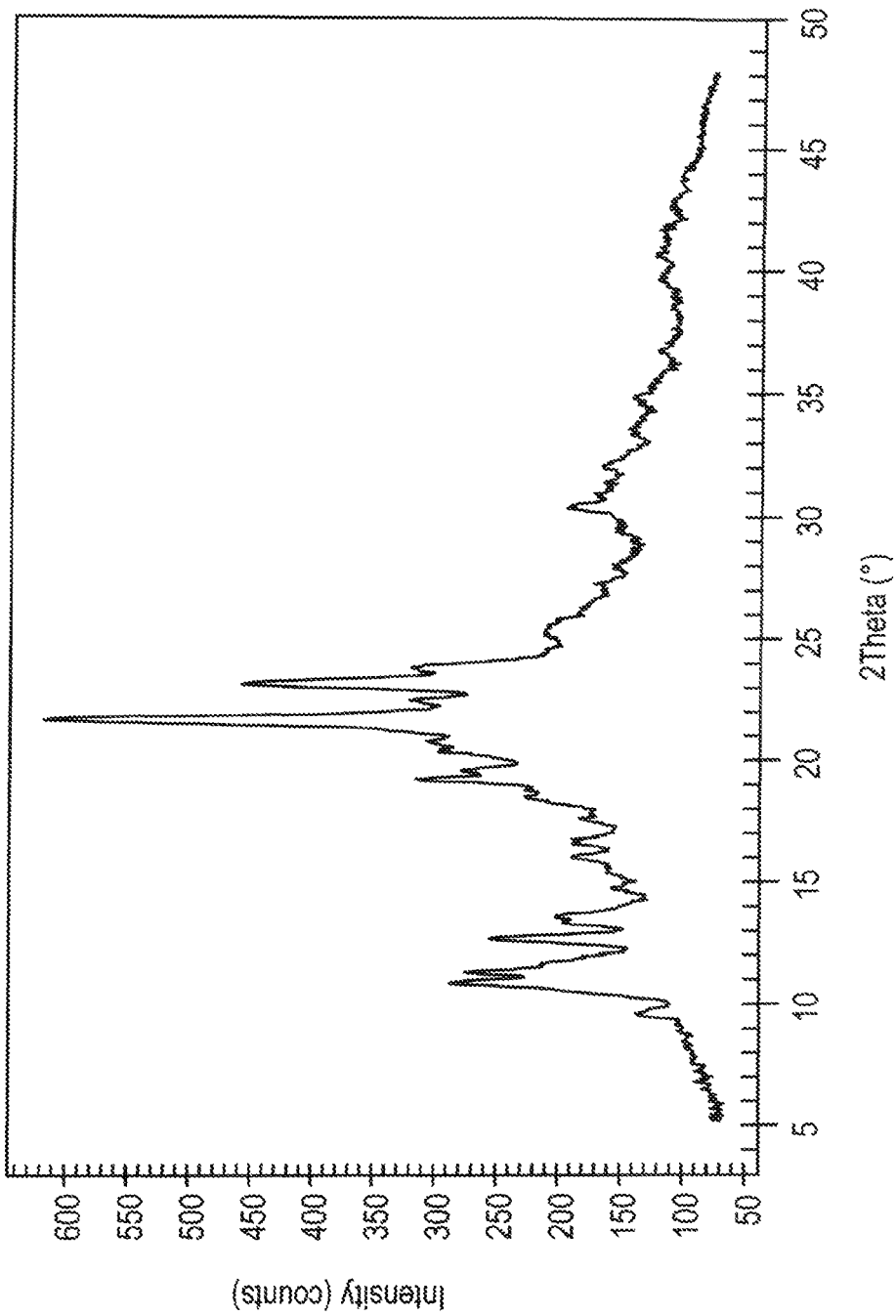

None of these experiments resulted in any crystalline salts. Seven (7) samples yielded a crystalline form consistent with the XRPD pattern of FIG. 4 (compound A crystalline form 1). All crystalline samples observed in this part of the screen were processed by evaporation. Samples evaporated from IPA with $CH_3OK$, from MeCN with Tris, from THF/$H_2O$ (90/10) with lysine, from IPA with lysine, from THF/water (90/10) with diethanolamine, from MeCN with diethanolamine, and from toluene/MeOH (50/50) with diethanol amine gave crystalline samples that were consistent with Compound A Crystalline Form 1 by XRPD.

Experiment 2

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid (100 mg) was placed in a 13 mm test tube and dissolved in 1 mL ethanol and heated to reflux. Water was added dropwise until the cloudiness that formed upon addition took a few seconds to disappear (1 mL water, total, was added). The solution was cooled slowly. It oiled-out before reaching room temperature. Additional ethanol (0.2 mL) was added, and the mixture was heated to reflux. The material oiled out upon slow cooling to room temperature. Additional ethanol (0.2 mL) was added, and the mixture was heated at reflux. The mixture did not oil out after cooling to room temperature, but no crystals formed. After 1.5 hours at room temperature the solution was placed in the freezer, and the material oiled-out.

Experiment 3

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid (100 mg, white foam) was placed in a 13 mm test tube, and 1 mL of 60% ethanol in water was added at room temperature. The foam either completely dissolved or mostly dissolved before precipitating out as a white solid. The solid was collected by vacuum filtration. Analysis showed the solid was more pure than the starting material. 2-((3R,5R,6S)-5-(3-Chlorophenyl)-6-(4-chlorophenyl)-1-((S)-1-(isopropylsulfonyl)-3-methylbutan-

TABLE 2

Solvent Dispense Table For HT Form Screen. All Solvent Mixtures Are (V/V).

| | | 1 | 2 | 3 | 4 | 5 | 6 |
|---|---|---|---|---|---|---|---|
| | Counterion\anti-solvent | Heptane | Heptane | Heptane | Heptane | Heptane | Heptane |
| A | Ammonia | THF | THF/$H_2O$ (90/10) | IPA | MeCN | IPA | Toluene/MeOH (50/50) |
| B | $CH_3OK$ | THF | THF/$H_2O$ (90/10) | IPA | MeCN | IPA | Toluene/MeOH (50/50) |
| C | $CH_3ONa$ | THF | THF/$H_2O$ (90/10) | IPA | MeCN | IPA | Toluene/MeOH (50/50) |
| D | $Ca(OH)_2$ (0.5 eq) | THF | THF/$H_2O$ (90/10) | IPA | MeCN | IPA | Toluene/MeOH (50/50) |
| E | Tris | THF | THF/$H_2O$ (90/10) | IPA | MeCN | IPA | Toluene/MeOH (50/50) |
| F | Lysine | THF | THF/$H_2O$ (90/10) | EtOH/$H_2O$ (90/10) | MeCN | IPA | MeCH/$H_2O$ (90/10) |
| G | Dienthanolamine | THF | THF/$H_2O$ (90/10) | IPA | MeCN | IPA | Toluene/MeOH (50/50) |
| H | Diethylamine | THF | THF/$H_2O$ (90/10) | IPA | MeCN | IPA | Toluene/MeOH (50/50) |

Crystallization Studies

Experiment 1

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid (100 mg) was placed in a 13 mm test tube, and 1 mL of 40% ethanol in water was added at room temperature. The material did not dissolve, even after heating at reflux. An additional 2 mL of 40% ethanol in water was added, and still the material did not completely dissolve after reflux. Ethanol was added dropwise until the material went into solution. The solution was slowly cooled. The material oiled-out before reaching room temperature.

Figure 6:
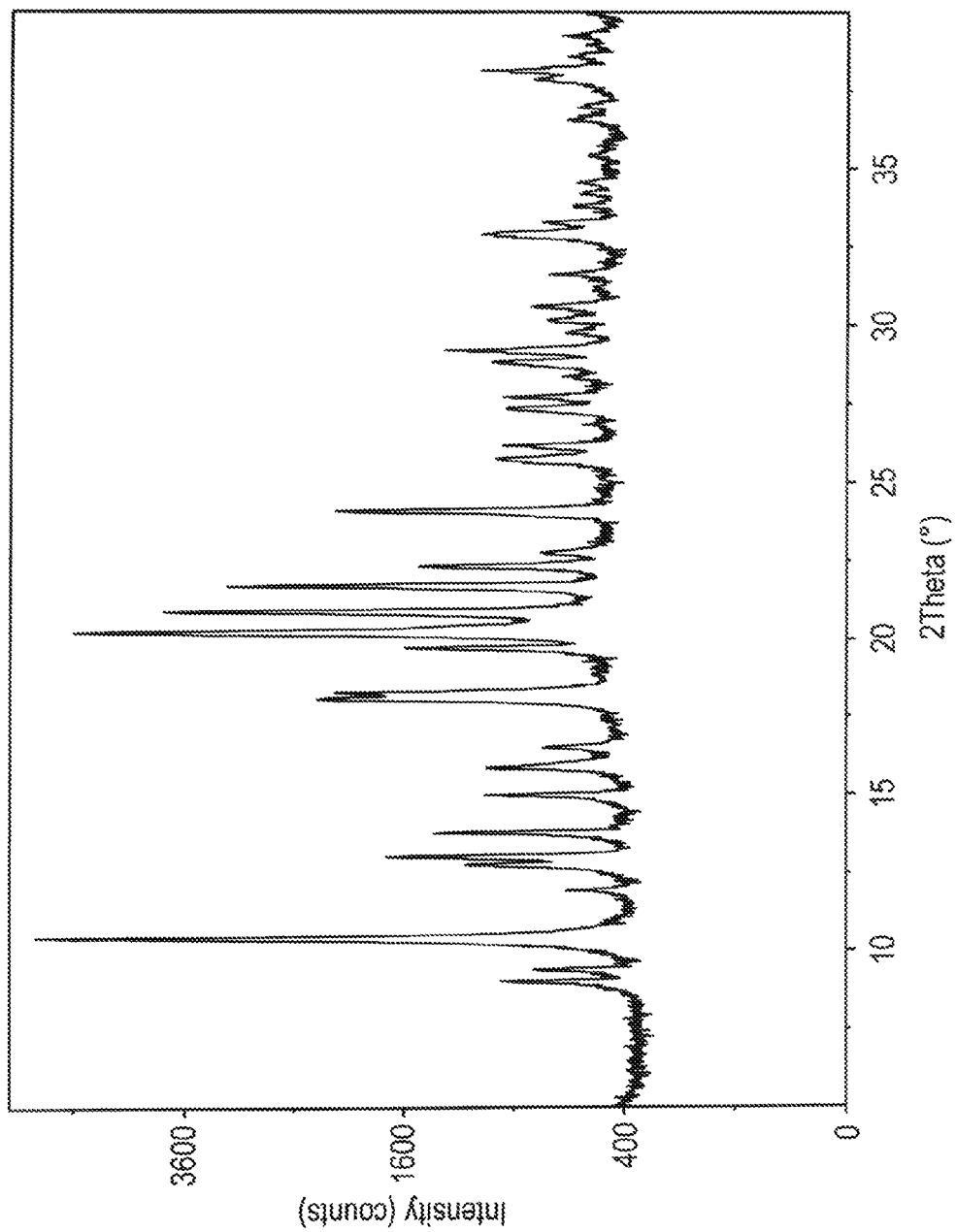
FIG. 6. XRPD Pattern of Compound A Ethanolate (ethanol solvate)

2-yl)-3-methyl-2-oxopiperidin-3-yl)acetic acid (100 mg, white foam) was placed in a 13 mm test tube, and 1 mL of 60% ethanol in water was added. The mixture was stirred at room temperature during addition and the material briefly dissolved before precipitating as a white solid. The mixture was heated at reflux to dissolve the material and slowly cooled to room temperature. After stirring overnight at room temperature, no crystals had formed. The solution was seeded with solid prepared in the preceding experiment, and solid formed immediately. The crystals were collected by vacuum filtration and washed with a cold solution of 60% ethanol in water to provide a white crystalline solid. Analysis showed further improvement to the purity, and X-ray diffraction indicated the material was crystalline. The XRPD was consistent with Compound A ethanolate (FIG. 6).

Experiment 4

2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid (100 mg, white foam) was placed in a 13 mm test tube, and 0.75 mL of 60% ethanol in water was added. The mixture was stirred at room temperature during addition, and after a few minutes, the foam was replaced by a white crystalline solid. The mixture was heated to reflux, slowly cooled to room temperature without stirring. After a few days, large crystals had formed. They were collected by vacuum filtration to provide the title compound as colorless needles. A single crystal X-ray structure was obtained and was consistent with compound A ethanolate (FIG. 6).

Synthesis of Compound A Ethanolate 2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

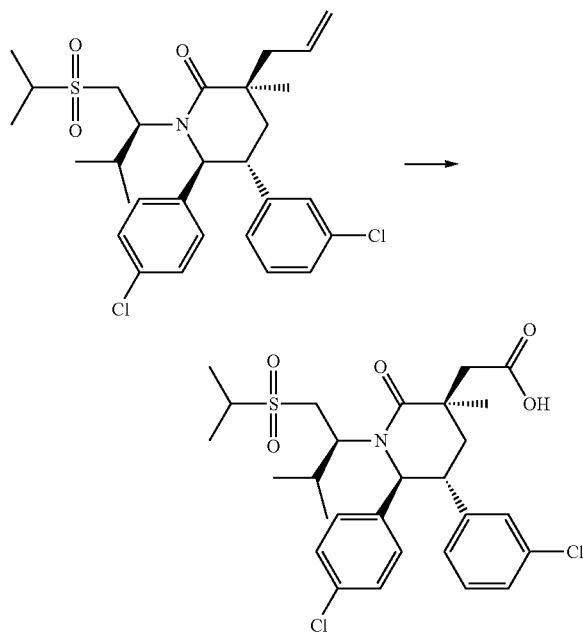

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (86.8 g, 158 mmol) was dissolved in acetonitrile (300 mL) and ethyl acetate (300 mL) and transferred to a 2 L 3-neck Morton flask. Water (450 mL) was added. The flask was equipped with a thermocouple and magnetic stir bar and then submerged in a water bath. Ruthenium(III) chloride hydrate (0.782 g, 3.47 mmol) was added followed by sodium periodate (33.75 g). The temperature rose from 17° C. to 22° C. After 35 minutes, a second aliquot of sodium periodate (33.75 g) was added and the temperature increased from 21° C. to 25° C. After 38 minutes, a third aliquot of sodium periodate (33.75 g) was added, and the temperature increased from 22° C. to 28° C. over 12 minutes. Ice was added to the water bath and once the mixture had cooled (approximately 8 minutes) a third aliquot of sodium periodate (35 g) was added. The temperature increased from 21° C. to 25° C. After stirring at room temperature overnight, sodium periodate (20 g) was added, and 4 hours later, another aliquot of sodium periodate (20 g) was added. After one hour, the mixture was stirred at room temperature with an overhead stirrer. Then the reaction mixture was filtered through a Büchner funnel and the filter cake was rinsed with ethyl acetate. The cake was dried overnight in the vacuum filtration apparatus.

The material was added to a large separatory funnel with water (1 L) and ethyl acetate (500 mL). Brine was added (50 mL). After 5 hours, the phases were separated and the organic phase was washed with 10% sodium bisulfite solution. After standing overnight, the phases were separated and the organic phase was washed with brine (1 L). After 30 minutes the organic phase was separated, dried over sodium sulfate, filtered and concentrated under a vacuum. The crude material was purified by flash column chromatography (1.5 kg silica gel column, gradient elution of 0% to 50% isopropanol in hexanes) to provide the title compound as a white foam.

The resulting 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid was dissolved in ethanol and transferred to a 500 mL pear shaped flask. The solvent was removed under a vacuum to provide a white solid. A solution of 60% ethanol in water (360 mL) was added and the mixture was heated to 90° C. to dissolve all of the material. The solution was slowly cooled and seeded at 50° C., 45° C., and 40° C. with approximately 5 mg of crystalline product but the material dissolved. The solution was seeded at 37° C. with approximately 5 mg crystalline product and the material did not dissolve. The material was slowly cooled to room temperature and placed in the freezer overnight. Crystals were collected by vacuum filtration through a Büchner funnel and washed with cold 60% ethanol in water (approximately 100 mL). The material was dried by pulling air through the filter bed for 4 hours to provide a white solid (80.6 g). The material was placed under a vacuum at room temperature for two days. Next, the material was placed on a rotary evaporator at 50° C. at 15 Torr (2 kPa) for 4 hours. It was then placed under a vacuum at 50° C. overnight. NMR analysis indicated 6 wt % ethanol was present in the sample.

A small portion of the sample (100 mg) was slurried in water (0.5 mL) overnight. The solid was collected by vacuum filtration and washed with water to provide a white solid. NMR analysis indicated that 2.9 wt % ethanol was present. The material was re-slurried in water (0.5 mL) overnight and collected by vacuum filtration to provide a white solid. NMR analysis indicated that 0.5 wt % ethanol was present. X-ray diffraction indicated that the material had become amorphous.

The remainder of the material was heated at 55° C. under a vacuum overnight. After cooling to room temperature, it was slurried in water (250 mL) and stirred mechanically. Aliquots were periodically removed and the solid was measured for ethanol content. After 40 hours, additional water (100 mL) was added and the material was stirred at room temperature for an additional 4.5 days. The material was collected by vacuum filtration to provide a white granular solid which was resuspended in water (350 mL) and mechanically stirred at room temperature for about 8 hours. The material was collected by vacuum filtration through a Büchner funnel to provide a white solid. The solid was dried by pulling air through the filter bed for 6 hours and then it was allowed sit open to the atmosphere in the hood overnight to provide a white solid containing 3.5 wt % ethanol.

Manual Polymorph Screening

Figure 7:
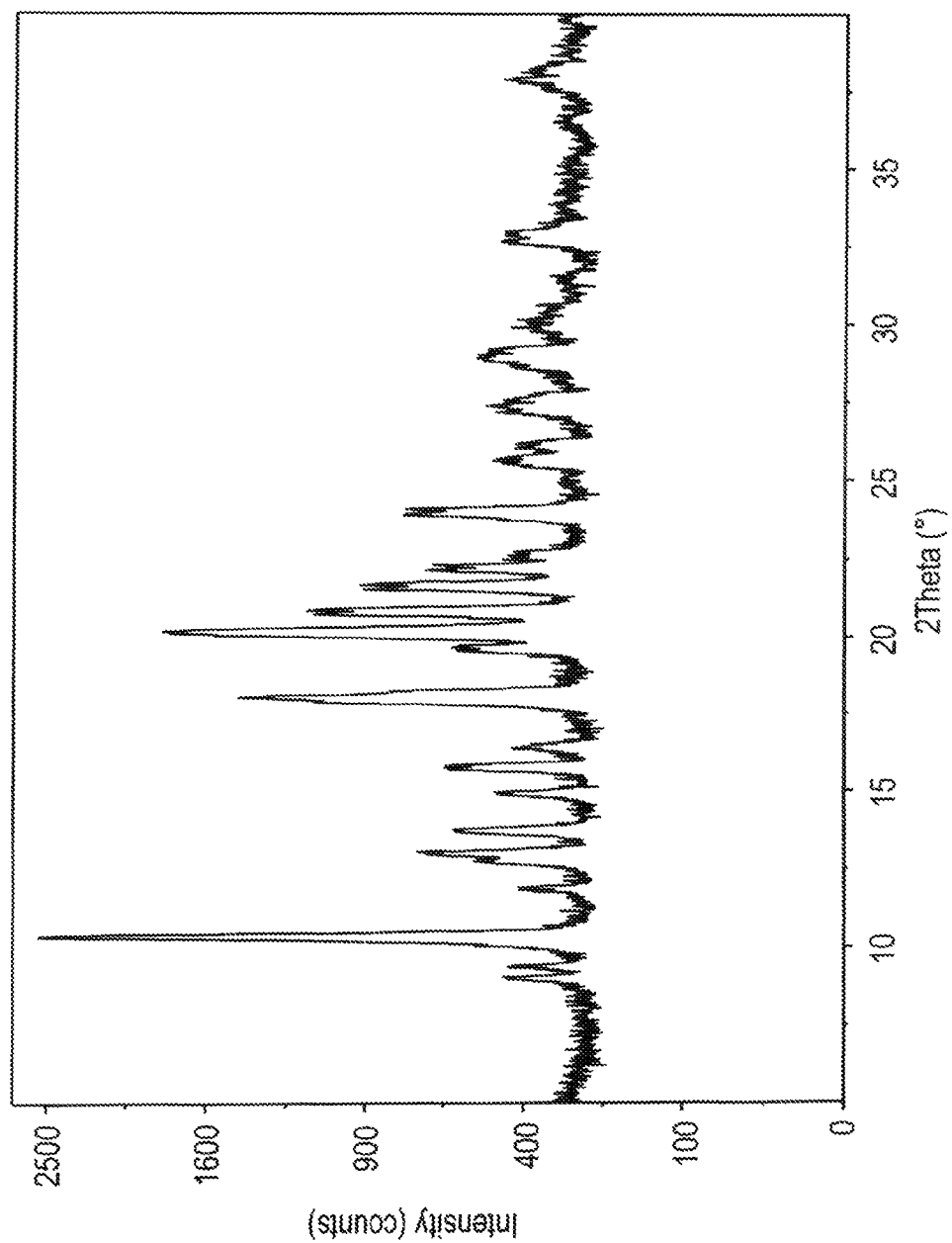
FIG. 7. XRPD Pattern of Compound A Propanol Solvate
Figure 8:
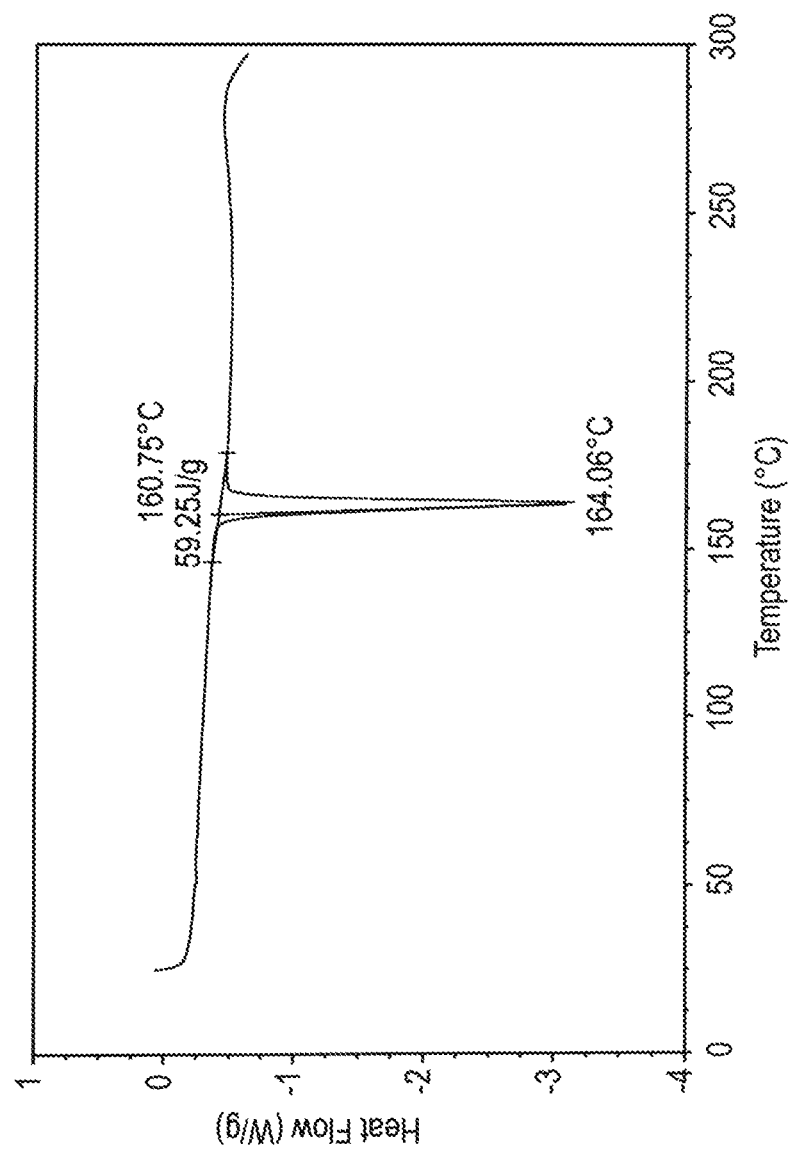
FIG. 8. DSC Curve of Compound A Crystalline Anhydrous
Figure 9:
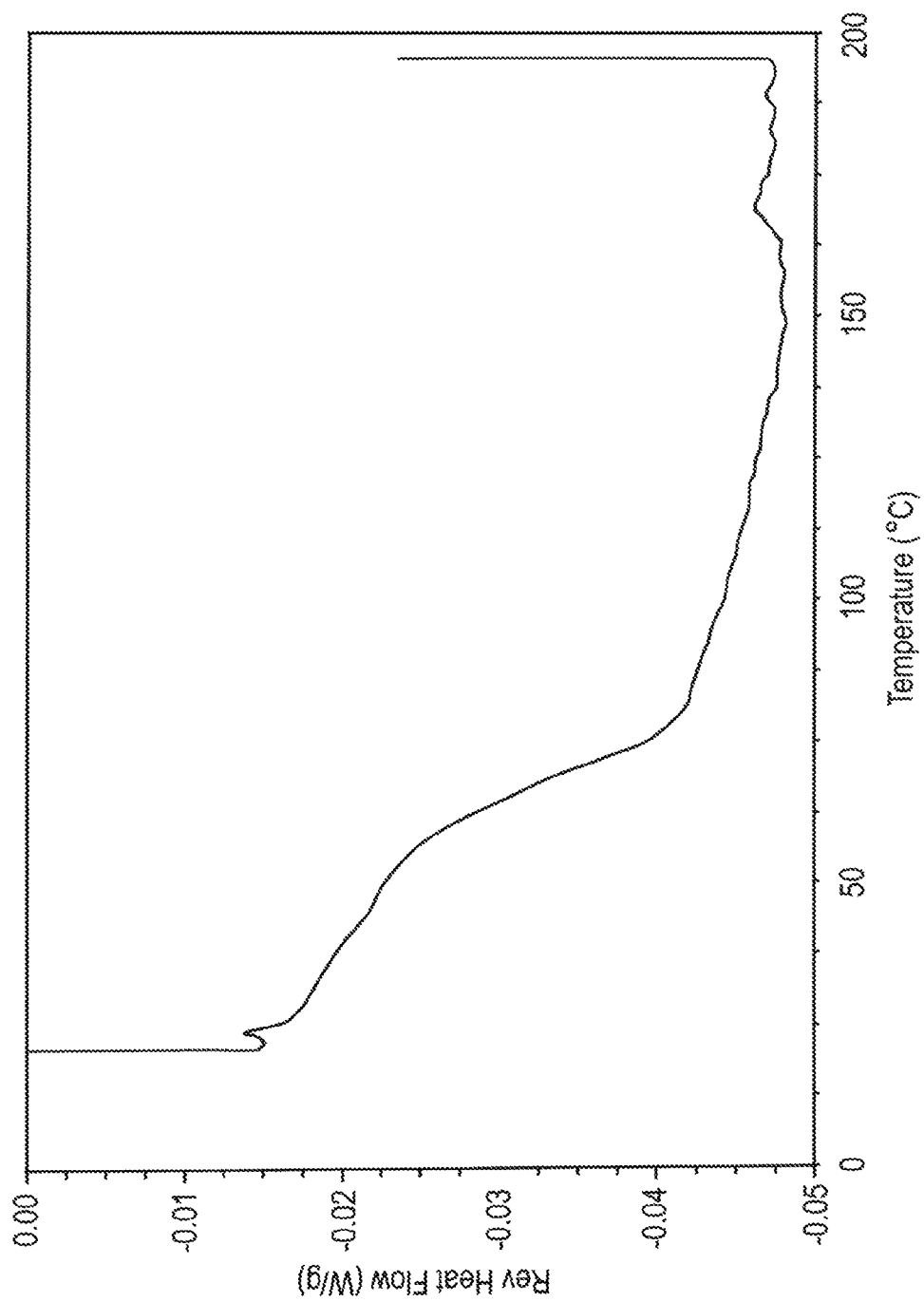
FIG. 9. DSC Curve of Compound A Amorphous
Figure 10:
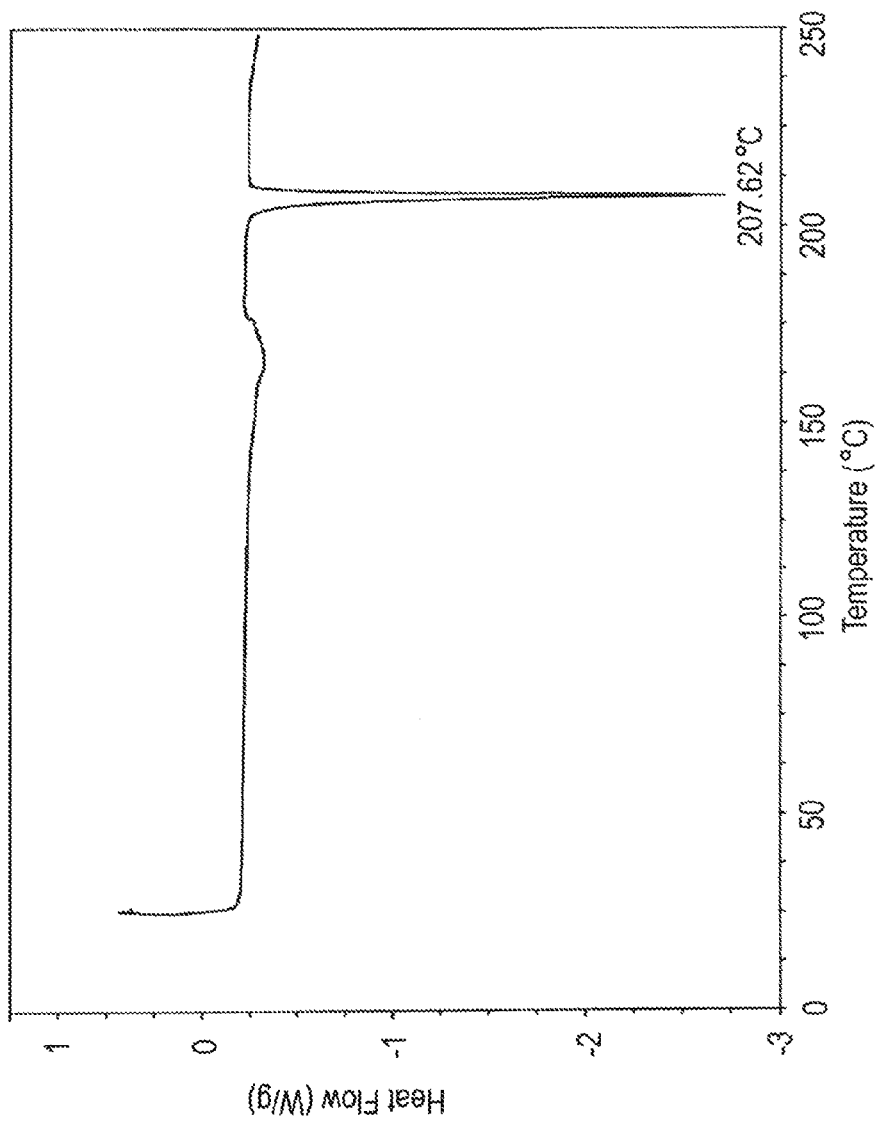
FIG. 10. DSC Curve of Crystalline (3S,5S,6R,8S)-8-allyl-6-(3-chlorophenyl)-5-(4-chlorophenyl)-3-isopropyl-8- methyl-2,3,5,6,7,8-hexahydrooxazolo [3,2-a]pyridin-4-ium naphthalene-1-sulfonate, hemi-toluene solvate FIG. 11. DSC Curve of Compound A Ethanolate FIG. 12. XRPD Pattern of Compound A DABCO Salt FIG. 13. DSC Curve of Compound A DABCO Salt.
Figure 11:
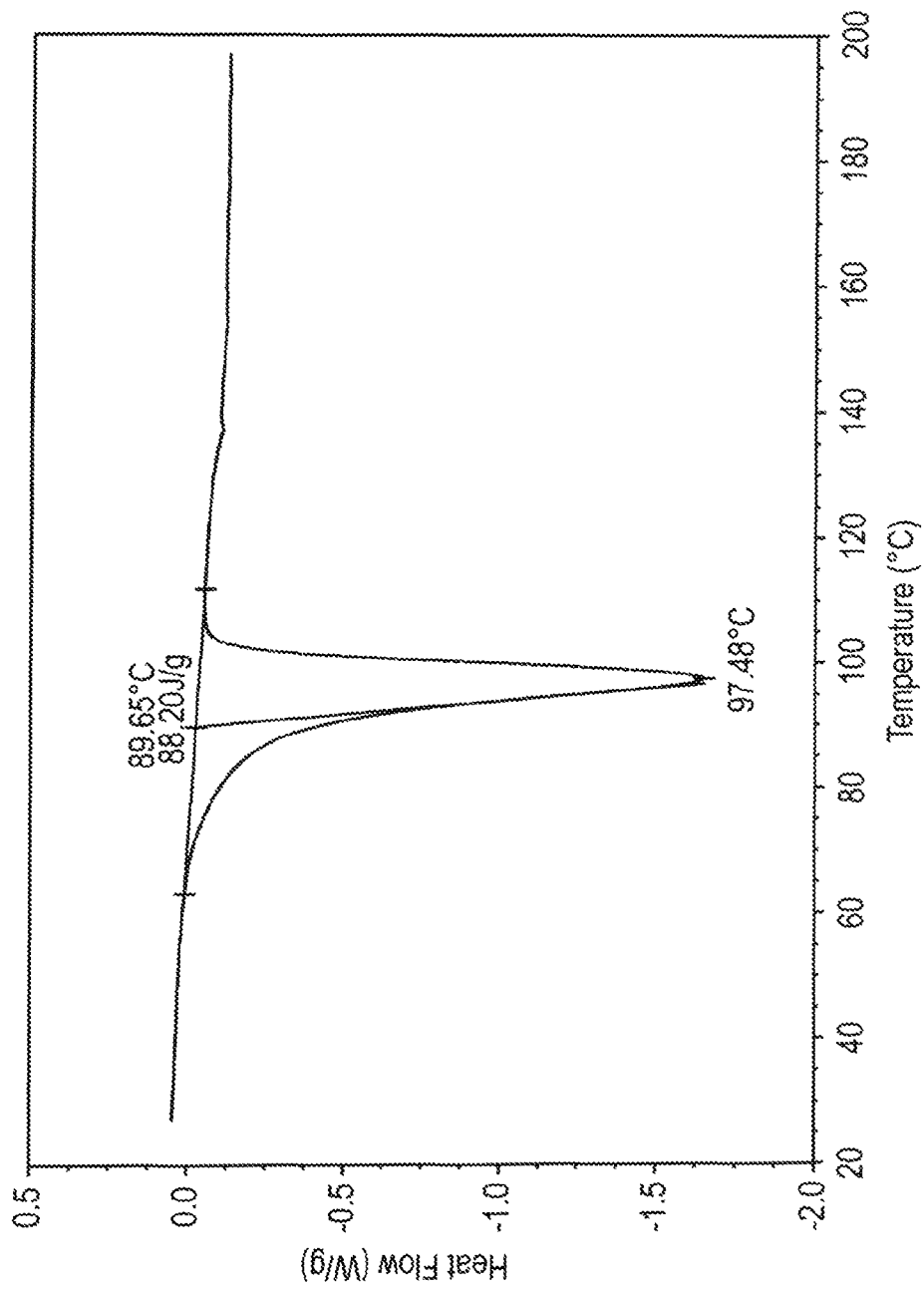
Figure 12:
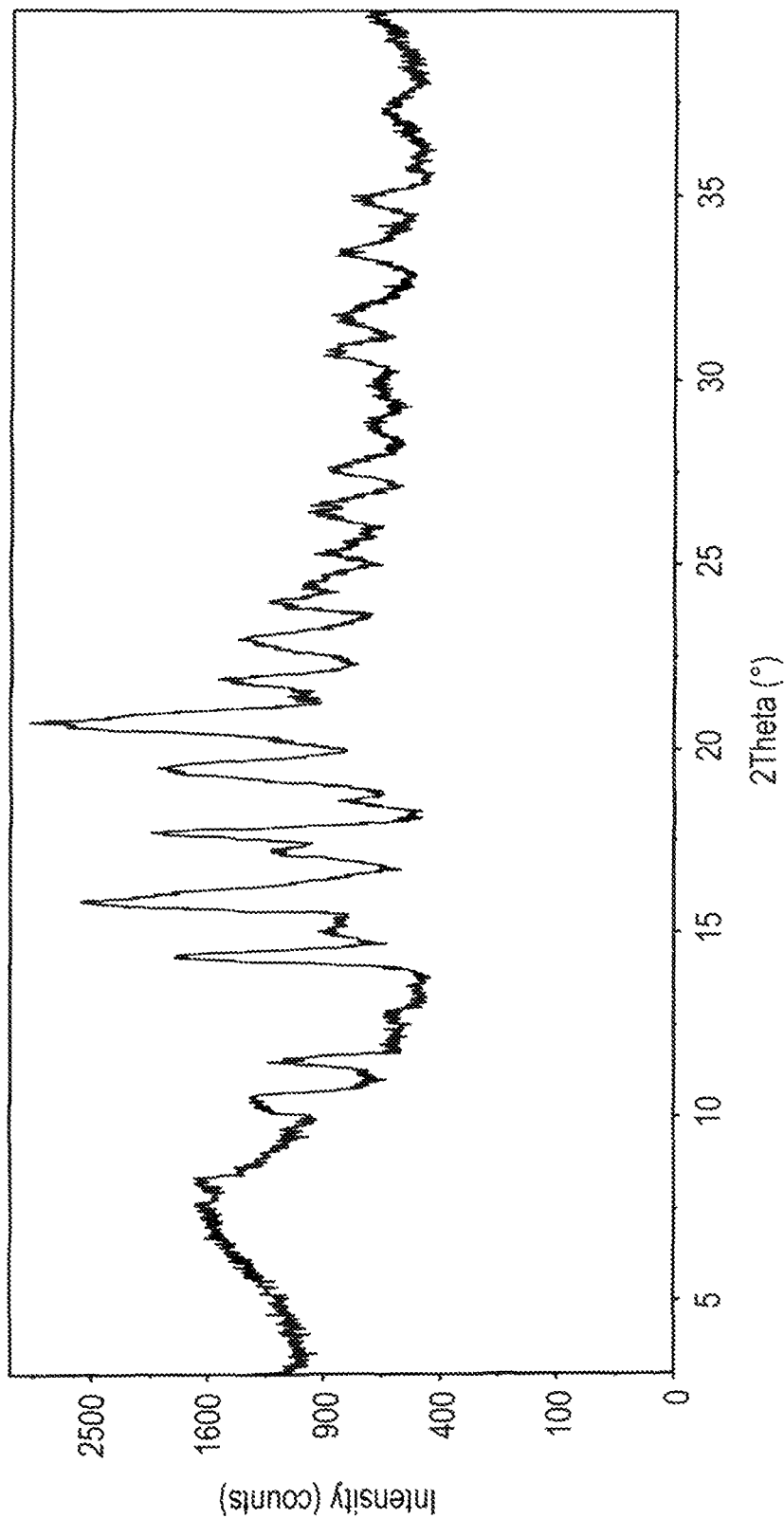
Figure 13:
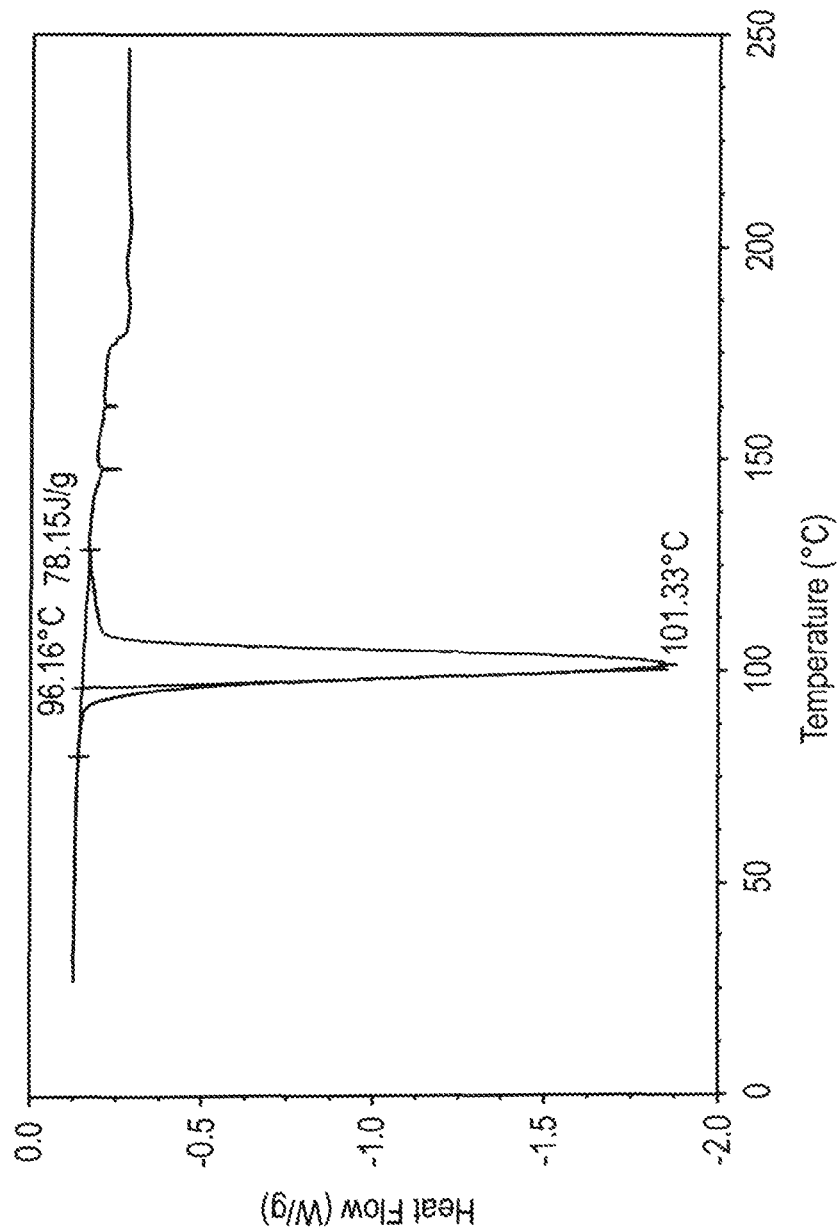

Samples were prepared according to the following general procedure. Approximately 20 mg of compound A ethanolate were weighted and added to a 1 dram vial. Solvent, 1 mL, was added to the vial. The samples were allowed to slurry. Solvents tested were water/ethanol (80/20, v/v), water/ethanol (70/30, v/v), water/ethanol (60/40, v/v), water/1-propanol (90/10, v/v), water/1-propanol (80/20, v/v), water/1-propanol (70/30, v/v), water/acetonitrile (95/5, v/v), water/acetonitrile (90/10, v/v), water/acetone (95/5, v/v), water/acetone (90/10, v/v), heptane, heptane/isopropyl acetate (99/1, v/v), cyclohexane, cyclohexane/isopropyl acetate (99/1, v/v). Observations were noted at the start of the experiment and on days 3, 7, 10, 13 and 19. Samples were analyzed by XRPD on days 7 and 10, 13, or 19. Results are given in Table 3. The XRPD was consistent with Compound A ethanolate (FIG. 6), Compound A Propanol Solvate (FIG. 7), Compound A Crystalline Anhydrous (FIG. 1) or Compound A Amorphous (FIG. 2).

TABLE 3

| Sample No. | Solvent | Crystalline | Form |
|---|---|---|---|
| 1 | water/ethanol (80/20, v/v) | Yes | Ethanolate |
| 2 | water/ethanol (70/30, v/v) | Yes | Ethanolate |
| 3 | water/ethanol (60/40, v/v) | Yes | Ethanolate |
| 4 | water/1-propanol (90/10, v/v) | Yes | Propanol Solvate |
| 5 | water/1-propanol (80/20, v/v) | Yes | Propanol Solvate |
| 6 | water/1-propanol (70/30, v/v) | Yes | Propanol Solvate |
| 7 | water/acetonitrile (95/5, v/v) | Yes | Crystalline Anhydrous |
| 8 | water/acetonitrile (90/10, v/v) | Yes | Crystalline Anhydrous |
| 9 | water/acetone (95/5, v/v) | Yes | Crystalline Anhydrous |
| 10 | water/acetone (90/10, v/v) | No | Amorphous |
| 11 | heptane | Yes | Crystalline Anhydrous |
| 12 | heptane/isopropyl acetate (99/1, v/v) | Yes | Crystalline Anhydrous |
| 13 | cyclohexane | Yes | Crystalline Anhydrous |
| 14 | cyclohexane/isopropyl acetate (99/1, v/v) | Yes | Crystalline Anhydrous |

Synthesis of Compound A Ethanolate 2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid

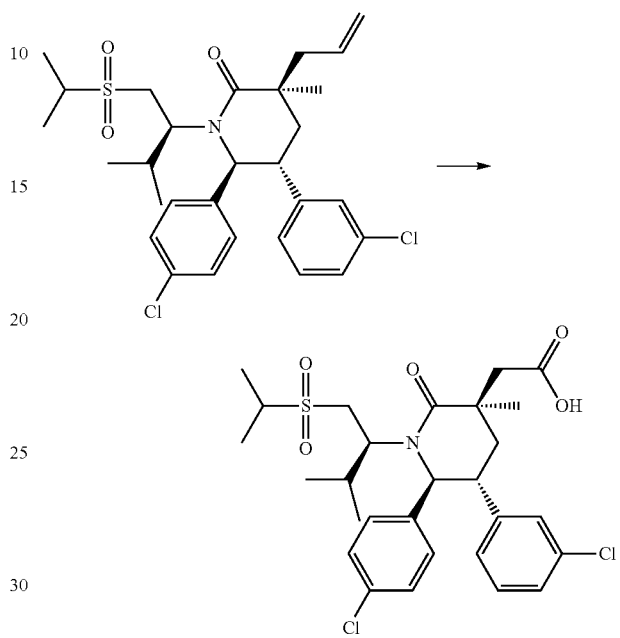

A number of batches were processed in series and combined for the final purification.

Batch 1:

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (80.6 g, 146 mmol) was dissolved in acetonitrile (280 mL) and ethyl acetate (280 mL) and transferred to a 2 L 3-neck Morton flask. Water (418 mL) was added. The flask was equipped with a thermocouple and submerged in a water bath. Ruthenium(III) chloride hydrate (0.726 g, 3.22 mmol) was added followed by sodium periodate (31.25 g). The temperature rose from 17° C. to 24° C., and ice was added to a water bath to control the temperature. After 15 minutes, a second aliquot of sodium periodate (31.25 g) was added and the temperature increased from 18° C. to 20° C. After 15 minutes a third aliquot of sodium periodate (31.25 g) was added and the temperature increased from 18° C. to 25.6° C. Additional ice was added to the water bath. After 10 minutes, a fourth aliquot of sodium periodate (31.25 g) was added. After stirring for two hours sodium periodate was added (15 g) and after 90 minutes sodium periodate (6 g) was added again. After one hour, the liquid was decanted into a large separatory funnel. The solid material was rinsed with ethyl acetate (1.5 L), added to the separatory funnel, and washed with 10% sodium bisulfite (1 L). The organic layer was washed with brine and the phases were allowed to separate overnight. The solid material was re-slurried with ethyl acetate (300 mL) and filtered. The filtrate was washed with 10% sodium bisulfite and brine. The combined organic layers were dried over sodium sulfate, filtered, and concentrated. The crude material was purified by flash column chromatography (1.5 kg silica gel column, gradient elution of 0% to 50% isopropanol in hexanes) to provide the title compound.

Batch 2:

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (90.4 g, 162 mmol) was dissolved in acetonitrile (308 mL) and ethyl acetate (308 mL) and transferred to a 2 L 3-neck Morton flask. Water (463 mL) was added. The flask was equipped with a thermocouple and a mechanical stirrer. Ruthenium(III) chloride hydrate (0.803 g, 3.56 mmol) was added and the reaction vessel was submerged in a cool water bath. Sodium periodate was added in portions (first portion: 34.0 g), and the temperature was monitored to keep the reaction mixture below 25° C. Ice was periodically added to the water bath to assist in temperature control.

After stirring for 12 minutes, a second portion was added (39.7 g), followed 28 minutes later by a third portion (36.6 g), and after 13 minutes, a forth portion (35.6 g). The mixture was stirred overnight at room temperature, and a fifth portion was added (15 g), and after 25 minutes, a sixth portion (16.5 g) was added. After about 15 minutes, the reaction mixture was decanted into a separatory funnel and the remaining solid was rinsed with ethyl acetate (2×1 L). The organics were collected and washed with 10% sodium bisulfite (1 L). The organic layer was washed with brine (1 L) and dried over sodium sulfate, filtered and concentrated. The crude material was purified by flash column chromatography (1.5 kg silica gel column, gradient elution of 0% to 20% isopropanol in hexanes) to provide the title compound.

Batch 3:

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (131.8 g, 239 mmol) was dissolved in acetonitrile (402 mL) and ethyl acetate (402 mL) and transferred to a 2 L 3-neck Morton flask. Water (603 mL) was added. The flask was equipped with a thermocouple and a mechanical stirrer. Ruthenium(III) chloride hydrate (1.079 g, 4.79 mmol) was added and the reaction vessel was submerged in a cool water bath. Sodium periodate was added in portions (first portion: 59 g), and the temperature was monitored to keep the reaction mixture below 25° C. Ice was periodically added to the water bath to assist in temperature control.

After stirring for 45 minutes, a second portion was added (50 g), followed 30 minutes later by a third portion (22 g), after 20 minutes by a forth portion (30 g), and after 20 minutes by a fifth portion (50 g). After stirring for two hours a sixth portion (20 g) was added, followed 20 minutes later by a seventh portion (10 g) and 20 minutes after that by an eighth portion (10 g). After 15 minutes, the reaction mixture was decanted into a separatory funnel and the remaining solid was rinsed with ethyl acetate (2×1 L). The organics were collected and washed with 10% sodium bisulfite (1 L). The organic layer was washed with brine (1 L) and dried over sodium sulfate, filtered and concentrated. To remove particulates, the material was dissolved in dichloromethane, filtered and concentrated. The crude material was divided into two portions and each was purified by flash column chromatography (1.5 kg silica gel column, gradient elution of 0% to 20% isopropanol in hexanes) to provide the title compound.

Batch 4:

(3S,5R,6S)-3-Allyl-5-(3-chlorophenyl)-6-(4-chlorophenyl)-1-((S)-1-(isopropylsulfonyl)-3-methylbutan-2-yl)-3-methylpiperidin-2-one (87.3 g, 159 mmol) was dissolved in acetonitrile (302 mL) and ethyl acetate (302 mL) and transferred to a 2 L 3-neck Morton flask. Water (453 mL) was added. The flask was equipped with a thermocouple and a mechanical stirrer. Ruthenium(III) chloride hydrate (0.786 g, 3.49 mmol) was added and the reaction vessel was submerged in a cool water bath. Sodium periodate was added in portions (first portion: 34.5 g), and the temperature was monitored to keep the reaction mixture below 25° C. Ice was periodically added to the water bath to assist in temperature control.

After stirring for 1 hour, a second portion was added (34.4 g), followed 30 minutes later by a third portion (34.5 g), and after 30 minutes by a forth portion (34.5 g). The maximum temperature was 27° C. After stirring for 3.5 hours a fifth portion (20 g) was added, followed 1 hour later by a sixth portion (5 g). After 15 minutes, the reaction mixture was decanted into a reparatory funnel and the remaining solid was rinsed with ethyl acetate (2×1 L). The organics were collected and washed with 10% sodium bisulfite (1 L). The organic layer was washed with brine (0.5 L) and dried over sodium sulfate, filtered and concentrated. The crude material was purified by flash column chromatography (Biotage SNAP cart, 1.5 kg silica gel column, gradient elution of 0% to 50% isopropanol in hexanes) to provide the title compound. Impure fractions were repurified by flash column chromatography (1.5 kg silica gel column, gradient elution of 0% to 20% isopropanol in hexanes) to provide the title compound.

Batch 5:

Impure fractions from Batches 1 through 4 were repurified by multiple iterations of flash column chromatography (amount of silica gel varied from 330 g to 1.5 kg, gradient elution of 0% to 20% isopropanol in hexanes) to provide the title compound.

Final Purification:

Material from Batches 1 through 5 were combined with a portion of the material from another synthesis, 18 g. 2-((3R,5R,6S)-5-(3-Chlorophenyl)-6-(4-chlorophenyl)-1-((S)-1-(isopropylsulfonyl)-3-methylbutan-2-yl)-3-methyl-2-oxopiperidin-3-yl)acetic acid (400 g) was dissolved in ethanol and concentrated under a vacuum to provide a white crystalline solid. A solution of 60% ethanol in water (1900 mL) was added and the mixture was heated to 80° C. while rotating on a rotary evaporator at atmospheric pressure. After the material had dissolved, the solution was slowly cooled while mechanically stirring the flask. After 3 hours, the temperature had cooled to 50° C. and the material was seeded with crystalline 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid. The solid completely dissolved. After 30 minutes, the solution was re-seeded (45° C.) and the material began to slowly crystallize. Once the mixture had cooled to room temperature, it was placed in the freezer overnight. The crystals were collected by vacuum filtration through a Büchner funnel. The filter cake was washed with ice-cold 60% ethanol in water and dried under a vacuum on the Büchner funnel to provide a white solid. NMR analysis indicated that 7.8 wt % ethanol was present (1 molar equivalent). Water (deionized and filtered (Milli-Q filtration system, EMD Millipore, Billerica, Mass.)) was added to the solid and the mixture was mechanically stirred at room temperature overnight. Aliquots were periodically removed to monitor the ethanol content of the solid. After three days, the material was vacuum filtered through a Büchner funnel, washed with water (deionized and filtered as described above) and dried by pulling a vacuum through the filter cake for 3 hours. The filter cake was air-dried for two days in the funnel, then, it was transferred to a 2 L flask as a white solid and dried under a vacuum overnight. NMR analysis indicated that 6.2 wt % ethanol was present.
The XRPD pattern was consistent with Compound A ethanolate (FIG. 6).

$^1$H NMR (500 MHz, DMSO-d$_6$, δ ppm): 12.43 (br s, 1H), 7.72 (br, 1H), 7.37 (br, 2H), 7.23 (t, J=7.8 Hz, 1H), 7.17 (d, J=8.1 Hz, 1H), 7.02 (t, J=1.9, 1.9 Hz, 1H), 6.99 (br, 1H), 6.98 (dt, J=7.7, 1.4, 1.4 Hz, 1H), 5.01 (d, J=11.2 Hz, 1H), 3.84 (dd, J=14.0, 10.1 Hz, 1H), 3.59 (ddd, J=13.7, 11.3, 2.9 Hz, 1H), 3.39 (m, 1H), 3.18 (dd, J=13.9, 1.3 Hz, 1H), 3.06 (ddd, J=10.6, 8.1, 1.6 Hz, 1H), 2.95 (d, J=13.7 Hz, 1H), 2.50 (d, J=13.8 Hz, 1H), 2.12 (t, J=13.5 Hz, 1H), 2.10 (m, 1H), 2.03 (dd, J=13.3, 3.0 Hz, 1H), 1.29 (d, J=6.8 Hz, 3H), 1.29 (d, J=6.8 Hz, 3H), 1.23 (s, 3H), 0.55 (d, J=6.6 Hz, 3H), 0.37 (d, J=6.9 Hz, 3H); MS (ESI)=568.2 [M+H]$^+$.

Synthetic procedures for making 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (Compound A)

Scheme 1-Procedure 1

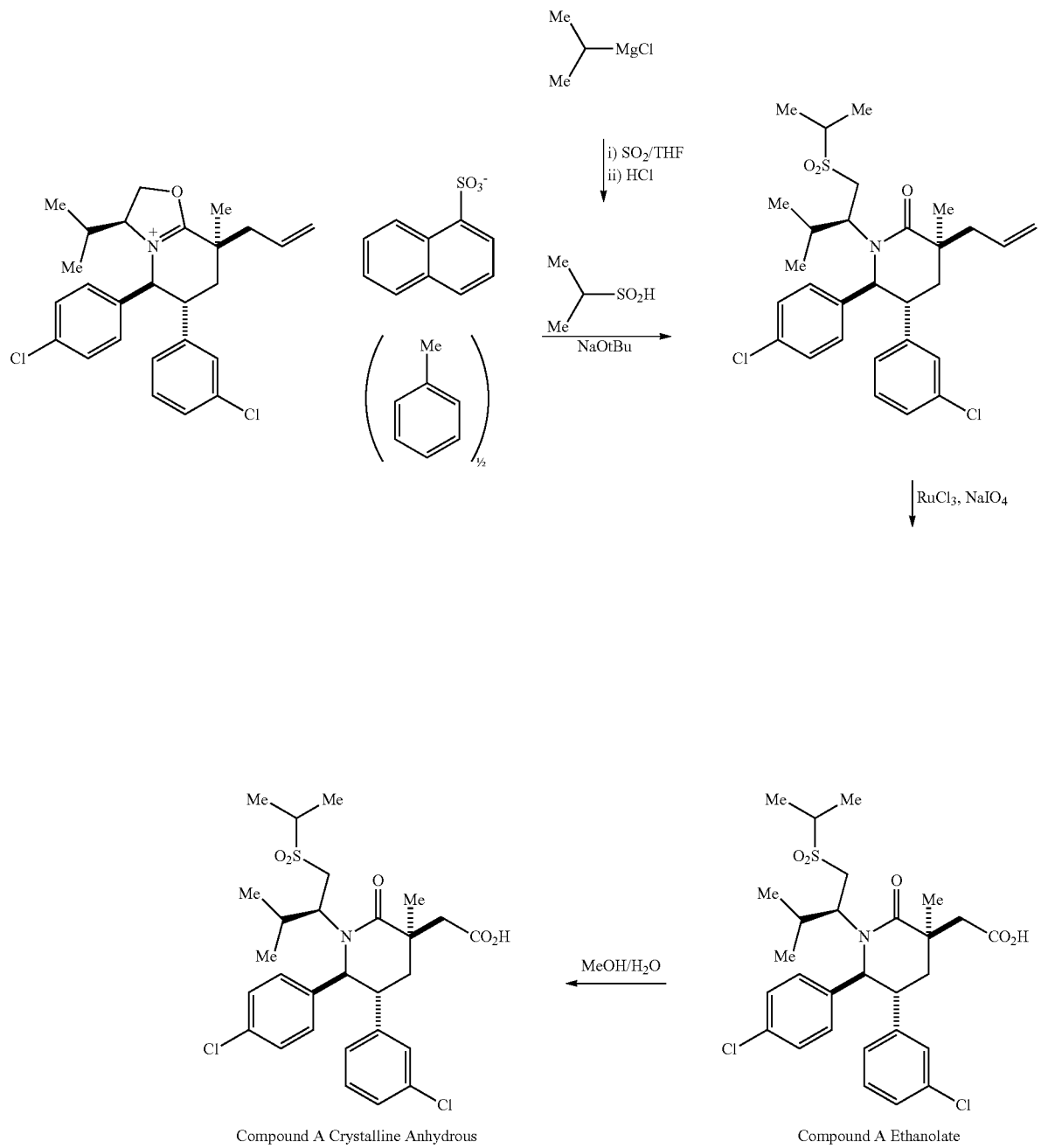

Compound A Crystalline Anhydrous

Compound A Ethanolate

Preparation of Propane-2-Sulfinic Acid:

Tetrahydrofuran (20 L) was added to a reaction vessel and the temperature of the vessel was cooled to −50° C. Sulfur dioxide (3.5 kg, 54.6 mol) was condensed in the reaction vessel at −50° C. Isopropyl magnesium chloride (2M in tetrahydrofuran, 21 L, 42 mol) was added to the solution. The reaction mixture was agitated for 30 min at −10° C. and aqueous 2.5 N hydrochloric acid (18.5 l, 46.2 mol) was added. The reaction mixture was warmed to 20° C. and t-butylmethyl ether (10 L) was added. The phases were separated and the aqueous phase was extracted twice with t-butylmethyl ether (10 L). The combined organic extracts were washed with aqueous sodium chloride (12 wt %, 20 mL) and concentrated under reduced pressure to afford the desired sulfinic acid in 82% yield (3.7 Kg).

Preparation of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one To a solution of propane-2-sulfinic acid (912 g, 8.4 mol) in toluene (7.5 L) was added tetrahydrofuran (3.6 L). Sodium t-butoxide (2M in tetrahydrofuran, 3.6 L, 7.2 mol) was added while maintaining the temperature of the mixture below 20° C. The pH of the mixture was measured to be approximately 6. The mixture was distilled under atmospheric pressure to produce a distillate mass of 6.6 Kg. (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium naphthalene-1-sulfonate, hemi-toluene solvate (also called the "oxoiminium salt, hemi-toluene solvate" herein) (3.62 Kg, 5.2 mol) and toluene (7.8 L) were added, maintaining the temperature of the mixture below 30° C. The mixture was distilled under atmospheric pressure to produce a distillate mass of 7.2 Kg while simultaneously adding dimethylacetamide (10.9 L). The mixture was agitated at approximately 120° C. for 14 h and cooled to 25° C. t-Butylmethyl ether (9.1 L) and water (14.5 L) were added to the mixture and the biphasic mixture was agitated until no solids were visible. The phases were separated. The organic phase was washed with water (7.3 L) and aqueous saturated sodium bicarbonate (7.1 L). The organic phase was filtered and distilled under reduced pressure to produce a distillate mass of 15 Kg while simultaneously adding acetonitrile (21.3 L). Water (2 L) was added and the solution was seeded with (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (160 g, 0.29 mol) at 25° C. (The seed material was prepared via the same process in a previously conducted smaller scale experiment). The mixture was agitated at 25° C. for 25 min and cooled to 20° C. over approximately 45 min. A mixture of acetonitrile (3.0 L) and water (7.0 L) was added to the reaction mixture over 1.5 h. The resultant mixture was agitated for 1 h and filtered. The product was washed with a mixture of acetonitrile (3.6 L) and water (2.4 L). The product was dried under nitrogen to afford (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (2.9 Kg) in 86% yield.

Preparation of Compound A Ethanolate:

To a solution of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (2.4 Kg, 4.4 mol) in ethyl acetate (8.4 L), acetonitrile (8.6 L), and water (6.5 L) was added ruthenium chloride hydrate (20.5 g, 0.09 mol). Sodium periodate (5.0 kg, 23.2 mol) was added in four 4 equal portions over the course of 1.5 h, maintaining the temperature of the mixture between 20° C. and 28° C. The mixture was agitated for 2.5 h and filtered through a layer of diatomaceous earth (3.33 Kg). The resulting diatomaceous earth cake was washed with isopropyl acetate (10.4 L) and water (3 L). The filtrate was phase separated. The organic phase was washed twice with an aqueous sodium chloride solution (25 wt %, 5.5 L), washed twice with an aqueous sodium chloride and sodium bisulfite solution (25 wt % sodium chloride and 20 wt % sodium bisulfite, 7.8 L), and once with an aqueous sodium chloride solution (25 wt %, 6.5 L). The organic phase was distilled under reduced pressure while simultaneously adding isopropyl acetate (12.4 L). The batch was filtered. Charcoal (680 g) was added and the mixture was agitated for 13 h. The mixture was filtered through a layer of diatomaceous earth (1.5 Kg) and the diatomaceous earth cake was washed with isopropyl acetate (8 L). The solution was distilled under reduced pressure to produce a distillate mass of 24.5 Kg while simultaneously adding ethanol (16 L). Heptane (8.5 L) was added and the solution was seeded with Compound A Ethanolate (The seed material was prepared via the same process in a previously conducted smaller scale experiment) (95 g). The mixture was agitated at 20° C. for 40 min and distilled under reduced pressure to produce a distillate mass of 10.9 Kg while simultaneously adding heptane (8.8 L). The mixture was agitated for 12 h and filtered. The product was washed with a mixture ethanol (0.4 L) and heptane (1.6 L). The product was dried under nitrogen to afford Compound A Ethanolate (1.99 Kg) in 70% yield.

Preparation of Compound A Crystalline Anhydrous:

Compound A Ethanolate (1.0 Kg, 1.62 mol) was dissolved in methanol (8.5 L) and the resultant solution was filtered. The solution was warmed to 35° C. and water (2.5 L) was added. The solution was seeded with Compound A Crystalline Anhydrous (50 g, 0.074 mol) and cooled to 20° C. over the course of 4 h (The seed material was prepared via the same process in a previously conducted smaller scale experiment). Water (2 L) was added over the course of 30 min. The mixture was agitated for 30 min and filtered. The product was dried under nitrogen to afford Compound A Crystalline Anhydrous (0.86 Kg) in 93% yield.

$^1$H NMR (400 MHz, DMSO-$d_6$) δ 12.37 (s, 1H), 7.36 (bs, 4H), 7.23 (t, 1H, J=7.9 Hz), 7.16 (ddd, 1H, J=7.9, 1.9, 1.0 Hz), 7.02 (t, 1H, J=1.9 Hz), 6.98 (bd, 1H, J=7.9 Hz), 5.02 (d, 1H, J=7.9 Hz), 3.84 (dd, 1H, J=13.4, 10.2 Hz), 3.58 (ddd, 1H, J=13.5, 11.3, 3.0 Hz), 3.39 (spt, 1H, J=6.8 Hz), 3.17 (bd, 1H, J=13.4 Hz), 3.07 (bt, 1H, J=8.6 Hz), 2.95 (d, 1H, J=13.9 Hz), 2.51 (d, 1H, J=13.9 Hz), 2.13 (bt, 1H, J=13.5 Hz), 2.11 (spt, 1H, J=6.8 Hz), 2.04 (dd, 1H, J=13.5, 3.0 Hz), 1.30 (2×d, 6H, J=6.8 Hz), 1.24 (s, 3H), 0.56 (d, 3H, J=6.8 Hz), 0.38 (d, 3H, J=6.8 Hz); Exact Mass $[C_{28}H_{36}Cl_2NO_5S]^+$: calculated=568.1691, measured M/Z [M+1]=568.1686.

It is noted that when seed crystals are used in the procedures set forth in this application, the seed crystals can be obtained by following the procedures set forth herein, typically on a smaller scale, to obtain seed crystals for the larger scale syntheses.

Scheme 2-Procedure 2

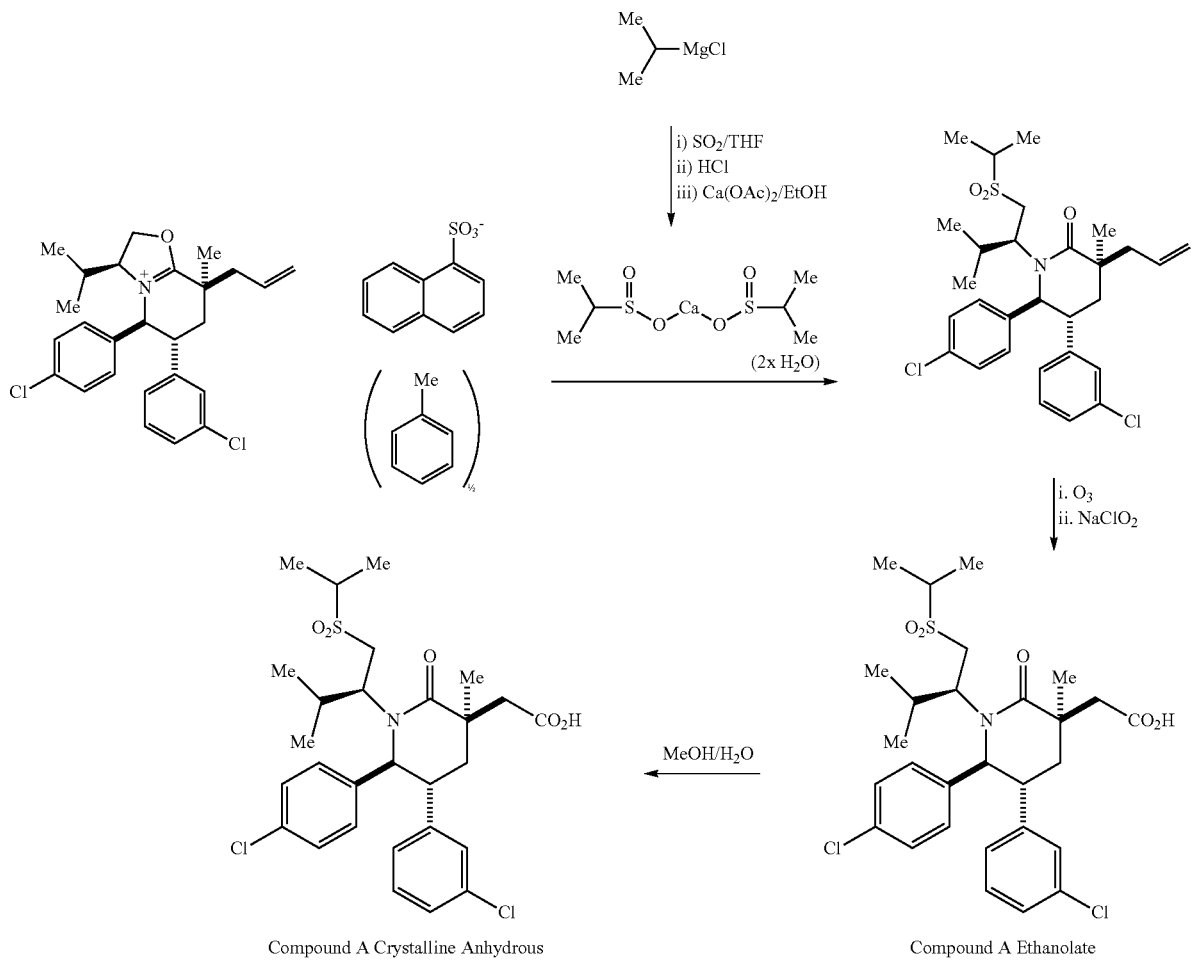

Preparation of Calcium Propane-2-Sulfinate Dihydrate:

Tetrahydrofuran (20 L) was added to a reaction vessel and the temperature of the vessel was cooled to −50° C. Sulfur dioxide (3.5 kg, 54.6 mol) was condensed in the reaction vessel at −50° C. Isopropyl magnesium chloride (2M in tetrahydrofuran, 21 L, 42 mol) was added to the solution. The reaction mixture was agitated for 30 min at −10° C. and aqueous 2.5 N hydrochloric acid (18.5 l, 46.2 mol) was added. The reaction mixture was warmed to 20° C. and t-butylmethyl ether (10 L) was added. The phases were separated and the aqueous phase was extracted twice with t-butylmethyl ether (10 L). The combined organic extracts were washed with aqueous sodium chloride (12 wt %, 20 mL) and concentrated under reduced pressure to afford the desired propane-2-sulfinic acid in 82% yield (3.7 Kg). The propane-2-sulfinic acid was dissolved in ethanol (37 L) and a solution of calcium acetate monohydrate (3.0 Kg, 17.1 mol) in water (7.2 L) was added. The resultant mixture was agitated for 1 h and filtered. The product was washed with a mixture of ethanol (10.8 L) and water (1.1 L). The product was dried under nitrogen to afford calcium propane-2-sulfinate dihydrate in 86% yield (4.26 Kg). $^1$H NMR (400 MHz, DMSO-d6) δ 3.37 (s, 4H), 1.88 (spt, 2H, J=7.0 Hz), 0.92 (d, 12H, J=7.0 Hz).

Preparation of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one Calcium propane-2-sulfinate dihydrate (2943616) (2.7 Kg, 9.36 mol) and toluene (22 L) were added to a 60 L vessel. The reaction mixture was warmed to 110° C. and distilled under reduced pressure to produce a distillate mass of 50 Kg while simultaneously adding toluene (43 L). The reaction mixture was cooled to 40° C. and (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium naphthalene-1-sulfonate, hemi toluene solvate (3.6 Kg, 5.2 mol) and toluene (9.0 L) were added. The reaction mixture was warmed to 110° C. and distilled under atmospheric pressure to produce a distillate mass of 15.8 Kg while simultaneously adding dimethylacetamide (10.9 L). The mixture was agitated at approximately 120° C. for 14 h and cooled to 40° C. t-Butylmethyl ether (9.1 L) and water (14.5 L) were added to the mixture and the biphasic mixture was agitated until no solids were visible. The phases were separated. The organic phase was washed twice with water (2×7.3 L), once with aqueous saturated sodium bicarbonate (7.1 L), and once with an aqueous sodium chloride (12 wt %, 7.1 L). The organic phase was cooled to 20° C., filtered, and distilled under reduced pressure to produce a distillate mass of 15 Kg while simultaneously adding acetonitrile (21.3 L). Water (2 L) was added. The solution was seeded with (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (160 g, 0.29 mol) at 25° C. The mixture was agitated at 25° C. for 25 min and cooled to 20° C. over approximately 45 min (The seed material was prepared via the same process in a previously conducted smaller scale experiment). A mixture of acetonitrile (3.0 L) and water (7.0 L) was added to the reaction mixture over 1.5 h. The resultant mixture was agitated for 1 h and filtered. The product was washed with a mixture of acetonitrile (3.6 L) and water (2.4 L). The product was dried under nitrogen to afford (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (2.8 Kg) in 83% yield.

Preparation of Compound A Ethanolate:

A solution of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (1.6 Kg, 2.9 mol) in a mixture of water (2.4 L) and acetonitrile (21.6 L) was allowed to flow through the continuous stirred-tank reactor ozone vessel (1 L vessel) at a flow rate of 60 mL/min at 20° C. (alternatively, the ozonolysis was performed in a reaction vessel using an ozone sparger). The reaction mixture was added to a solution of sodium chlorite (80 wt %, 1.0 Kg, 11.6 mol) in water (5.6 L) over the course of 6 h (alternatively, the aqueous solution of sodium chlorite was added to the reaction mixture). The reaction mixture was agitated for 16 h and a solution of sodium bisulfite (1.2 Kg, 11.6 mol) in water (5.6 L) was added over the course of 2 h. The mixture was agitated for 1 h and the phases were separated. To the organic phases were added isopropyl acetate (8 L) and water (8 L). The mixture was agitated for 30 min and the phases were separated. The organic phase was washed once with aqueous sodium chloride (6 wt %, 8 L), three times with aqueous 1M sodium phosphate (pH 6, 8 L), and once with aqueous sodium chloride (6 wt %, 8 L). The organic phase was filtered. The mixture was distilled under reduced pressure to produce a distillate mass of 35 Kg while simultaneously adding isopropyl acetate (32 L). The mixture was distilled under reduced pressure to produce a distillate mass of 36 Kg while simultaneously adding ethanol (32 L). Heptane was added (9.6 L) and the mixture was distilled under reduced pressure to produce a distillate mass of 5 Kg. The mixture was seeded with Compound A Ethanolate (80 g, 0.13 mol) (The seed material was prepared via the same process in a previously conducted smaller scale experiment). Heptane (6.4 L) was added over the course of 1 h, the mixture was agitated for 12 h, cooled to 15° C., and filtered. The product was washed with a mixture of ethanol (90 mL) and heptane (4.8 L). The product was dried under nitrogen to afford Compound A Ethanolate (1.33 Kg) in 81% yield.

Preparation of Compound A Crystalline Anhydrous:

Compound A Ethanolate (1.0 Kg, 1.62 mol) was dissolved in methanol (8.5 L) and the resultant solution was filtered. The solution was warmed to 35° C. and water (2.5 L) was added. The solution was seeded with Compound A Crystalline Anhydrous (50 g, 0.074 mol) and cooled to 20° C. over the course of 4 h (The seed material was prepared via the same process in a previously conducted smaller scale experiment). Water (2 L) was added over the course of 30 min. The mixture was agitated for 30 min and filtered. The product was dried under nitrogen to afford Compound A Crystalline Anhydrous (0.86 Kg) in 93% yield.

$^1$H NMR (400 MHz, DMSO-$d_6$) δ 12.37 (s, 1H), 7.36 (bs, 4H), 7.23 (t, 1H, J=7.9 Hz), 7.16 (ddd, 1H, J=7.9, 1.9, 1.0 Hz), 7.02 (t, 1H, J=1.9 Hz), 6.98 (bd, 1H, J=7.9 Hz), 5.02 (d, 1H, J=7.9 Hz), 3.84 (dd, 1H, J=13.4, 10.2 Hz), 3.58 (ddd, 1H, J=13.5, 11.3, 3.0 Hz), 3.39 (spt, 1H, J=6.8 Hz), 3.17 (bd, 1H, J=13.4 Hz), 3.07 (bt, 1H, J=8.6 Hz), 2.95 (d, 1H, J=13.9 Hz), 2.51 (d, 1H, J=13.9 Hz), 2.13 (bt, 1H, J=13.5 Hz), 2.11 (spt, 1H, J=6.8 Hz), 2.04 (dd, 1H, J=13.5, 3.0 Hz), 1.30 (2×d, 6H, J=6.8 Hz), 1.24 (s, 3H), 0.56 (d, 3H, J=6.8 Hz), 0.38 (d, 3H, J=6.8 Hz); Exact Mass [$C_{28}H_{36}Cl_2NO_5S$]$^+$: calculated=568.1691, measured M/Z [M+1]=568.1686. An XRPD pattern representative of compound A crystalline anhydrous is shown in FIG. 1.

An alternative route to a make compound A crystalline anhydrous is to make a DABCO salt instead of the ethanolate as shown in Scheme 3.

Scheme 3-DABCO Salt Process

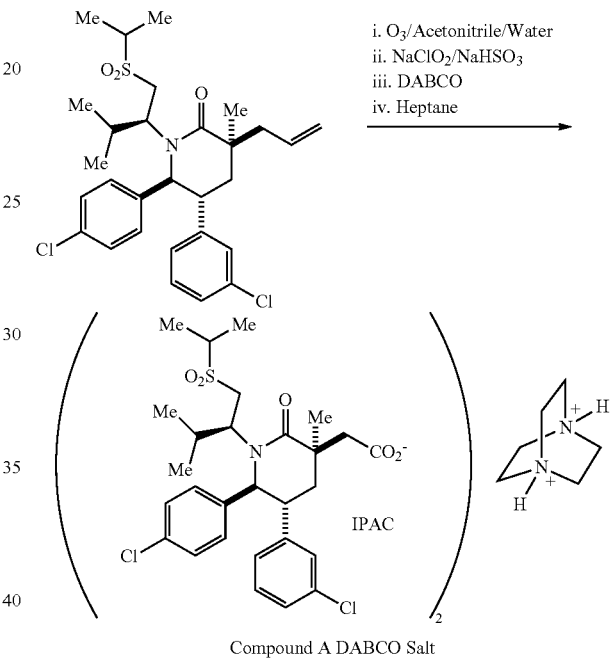

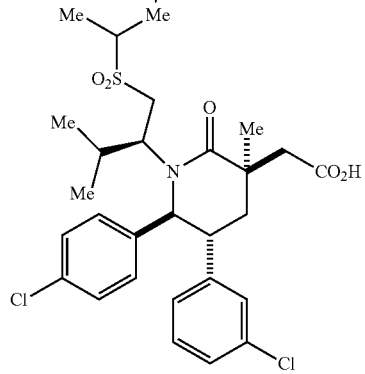

Compound A Crystalline Anhydrous

Preparation of Compound A DABCO Salt:

Ozone was delivered to an agitated solution of (3S,5R,6S)-3-allyl-5-(3-chlorophenyl)-6-(4-chlorophenyl)-1-((S)-

1-(isopropylsulfonyl)-3-methylbutan-2-yl)-3-methylpiperidin-2-one (4.0 Kg, 7.27 mol) in a mixture of water (6 L) and acetonitrile (54 L) using a subsurface C22 Hastelloy sparger at 20° C. over the course of ten hours. An aqueous solution of sodium chlorite (80 wt %, 2.5 Kg, 29 mol) in water (14 L) was added over the course of 1 h, maintaining the temperature of the mixture below 40° C. The reaction mixture was agitated for 12 h and a solution of sodium bisulfite (3.0 Kg, 29 mol) in water (14 L) was added over the course of 2 h, maintaining the temperature of the reaction mixture below 40° C. The mixture was agitated for 1 h and the phases were separated. To the organic phases were added isopropyl acetate (IPAC) (20 L) and 1M aqueous sodium phosphate pH 6 (8 L). The mixture was agitated for 30 min and the phases were separated. The organic phase was washed with 1M aqueous sodium phosphate pH 6 (20 L) and with 1M aqueous sodium chloride (20 L). The mixture was distilled under reduced pressure to produce a distillate mass of 75 Kg while simultaneously adding isopropyl acetate (80 L). The water content of the solution by Karl Fisher was less than one percent. The organic phase was filtered. The solution was further distilled to a volume of approximately 16 L. The solution was heated to 55° C. and 1,4-diazabicyclo [2.2.2]octane (DABCO, 424 g, 3.65 mol) was added. (3S, 5R,6S)-3-allyl-5-(3-chlorophenyl)-6-(4-chlorophenyl)-1-((S)-1-(isopropylsulfonyl)-3-methylbutan-2-yl)-3-methylpiperidin-2-one 1,4-diazabicyclo[2.2.2]octane (DABCO) salt seeds (136 g, 0.18 mol) were added as a slurry in isopropyl acetate and heptane (1/1, 800 mL). The mixture was agitated at 55° C. for 20 minutes and cooled to 20° C. over the course of 2 h. Heptane was added (16.8 L) over the course of 1 h and the mixture was agitated at 20° C. for 12 h. The product was filtered and the filter cake was washed once with a mixture of isopropyl acetate and heptane (2/3, 21 L) and once with a mixture of isopropyl acetate and heptane (1/4, 21 L). The product was dried under nitrogen to afford Compound A DABCO Salt (4.64 Kg) in 87% yield (100% liquid chromatography area percent (LCAP), 78.9 wt % Compound A). The compound A DABCO salt is a solvate of isopropyl acetate (IPAC) in accordance with Scheme 3. The Compound A DABCO Salt is the better performing purification control point to enhance the purity of the drug substance (Compound A). Typically, the purity of crude reaction mixtures of 97 to 99 liquid chromatography area percent purity can be improved to 100 liquid chromatography area percent purity (no impurity at greater level than 0.05 liquid chromatography area percent) using the crystallization of the DABCO salt. For comparison, enhancement of purity of the drug substance (Compound A) using Compound A Ethanolate as a control point allows for crude reaction mixtures of 97 to 99 liquid chromatography area percent purity to be improved to 99.5 to 99.6 liquid chromatography area percent purity (and multiple impurities are present in the filtered material at greater levels than 0.05 liquid chromatography area percent).

$^1$H NMR (400 MHz, CDCl$_3$): δ ppm 0.49 (d, J=6.8 Hz, 6H), 0.64 (d, J=6.4 Hz, 6H), 1.23 (d, J=6.0 Hz, 12H), 1.41 (s, 6H), 1.43 (d, J=7.6 Hz, 12H), 2.02 (s, 6H), 2.05-2.00 (m, 2H), 2.30-2.15 (m, 4H), 2.71 (d, J=13.2, 2H), 2.84 (dd, J=2.0, 13.6, 2H), 2.90 (d, J=13.6 Hz, 2H), 2.96 (s, 12H), 3.11 (pent, J=6.8 Hz, 2H), 3.67-3.22 (m, 2H), 3.55-3.48 (m, 2H), 4.07 (dd, J=10.4, 13.2 Hz, 2H), 4.99 (sept, J=6.4 Hz, 2H), 5.13 (d, J=11.2 Hz, 2H), 7.10-6.98 (m, 8H), 7.35-7.10 (m, 8H), 13.2 (br, 2H). $^{13}$C NMR (101 MHz, CDCl$_3$) δ ppm 15.3, 15.7, 20.3, 21.0, 21.4, 21.8, 25.6, 32.6, 39.6, 41.5, 44.5, 44.6, 44.8, 47.0, 54.8, 58.4, 67.6, 69.2, 76.7, 77.0, 77.4, 125.7, 126.9, 128.2, 128.5, 129.8, 133.9, 134.0, 137.5, 143.8, 170.7, 174.6, 176.3. m.p. 103° C.

Preparation of Compound A Crystalline Anhydrous

To (3S,5R,6S)-3-allyl-5-(3-chlorophenyl)-6-(4-chlorophenyl)-1-((S)-1-(isopropyl sulfonyl)-3-methylbutan-2-yl)-3-methylpiperidin-2-one 1,4-diazabicyclo [2.2.2]octane (DABCO) salt (8.28 Kg, 5.79 mol) were added isopropyl acetate (41.4 L) and water (41.4 L). To the mixture was added 4M aqueous hydrochloric acid (3 L, 12.1 mol) and the biphasic mixture was agitated for 30 minutes. The phases were separated and the organic phases was washed twice with 1M aqueous sodium phosphate pH 6 (25 L) and once with aqueous sodium chloride (7 wt %, 33 L). The mixture was distilled under reduced pressure to produce a distillate mass of 56 Kg while simultaneously adding isopropyl acetate (42 L). The isopropyl acetate content and the water content by Karl Fisher were both measured to be less than one percent in the solution. The organic phase was filtered. The organic phase was distilled under reduced pressure to generate a distillate mass of 20 kg while simultaneously adding acetic acid (45 L). The solution was heated to 60° C. and deionized water (29 L) was added over the course of 30 minutes. (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one seeds (320 g, 0.56 mol) were added as a slurry in acetic acid and deionized water (3/2, 1 L). The mixture was agitated at 60° C. for 3 h, and cooled to 20° C. over the course of 6 h. The mixture was agitated at 20° C. for 12 h. Deionized water (7 mL) was added over the course of 1 h and the mixture was agitated for one additional hour. The product was filtered and the filter cake was washed once with a mixture of acetic acid and deionized water (1/1, 13 L) and three times with deionized water (3×65 L). The product was dried under nitrogen to afford (3S,5R, 6S)-3-allyl-5-(3-chlorophenyl)-6-(4-chlorophenyl)-1-((S)-1-(isopropyl sulfonyl)-3-methylbutan-2-yl)-3-methylpiperidin-2-one (6.3 Kg) in 92% yield (100% LCAP, 100.3 wt %, 320 ppm acetic acid, <100 ppm water).

A synthesis of Compound A is shown in Scheme A. An important intermediate in the synthesis is the compound (3S,5S,6R,8S)-8-Allyl-6-(3-chlorophenyl)-5-(4-chlorophenyl)-3-isopropyl-8-methyl-2,3,5,6,7,8-hexahydrooxazolo[3,2-a]pyridin-4-ium naphthalene-1-sulfonate (also called the "oxoiminium salt" or "oxazolinium salt" herein). Due to difficulties crystallizing the TfO$^-$ or TsO$^-$ salts of (3S,5S, 6R,8S)-8-Allyl-6-(3-chlorophenyl)-5-(4-chlorophenyl)-3-isopropyl-8-methyl-2,3,5,6,7,8-hexahydrooxazolo[3,2-a] pyridin-4-ium naphthalene-1-sulfonate, they were not isolated. Crystallization is useful because it can be used to remove impurities generated in the process or found in the starting materials. Hence, a hydrolysis to a crystalline lactam followed by a re-formation of the oxoiminium salt can be used.

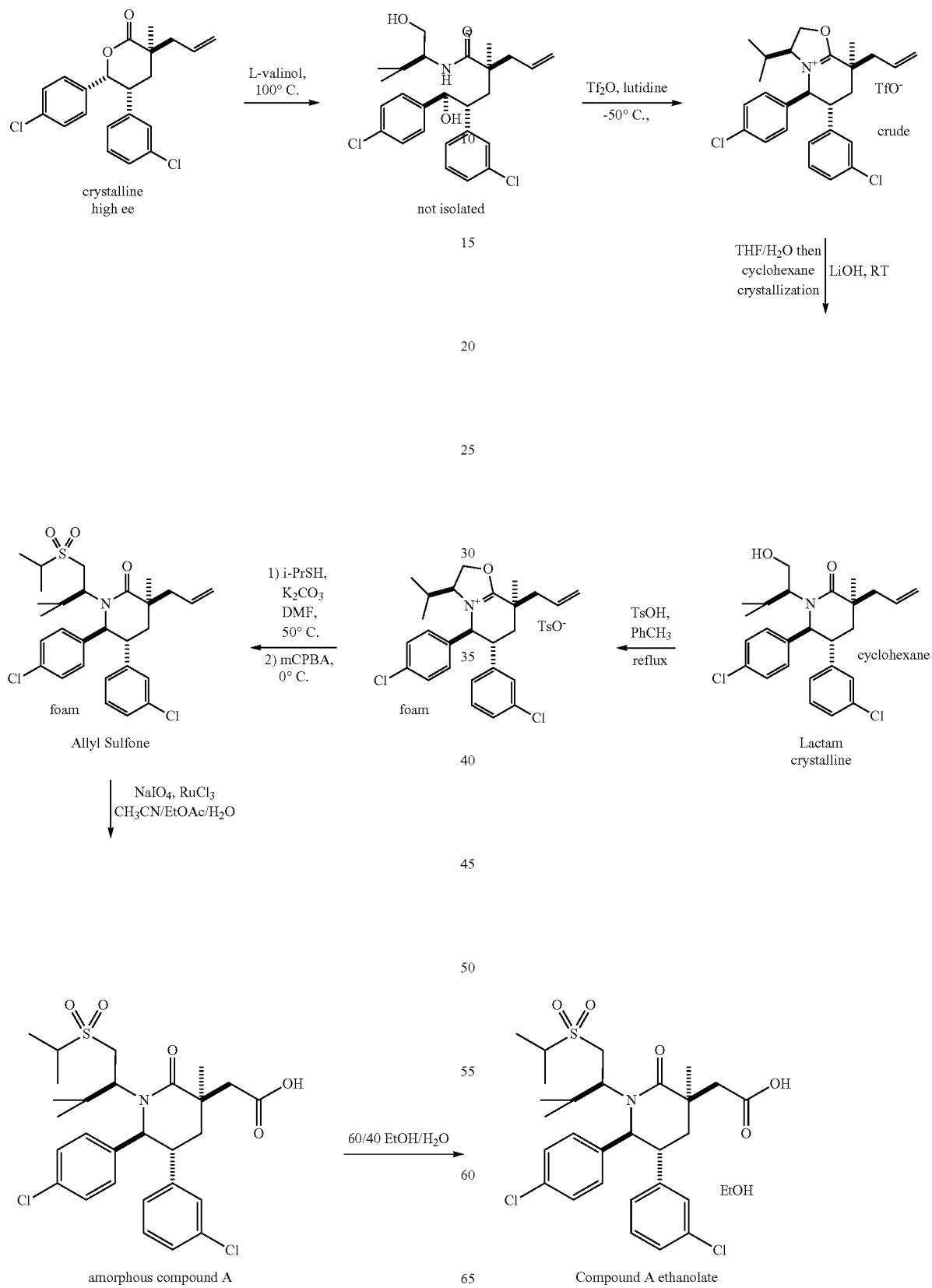
Scheme A

The present invention describes a process to make an oxoiminium naphthalenesulfonate salt, and particularly an oxoiminium naphthalenesulfonate salt, hemi toluene solvate, that is crystalline. Using the oxoiminium naphthalenesulfonate salt, hemi-toluene solvate provides for an improved method of making Compound A (See, Scheme B below).

Scheme B

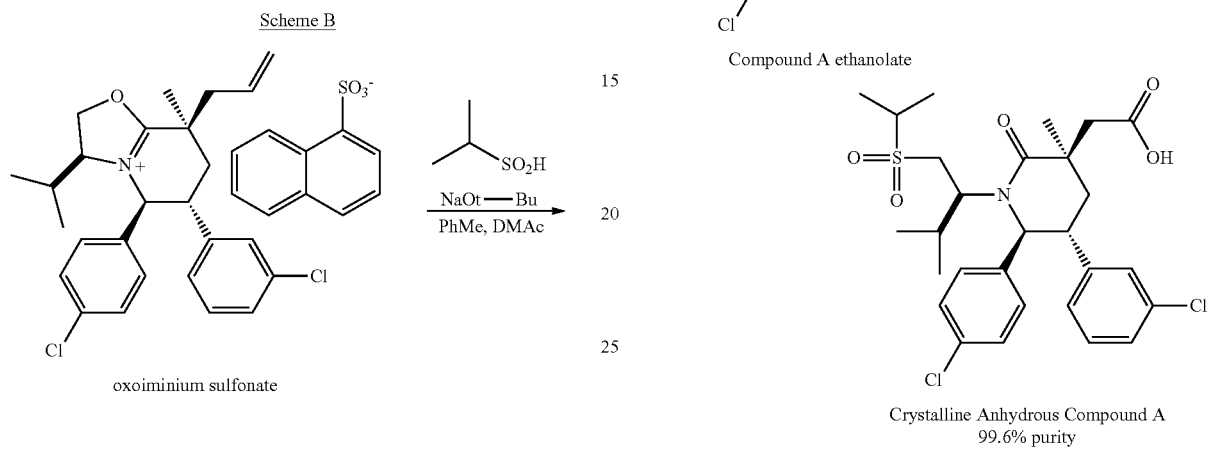

oxoiminium sulfonate

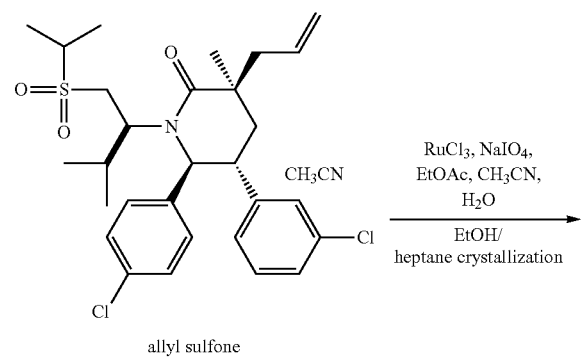

allyl sulfone

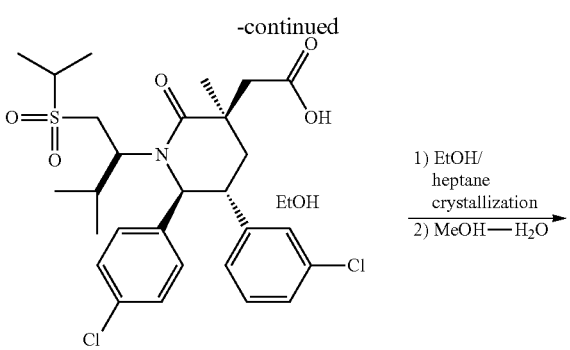

Compound A ethanolate

Crystalline Anhydrous Compound A
99.6% purity

The oxoiminium salt, hemi-toluene hydrate was made by heating (3S,5R,6S)-3-allyl-5-(3-chlorophenyl)-6-(4-chlorophenyl)-1-((S)-1-hydroxy-3-methylbutan-2-yl)-3-methylpiperidin-2-one and 1-naphthalene sulfonic acid in toluene under dehydrative conditions. The crystalline material is characterized as a hemi-toluene solvate by NMR, DSC, and XRPD. This crystalline form is a shelf-stable substance, which is, therefore, well suited as a reagent to make Compound A. One way of making the oxoiminium salt is by ion exchange using 1-naphthalene-sulfonate, followed by crystallization from toluene. It was found that the advantages of using 1-naphthalene sulfonate over other counterions included rapid crystallization kinetics, predictable crystal habit and size, low room-temperature solubility in toluene (<10 mg/ml), high melting point (207-209° C.), and most importantly, high impurity purging capability. All process impurities including stereoisomers were routinely purged to less than 0.5 liquid chromatography area percent (LCAP) with a single crystallization. (See Scheme C below)

Scheme C
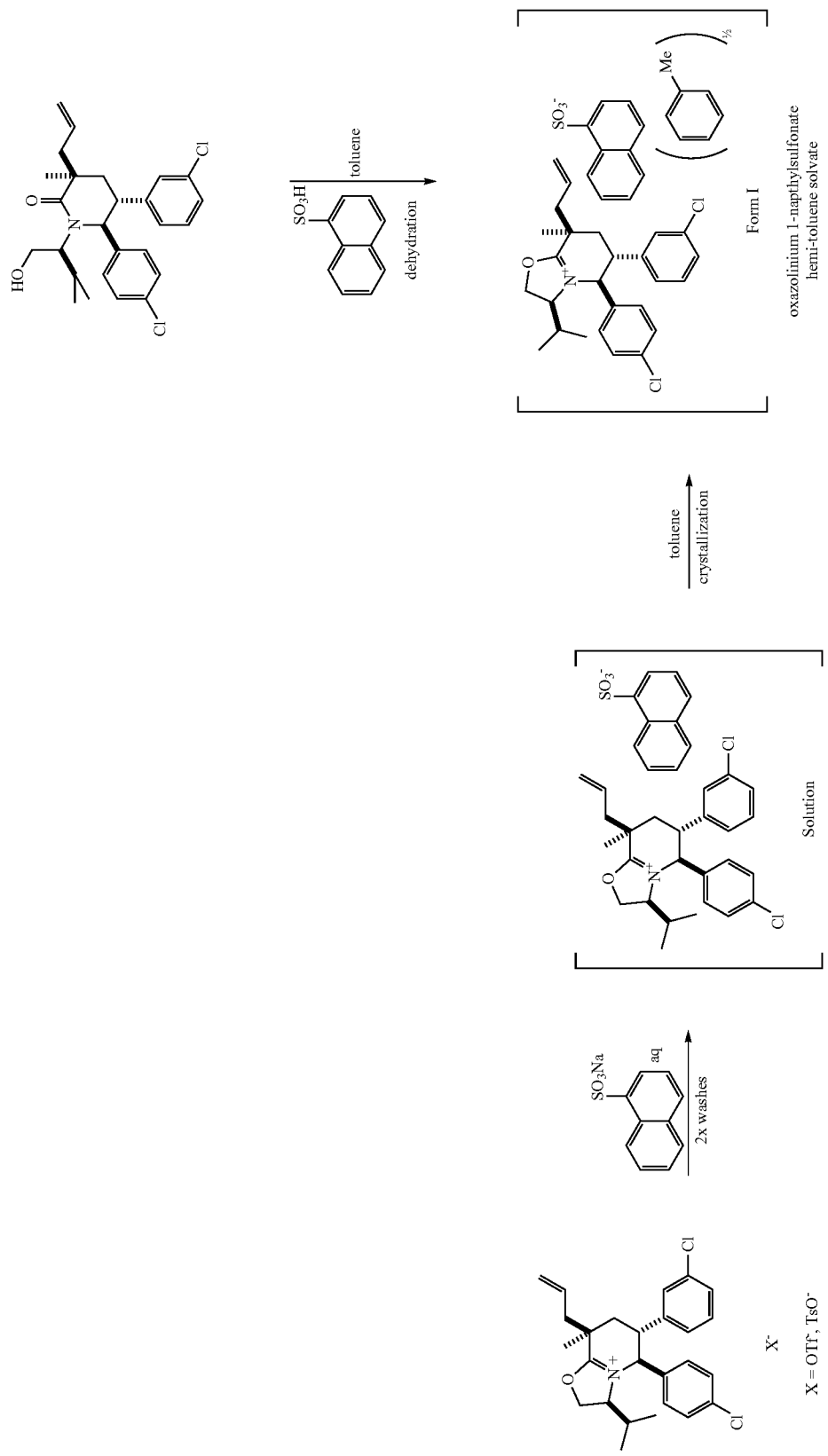

Formation of the oxoiminium salt as shown in Scheme D below could be accomplished by double dehydrative cyclization using Tf₂O under cryogenic conditions (conditions a) or using Ts₂O at elevated temperatures (conditions b).

Scheme D

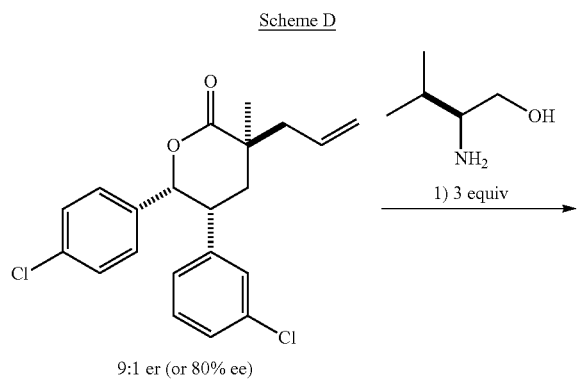

9:1 er (or 80% ee)

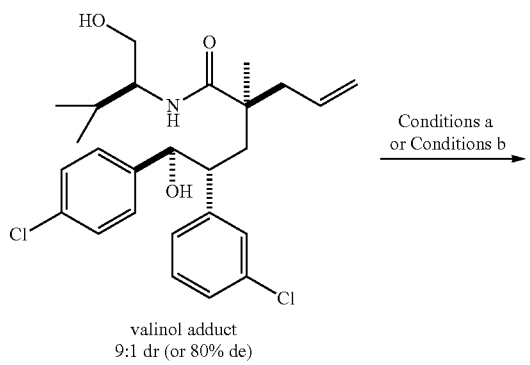

valinol adduct
9:1 dr (or 80% de)

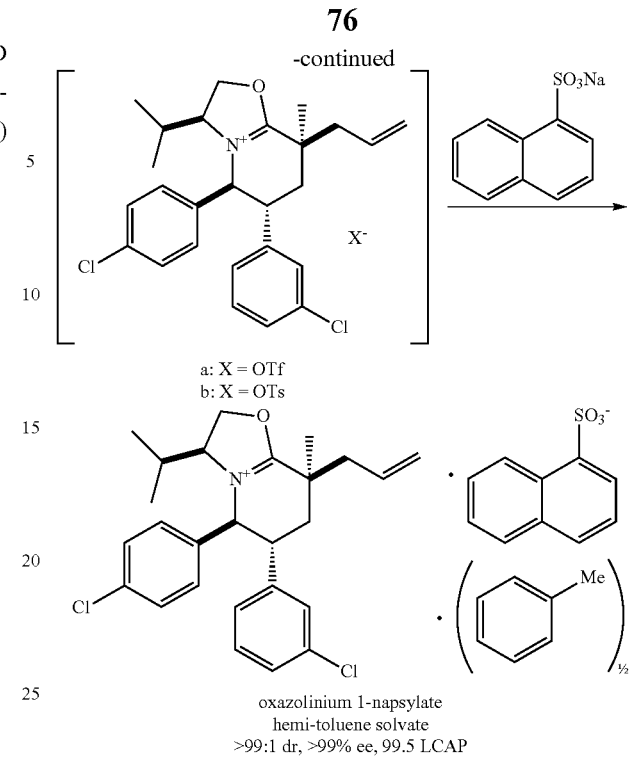

a: X = OTf
b: X = OTs oxazolinium 1-napsylate
hemi-toluene solvate
>99:1 dr, >99% ee, 99.5 LCAP conditions a: Tf₂O, 2,6-lutidine, -40 to -50° C.
conditions b: Ts₂O, 2,6-lutidine, 40-50° C.

The advantages of Conditions a is that the reaction could be performed in a single step. However, these conditions can have side reactions (such as undesirable elimination leading to stilbene-type byproducts) and undesirable cryogenic processing. The latter (conditions b) is a step-wise process, with well characterized formation of intermediates on route to the oxoiminium naphthalenesulfonate salt. Since Ts₂O is a milder reagent, undesirable double cyclizations are significantly reduced and higher yields (>75% vs <60% yield) can be obtained. In addition, the process is more desirable for scale-up under heating conditions.

Scheme E

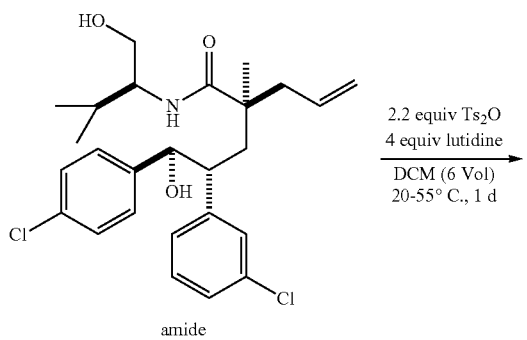

amide

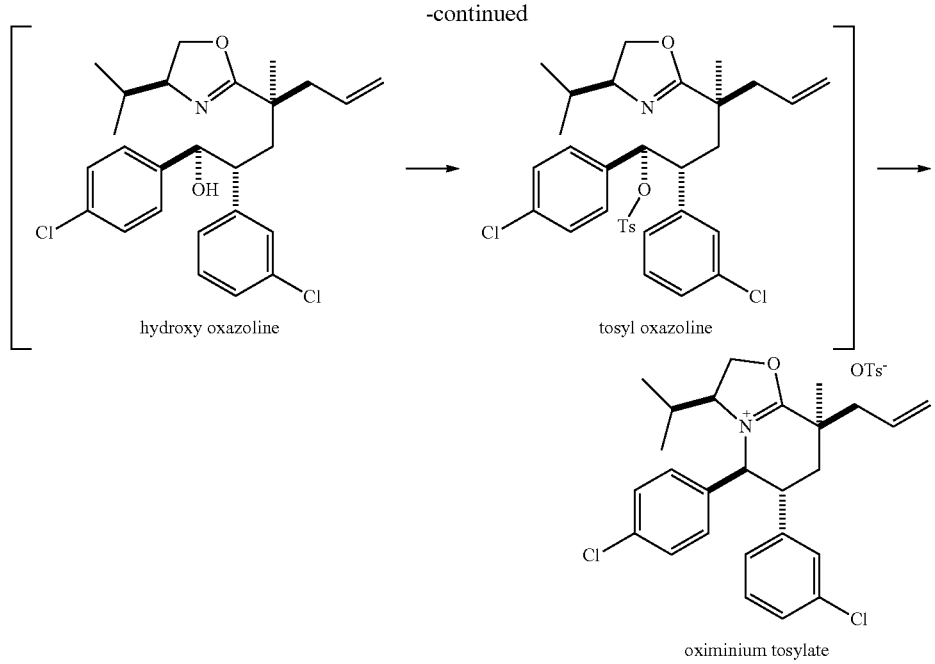

hydroxy oxazoline → tosyl oxazoline → oximinium tosylate

Step-wise conversion of valinol adduct (labeled "amide" in Scheme E) to oxoiminium naphthalenesulfonate salt under Ts₂O conditions is shown in Scheme E.

Below is the a description of the process that enabled multiple kilogram delivery of the oxoiminium salt. The first step of the process is reacting (3S,5R,6R)-3-allyl-5-(3-chlorophenyl)-6-(4-chlorophenyl)-3-methyltetrahydro-2H-pyran-2-one with L-valinol at an elevated temperature. The low optical purity (80% ee) and general purity (85%) of the starting lactones is acceptable. The valinol adduct is formed as a diastereomeric mixture, which is telescoped into subsequent synthetic steps.

In the presence of 2,6-lutidine, the reaction of the valinol adduct (amide in Scheme E) with tosic anhydride is essentially instantaneous at 15 to 25° C., providing hydroxy oxazoline as a stable intermediate. In the presence of additional tosic anhydride and 2,6-lutidine, a second observable reaction intermediate, tosyl oxazoline, forms. Finally, after prolonged heating of the reaction mixture at its reflux temperature (55° C. for 1 day), the reaction proceeds to completion to provide oxoiminium tosylate.

The reaction mixture is quenched with sulfuric acid and washed multiple times with a sodium 1-naphthylsulfonate solution to facilitate counter ion exchange. After a distillation step in which the reaction solvent is switched from dichloromethane to toluene, oxoiminium salt crystallizes as a rod-like hemi-toluene solvate.

In summary, crystalline oxoiminium salt is an isolatable, stable intermediate that is good for purging various impurities such as diastereomers and stilbene using crystallization. As a material to make compound A, the oxoiminium salt, hemi-toluene solvate has desirable features, including isolability in high chemical and stereoisomeric purity, bulk properties suitable for standard manufacturing techniques, and stability to storage.

Scheme F

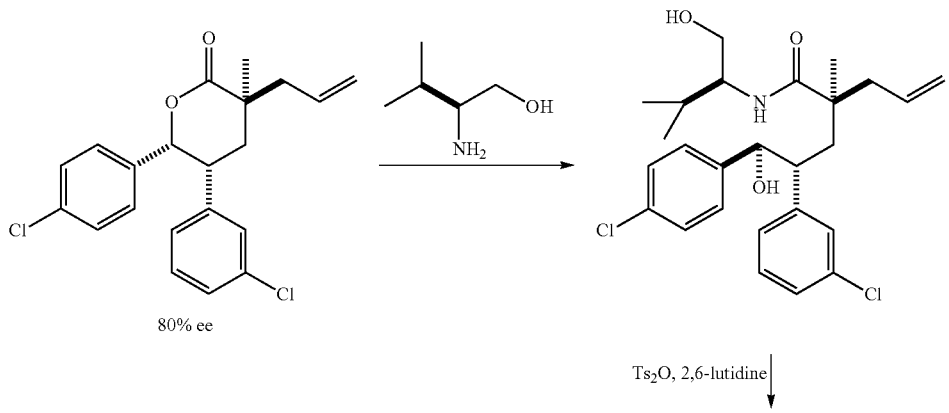

80% ee

Ts₂O, 2,6-lutidine ↓

-continued

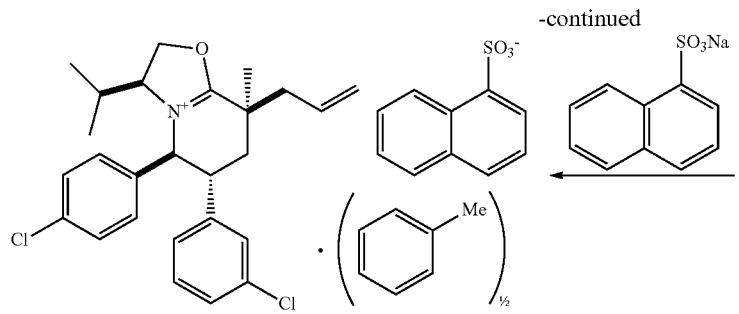
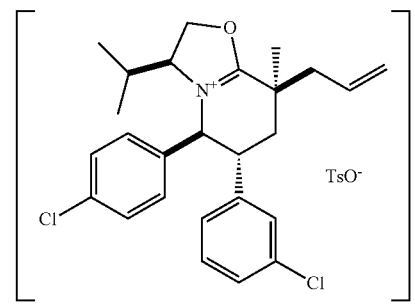

Preparation of Oxoiminium Salt, Hemi-Toluene Solvate:

In accordance with Scheme F, L-Valinol (2.6 Kg, 25.2 mol) was melted at 50° C. and (3S,5R,6R)-3-allyl-5-(3-chlorophenyl)-6-(4-chlorophenyl)-3-methyltetrahydro-2H-pyran-2-one (3.6 Kg, 84.0 wt %, 80.8% ee, 7.9 mol) was added. The mixture was heated to 110° C. and agitated at that temperature for 5 h. The mixture was cooled to 20° C. and dichloromethane (17.9 L) was added. Aqueous 1N hydrochloric acid (18.5 L) was added and the biphasic mixture was agitated for 10 min. The phases were separated and the organic phase was washed with an aqueous sodium chloride solution (20 wt %, 7 L). The organic phase was distilled under atmospheric pressure to produce a distillate mass of 13.7 Kg while simultaneously adding dichloromethane (3.3 L). The organic phase was added over the course of 10 min to a solution of p-toluene sulfonic anhydride (5.9 Kg, 18 mol) in dichloromethane (23.0 L). 2,6-Lutidine (3.56 Kg, 33.2 mol) was added over the course of 1 h, maintaining the temperature of the mixture below 25° C. The mixture was agitated at 20° C. for 40 min. The mixture was distilled under atmospheric pressure and at 40° C. to produce a distillate mass of 13.0 Kg. The mixture was added to aqueous 2N sulfuric acid (19.5 Kg) over the course of 15 min, maintaining the temperature below 20° C. The mixture was agitated for 15 min and the phases were separated. The organic phase was washed twice with an aqueous sodium 1-naphthylsulfonate solution (10 wt %, 19.4 Kg), and once with an aqueous sodium bicarbonate solution (5 wt %, 19.5 Kg). 1-naphthylsulfonic acid dihydrate (64 g, 0.26 mol) was added.

The organic phase was distilled under reduced pressure and maintaining a temperature of 50° C. to produce a distillate mass of 39.9 Kg while simultaneously adding toluene (27.0 L). The mixture was seeded with oxoiminium salt, hemi-toluene solvate (40 g, 0.06 mol) and agitated for 20 min (The seed material was prepared via the same process in a previously conducted smaller scale experiment). The mixture was cooled to 20° C. and agitated for 20 h. The mixture was filtered. The product cake was washed with toluene (7.9 L) and dried under nitrogen to afford oxoiminium salt, hemi-toluene solvate (3.7 Kg, 63.6 wt %, 99.7% ee, 99/1 DR) in 76% yield.

$^1$H NMR (400 MHz, DMSO-$d_6$) δ 8.03-8.00 (m, 1H), 7.93-7.90 (m, 3H), 7.56-7.42 (m, 6.5H), 7.33 (s, 1H), 7.27-7.13 (m, 6H), 5.85 (m, 1H), 5.35 (m, 3H), 5.02 (m, 1H), 4.93 (t, 1H, J=9.98 Hz), 4.3 (m, 1H), 4.09 (m, 1H), 2.79 (m, 2H), 2.39 (t, 1H, J=13.3 Hz), 2.3 (s, 1.5H), 2.01 (dd, 1H, J=13.69, 3.13 Hz), 1.34 (s, 3H), 0.61 (d, 3H, J=6.46 Hz), 0.53 (d, 3H, J=6.85 Hz), 0.41 (m, 1H)

Anhydrous Oxoiminium Salt

The oxoiminium salt, hemi-toluene solvate (1 g) was dissolved in chloroform (10 mL) and the solution was concentrated under reduced pressure. To the residue obtained was added chloroform (10 mL) and the solution was concentrated under reduced pressure again. Finally, to the residue obtained was added chloroform (10 mL) and the solution was concentrated under reduced pressure.

$^1$H NMR (400 MHz, CDCl$_3$) δ 9.13 (d, 1H, J=8.61 Hz), 8.35 (d, 1H, J=7.24 Hz), 7.86 (t, 2H, J=9.0 Hz), 7.57 (m, 1H), 7.48 (m, 2H), 7.28 (m, 5H), 7.09 (m, 3H), 6.11 (d, 1H, J=11.15 Hz), 5.81 (m, 1H), 5.54 (m, 1H), 5.32 (m, 2H), 4.79 (m, 1H), 4.64 (dd, 1H, J=9.00, 4.89 Hz), 3.56 (m, 1H), 2.89 (t, 1H, J=13.69 Hz), 2.65 (m, 2H), 1.97 (dd, 1H, J=14.08, 3.33 Hz), 1.54 (s, 3H), 0.66 (s, 3H), 0.36 (m, 1H), 0.59 (s, 3H)

What is claimed is:
1. A compound, wherein the compound is

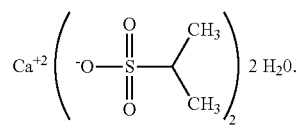

2. A process of making the compound of claim 1, wherein the process comprises reacting propane-2-sulfinic acid with calcium acetate to form the compound of claim 1.

* * * * *